US006440717B1

(12) United States Patent
Brode, III et al.

(10) Patent No.: US 6,440,717 B1
(45) Date of Patent: Aug. 27, 2002

(54) BPN' VARIANTS HAVING DECREASED ADSORPTION AND INCREASED HYDROLYSIS

(75) Inventors: Philip Frederick Brode, III; Bobby Lee Barnett; Donn Nelton Rubingh, all of Cincinnati; Chanchal Kumar Ghosh, West Chester, all of OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 08/397,329

(22) Filed: Mar. 2, 1995

Related U.S. Application Data

(63) Continuation-in-part of application No. 08/287,461, filed on Aug. 11, 1994, now abandoned, and a continuation-in-part of application No. 08/237,939, filed on May 2, 1994, now abandoned, which is a continuation-in-part of application No. 08/121,437, filed on Sep. 15, 1993, now abandoned.

(51) Int. Cl.$^7$ .......................... C12N 9/56; C12N 15/57; C12N 15/75; C11D 3/386
(52) U.S. Cl. ................. 435/222; 435/69.1; 435/252.35; 435/320.1; 435/471; 536/23.2; 510/320; 510/374; 510/392
(58) Field of Search ............................ 435/69.1, 172.3, 435/220, 221, 222, 252.31, 320.1, 471, 476, 477, 252.35; 536/23.2; 510/114, 226, 306, 320, 300, 374, 392

(56) References Cited

U.S. PATENT DOCUMENTS

| | | | |
|---|---|---|---|
| 4,760,025 A | | 7/1988 | Estell et al. ................ 510/392 |
| 4,908,773 A | | 3/1990 | Pantoliano et al. ......... 364/496 |
| 4,914,031 A | | 4/1990 | Zukowsky et al. ......... 435/222 |
| 4,980,288 A | | 12/1990 | Bryan et al. ................ 435/222 |
| 4,990,452 A | | 2/1991 | Bryan et al. ................ 435/222 |
| 5,013,657 A | | 5/1991 | Bryan et al. ............. 435/172.3 |
| 5,116,741 A | | 5/1992 | Bryan et al. .................. 435/87 |
| 5,118,623 A | * | 6/1992 | Boguslawski et al. ....... 435/221 |
| 5,155,033 A | * | 10/1992 | Estell et al. ................ 435/221 |
| 5,182,204 A | * | 1/1993 | Estell et al. ................ 435/222 |
| 5,185,258 A | * | 2/1993 | Caldwell et al. ............ 435/220 |
| 5,208,158 A | * | 5/1993 | Bech et al. ................ 435/219 |
| 5,217,878 A | * | 6/1993 | van Eekelen et al. ...... 435/69.1 |
| 5,240,632 A | * | 8/1993 | Brumbaugh ................ 510/226 |
| 5,244,791 A | * | 9/1993 | Estell ........................ 435/68.1 |
| 5,246,849 A | | 9/1993 | Bryan et al. ................ 435/220 |
| 5,260,207 A | * | 11/1993 | Pantoliano et al. ......... 435/220 |
| 5,275,945 A | * | 1/1994 | Hsiao et al. ................ 435/221 |
| RE34,606 E | * | 5/1994 | Estell et al. ................ 435/222 |
| 5,310,675 A | * | 5/1994 | Estell et al. ............. 435/320.1 |
| 5,316,941 A | * | 5/1994 | Estell et al. ............. 435/252.3 |
| 5,324,653 A | * | 6/1994 | van Eekelen et al. ....... 435/221 |
| 5,336,611 A | * | 8/1994 | van Eekelen et al. ....... 435/221 |
| 5,340,735 A | * | 8/1994 | Christianson et al. ....... 435/221 |
| 5,346,823 A | * | 9/1994 | Estell et al. ................ 435/221 |
| 5,352,603 A | * | 10/1994 | Vetter et al. ................ 435/221 |
| 5,371,008 A | * | 12/1994 | Carter et al. ................ 435/220 |
| 5,371,190 A | * | 12/1994 | Carter et al. ................ 530/350 |
| 5,389,307 A | * | 2/1995 | Lindegaard et al. ........ 510/320 |
| 5,397,705 A | * | 3/1995 | Zukowski et al. .......... 435/222 |
| 5,403,737 A | * | 4/1995 | Abrahmsen et al. ..... 435/252.3 |
| 5,441,882 A | * | 8/1995 | Estell et al. ................ 435/222 |
| 5,453,372 A | * | 9/1995 | Vetter et al. ................ 435/222 |
| 5,470,733 A | * | 11/1995 | Bryan et al. ................ 435/222 |
| 5,472,855 A | * | 12/1995 | Carter et al. .............. 435/68.1 |
| 5,482,849 A | * | 1/1996 | Branner et al. ............. 435/222 |
| 5,500,364 A | * | 3/1996 | Christianson et al. ....... 435/221 |
| 5,567,601 A | * | 10/1996 | Bryan et al. ................ 435/222 |
| 5,629,173 A | * | 5/1997 | Abrahmsen et al. ....... 435/69.1 |
| 5,631,217 A | * | 5/1997 | Branner et al. ............. 510/320 |
| 5,652,136 A | * | 7/1997 | Carter et al. ............. 435/252.3 |
| 5,665,587 A | * | 9/1997 | Aaslyng et al. ............. 435/221 |
| 5,677,272 A | * | 10/1997 | Ghosh et al. ................ 510/306 |
| 5,679,630 A | * | 10/1997 | Baeck et al. ................ 510/305 |
| 5,700,676 A | * | 12/1997 | Bott et al. | |
| 5,707,848 A | * | 1/1998 | Bryan et al. .................. 435/8 |
| 5,736,512 A | * | 4/1998 | Abrahmsen et al. .......... 514/12 |
| 5,741,664 A | * | 4/1998 | Ballinger et al. .......... 435/68.1 |
| 5,741,694 A | * | 4/1998 | Hastrup et al. ............. 435/222 |
| 5,763,257 A | * | 6/1998 | Bott et al. .................. 435/221 |
| 5,801,038 A | * | 9/1998 | Bott et al. .................. 435/221 |
| 5,801,039 A | * | 9/1998 | Maurer et al. .............. 435/221 |
| 5,955,340 A | * | 9/1999 | Bott et al. .................. 435/221 |
| 5,972,682 A | * | 10/1999 | Bott et al. .................. 435/221 |
| 5,985,639 A | * | 11/1999 | Christianson et al. ....... 435/221 |
| 6,197,567 B1 | * | 3/2001 | Aaslyng et al. ............. 435/221 |
| 6,197,589 B1 | * | 3/2001 | Maurer et al. .............. 435/221 |
| 6,271,012 B1 | * | 8/2001 | van Eekelen et al. ....... 435/221 |
| 6,287,841 B1 | * | 9/2001 | Mulleners et al. .......... 435/221 |

FOREIGN PATENT DOCUMENTS

| AU | 8772281 | 11/1987 |
|---|---|---|
| EP | 0 251 446 A2 * | 4/1987 |
| EP | 0 260 105 | 3/1988 |

(List continued on next page.)

OTHER PUBLICATIONS

Thomas, P. G., et al., 1985, "Tailoring the pH dependence of enzyme catalysis using protein engineering to change a single amino acid at BPN' position 99: D99S reduces pKa", Nature, vol. 318, pp. 375–376.*

Russell, A. J. & Fersht, A. R., 1987, "Rational modification of enzyme catalysis by engineering surface charge", Nature, vol. 328, pp. 496–500.*

(List continued on next page.)

Primary Examiner—Ponnathapu Achutamurthy
Assistant Examiner—William W. Moore
(74) Attorney, Agent, or Firm—Bart S. Hersko; Brahm J. Corstanje; Karen F. Clark

(57) ABSTRACT

The present invention relates to subtilisin BPN' variants comprising at least one or more amino acid positions having a different amino acid than that occurring in wild-type subtilisin BPN' (i.e., substitution) at specifically identified positions, whereby the BPN' variant has decreased adsorption to, and increased hydrolysis of, an insoluble substrate as compared to wild-type subtilisin BPN'. The present invention further relates to various cleaning compositions comprising such BPN' variants.

33 Claims, No Drawings

FOREIGN PATENT DOCUMENTS

| | | |
|---|---|---|
| EP | 0 328 229 | 8/1989 |
| EP | 0 357 157 A1 * | 3/1990 |
| EP | 0 380 362 | 8/1990 |
| EP | 0 398 539 | 11/1990 |
| EP | 0 405 901 A1 | 1/1991 |
| EP | 0 405 902 A1 | 1/1991 |
| WO | 87/04461 | 7/1987 |
| WO | 87/05050 | 8/1987 |
| WO | WO 88/08028 A1 * | 10/1988 |
| WO | WO 88/08033 A1 * | 10/1988 |
| WO | 89/06279 | 1/1989 |
| WO | WO 89/07642 A1 * | 8/1989 |
| WO | 89/09830 | 10/1989 |
| WO | 91/00345 | 1/1991 |
| WO | WO 91/14420 A1 * | 11/1991 |
| WO | WO 92/02615 A1 * | 2/1992 |
| WO | WO 92/08778 A1 * | 5/1992 |
| WO | WO 92/11357 * | 7/1992 |
| WO | 94/02618 | 2/1994 |
| WO | 95/07991 | 3/1995 ........... C12N/15/57 |
| WO | WO 95/30010 A1 * | 4/1995 |
| WO | WO 95/30011 A1 * | 4/1995 |

OTHER PUBLICATIONS

Abrahmsén, L., J. Tom, J. Burnier, K. A. Butcher, A. Kossiakoff and J. A. Wells, "Engineering Subtilisin and Its Substrates for Efficient Ligation of Peptide Bonds in Aqueous Solution", Biochemistry, vol. 30, No. 17, pp. 4151–4159 (no month identified 1991).

Arnold, F.H., "Engineering Enzymes for Non–aqueous Solvents", TiBTech, vol. 8, pp. 244–249 (Sep. 1990).

Braxton, S. and J. A. Wells, "The Importance of a Distal Hydrogen Bonding Group in Stabilizing the Transition State in Subtilisin BPN'", The Journal of Biological Chemistry, vol. 266, No. 18, pp. 11797–11800 (Jun. 1991).

Brode, P. F., III and D. S. Rauch, "Subtilisin BPN': Activity on an Immobilized Substrate", Langmuir, vol. 8, No. 5, pp. 1325–1329 (no month identified 1992).

Brode, P.F. III, C.R. Erwin, D.S. Rauch, E.S. Wang, J.M. Armpriester, B.L. Barnett, M.D. Bauer, P.R. Green, D.A. Thaman, and D.N. Rubingh, "Surface Active Variants of Subtilisin BPN': Interfacial Hydrolysis", Abstract, Keystone Symposium (Mar. 6–11, 1994).

Carter, P., L. Abrahmsén and J. A. Wells, "Probing the Mechanism and Improving the Rate of Substrate–Assisted Catalysis in Subtilisin BPN'", Biochemistry, vol. 30, No. 25, pp. 6142–6148 (no month identified 1991).

Carter P. and J. A. Wells, "Functional Interaction Among Catalytic Residues in Subtilisin BPN'", Proteins: Structure, Function, and Genetics, vol. 7, pp. 335–342, (no month identified 1990).

Cunningham, B. C. and J. A. Wells, "Improvement in the Alkaline Stability of Subtilisin Using An Efficient Random Mutagenesis and Screening Procedure", Protein Engineering, vol. 1, No. 4, pp. 319–325 (no month identified 1987).

Egmond, M. R., W. P. Antheunisse, P. Ravestein, A. T. A. Mooren and J. de Vlieg, "Engineering Surface Charges In A Subtilisin", First International Symposium on Subtilisin Enzymes, Hamburg, Germany, (Sep. 1992).

Estell, D.A., "Engineering Enzymes for Improved Performance in Industrial Applications", Journal of Biotechnology, vol. 28, No. 1, pp. 25–30 (Jan. 1993).

Hopp, T. P. and K. R. Woods, "Prediction of Protein Antigenic Determinants From Amino Acid Sequences", Proc. Natl. Acad. Sci. USA, vol. 78, No. 6, pp. 3824–3828 (Jun. 1981).

Mitchinson, C. and J.A. Wells, "Protein Engineering of Disulfide Bonds in Subtilisin BPN'", Biochemistry, vol. 28, No. 11, pp. 4807–4815 (no month identified 1989).

Mizushima, N., D. Spellmeyer, S. Hirono, D. Pearlman and P. Kollman, "Free Energy Perturbation Calculations on Binding and Catalysis ater Mutating Threonine 220 in Subtilisin", Journal of Biological Chemistry, vol. 266, No. 18, pp. 11801–11809 (Jun. 1991).

Pantoliano, M.W., M. Whitlow, J.F. Wood, S.W. Dodd, K.D. Hardman, M.L. Rollence and P.N. Bryan, "Large Increases in General Stability for Subtilisin BPN' through Incremental Changes in the Free Energy of Unfolding", Biochemistry, vol. 28, No. 18, pp. 7205–7213 (no month identified 1989).

Russell, A. J. and A. R. Fersht, "Rational Modification of Enzyme Catalysis by Engineering Surface Charge", Nature, vol. 328, pp. 496–500 (Aug. 1987).

Siezen, R.J., W.M. de Vos, J.A.M. Leunissen and B.W. Dijkstra, "Homology Modelling and Protein Engineering Strategy of Subtilases, the Family of Subtilisin–like Serine Proteinases", Prot. Eng., vol. 4, No. 7, pp. 719–737 (no month identified 1991).

Sternberg, M. J. E., F. R. F. Hayes, A. J. Russell, P. G. Thomas and A. R. Fersht, "Prediction of Electrostatic Effects of Engineering of Protein Charges", Nature, vol. 330, pp. 86–88 (Nov. 1987).

Wells, J.A., B.C. Cunningham, T.P. Graycar and D.A. Estell, "Recruitment of Substrate–specificity Properties from One Enzyme into a Related One by Protein Engineering", Proc. Natl. Acad. Sci., USA,, vol. 84, pp. 5167–5171 (Aug. 1987).

Wells, J.A. and D.A. Estell, "Subtilisin—An Enzyme Designed to be Engineered", TIBS 13, pp. 291–297 (Aug. 1988).

Wong, C.–H., S.–T. Chen, W. J. Hennen, J. A. Bibbs, Y.–F. Wang, J. L.–C. Liu, M. W. Pantoliano, M. Whitlow and P. N. Bryan, "Enzymes in Organic Synthesis: Use of Subtilisin and a Highly Stable Mutant Derived from Multiple Site–Specific Mutations", J. Am. Chem. Soc., vol. 112, No. 3, pp. 945–953 (no month identified 1990).

U. S. patent application No. 08/394,011, Brode et al., filed Mar. 3, 1995.

U. S. patent application No. 08/400,068, Brode et al., filed Mar. 7, 1995.

U. S. patent application No. 08/400,698, Brode et al., filed Mar. 8, 1995.

U. S. patent application No. 08/401,574, Brode et al., filed Mar. 9, 1995.

U. S. patent application No. 08/401,575, Brode et al., filed Mar. 9, 1995.

U. S. patent application No. 08/401,573, Brode et al., filed Mar. 9, 1995.

* cited by examiner

US 6,440,717 B1

BPN' VARIANTS HAVING DECREASED ADSORPTION AND INCREASED HYDROLYSIS

This is a continuation-in-part of application Ser. No. 08/287,461, filed on Aug.11, 1994 and a continuation-in-part of application Ser. No. 08/237,939, filed on May 2, 1994; of which application Ser. No. 08/287,461, filed on Aug. 11, 1994 is a continuation-in-part of application Ser. No. 08/121,437, filed on Sep. 15, 1993.

TECHNICAL FIELD

The present invention relates to novel enzyme variants useful in a variety of cleaning compositions, and the genes encoding such enzyme variants.

BACKGROUND

Enzymes make up the largest class of naturally occurring proteins. Each class of enzyme. generally catalyzes (accelerates a reaction without being consumed) a different kind of chemical reaction. One class of enzymes known as proteases, are known for their ability to hydrolyze (break down a compound into two or more simpler compounds with the uptake of the H and OH parts of a water molecule on either side of the chemical bond cleaved) other proteins. This ability to hydrolyze proteins has been taken advantage of by incorporating naturally occurring and protein engineered proteases as an additive to laundry detergent preparations. Many stains on clothes are proteinaceous and wide-specificity proteases can substantially, improve removal of such stains.

Unfortunately, the efficacy level of these proteins in their natural, bacterial environment, frequently does not translate into the relatively unnatural wash environment. Specifically, protease characteristics such as thermal stability, pH stability, oxidative stability and substrate specificity are not necessarily optimized for utilization outside the natural environment of the enzyme.

The amino acid sequence of the protease determines the characteristics of the protease. A change of the amino acid sequence of the protease may alter the properties of the enzyme to varying degrees, or may even inactivate the enzyme, depending upon the location, nature and/or magnitude of the change in the amino acid sequence. Several approaches have been taken to alter the wild-type amino acid sequence of proteases in an attempt to improve their properties, with the goal of increasing the efficacy of the protease in the wash environment. These approaches include altering the amino acid sequence to enhance thermal stability and to improve oxidation stability under quite diverse conditions.

Despite the variety of approaches described in the art, there is a continuing need for new effective variants of proteases useful for cleaning a variety of surfaces.

OBJECTS OF THE PRESENT INVENTION

It is an object of the present invention to provide subtilisin enzyme variants having improved hydrolysis versus the wild-type of the enzyme.

It is also an object of the present invention to provide cleaning compositions comprising these subtilisin enzyme variants.

SUMMARY

The present invention relates to subtilisin BPN' variants comprising at least one, two or three amino acid positions having a different amino acid than that occurring in wild-type subtilisin BPN' (i.e., substitution) at specifically identified positions, whereby the BPN' variant has decreased adsorption to, and increased hydrolysis of, an insoluble substrate as compared to the wild-type subtilisin BPN'. The present invention also relates to the genes encoding such subtilisin BPN' variants. The present invention also relates to compositions comprising such subtilisin BPN' variants for cleaning a variety of surfaces.

DESCRIPTION

I. Subtilisin Variants

This invention pertains to subtilisin enzymes, in particular BPN', that have been modified by mutating the various nucleotide sequences that code for the enzyme, thereby modifying the amino acid sequence of the enzyme. The modified subtilisin enzymes (hereinafter, "BPN' variants") of the present invention have decreased adsorption to and increased hydrolysis of an insoluble substrate as compared to the wild-type subtilisin. The present invention also pertains to the mutant genes encoding for such BPN' variants.

The subtilisin enzymes of this invention belong to a class of enzymes known as proteases. A protease is a catalyst for the cleavage of peptide bonds. One type of protease is a serine protease. A serine protease is distinguished by the fact that there is an essential serine residue at the active site.

The observation that an enzyme's rate of hydrolysis of soluble substrates increases with enzyme concentration is well documented. It would therefore seem plausible that for surface bound substrates, such as is encountered in many cleaning applications, the rate of hydrolysis would, increase with increasing surface concentration. This has been shown to be the case. (Brode, P. F. III and D. S. Rauch, LANGMUIR, "Subtilisin BPN': Activity on an Immobilized Substrate", Vol. 8, pp. 1325–1329 (1992)). In fact, a linear dependence of rate upon surface concentration was found for insoluble substrates when the surface concentration of the enzyme was varied. (Rubingh, D. N. and M. D. Bauer, "Catalysis of Hydrolysis by Proteases at the Protein-Solution Interface," in POLYMER SOLUTLIONS, BLENDS AND INTERFACES, Ed. by I. Noda and D. N. Rubingh,. Elsevier, p. 464 (1992)). Surprisingly, when seeking to apply this principle in the search for variant proteases which give better cleaning performance, we did not find that enzymes which adsorb more give better performance. In fact, we surprisingly determined the opposite to be the case: decreased adsorption by an enzyme, to a substrate resulted in increased hydrolysis of the substrate (i.e., better cleaning performance).

While not wishing to be bound by theory, it is believed that improved performance, when comparing one variant to another, is a result of the fact that enzymes which adsorb less are also less tightly bound and therefore more highly mobile on the surface from which the insoluble protein substrate is to be removed. At comparable enzyme solution concentrations, this increased mobility is sufficient to outweigh any advantage that is conferred by delivering a higher concentration of enzyme to the surface.

The mutations described herein are designed to change (i.e., decrease) the adsorption of the enzyme to surface-bound soils. In BPN', the amino acids from position 199 to position 220 form a large exterior loop on the enzyme molecule. It has been discovered that this loop plays a significant role in the adsorption of the enzyme molecule to a surface-bound peptide, and specific mutations in this loop-have a significant effect on this adsorption. While not wishing to be bound by theory, it is believed that this loop is important to the adsorption of the BPN' molecule for at least two reasons. First, the amino acids which comprise this exterior loop can make close contacts with any surfaces to which the molecule is exposed. Second, the proximity of this loop to the active-site and binding pocket of the BPN' molecule gives it a role in the catalytically productive adsorption of the enzyme to surface-bound substrates (peptides/protein soils).

As used herein, "variant" means an enzyme having an amino acid sequence which differs from that of wild-type.

As used herein, "mutant BPN' gene" means a gene coding for a BPN' variant.

As used herein, "wild-type subtilisin BPN'" refers to a subtilisin enzyme represented by SEQ ID NO:1. The amino acid sequence for subtilisin BPN' is further described by Wells, J. A., E. Ferrari, D. J. Henner, D. A. Estell and E. Y. Chen, NUCLEIC ACIDS RESEARCH, Vol. II, 7911–7925 (1983), incorporated herein by reference.

As used herein, the term "wild-type amino acid sequence" encompasses SEQCID NO:1 as well as SEQ ID NO:1 having modifications to the amino acid sequence other than at any of positions 199–220.

As used herein, "more hydrophilic amino acid" refers to any other amino acid having greater hydrophilicity than a subject amino acid with reference to the hydrophilicity table below. The following hydrophilicity table (Table 1) lists amino acids in descending order of increasing hydrophilicity (see Hopp, T. P., and Woods, K. R., "Prediction of Protein Antigenic Determinants from Amino Acid Sequences", PROCEEDINGS OF THE NATIONAL ACADEMY OF SCIENCE USA, Vol. 78, pp. 3824–3828, 1981, incorporated herein by reference).

TABLE 1

| Amino Acid | Hydrophilicity Value |
| --- | --- |
| Trp | −3.4 |
| Phe | −2.5 |
| Tyr | −2.3 |
| Leu, Ile | −1.8 |
| Val | −1.5 |
| Met | −1.3 |
| Cys | −1.0 |
| Ala, His | −0.5 |
| Thr | −0.4 |
| Pro, Gly | −0.0 |
| Gln, Asn | 0.2 |
| Ser | 0.3 |
| $Arg^+$, $Lys^+$, $Glu^-$, $Asp^-$ | 3.0 |

Table 1 also indicates which amino acids carry a charge (this characteristic being based on a pH of from about 8–9). The positively charged amino acids are Arg and Lys, the negatively charged amino acids are Glu and Asp, and the remaining amino acids are neutral. In a preferred embodiment of the present invention, the substituting amino acid is either neutral or negatively charged, more preferably negatively charged (i.e., Glu or Asp).

Therefore, for example, the statement "substitute Gln with an equally or more hydrophilic amino acid which is neutral or has a negative charge" means Gln would be substituted with Asn (which is equally hydrophilic to Gln), or Ser, Glu or Asp (which are more hydrophilic than Gln); each of which are neutral or have a negative charge, and have a greater hydrophilicity value as compared to Gln. Likewise, the statement "substitute Pro with a more hydrophilic amino acid which is neutral or has a negative charge" means Pro would be substituted with Gln, Asn, Ser, Glu or Asp.

A. Variants Comprising at Least One Amino Acid Substitution

In one embodiment of the present invention, the BPN' variant comprises wild-type amino acid sequence wherein the wild-type amino acid sequence at one or more of positions 199, 200, 201, 202, 203, 204, 205, 206, 207, 208, 209, 210, 211, 212, 213, 214, 215, 216, 218, 219 or 220 is substituted; whereby the BPN' variant has decreased adsorption to, and increased hydrolysis of, an insoluble substrate as compared to the wild-type subtilisin BPN'. Preferably, the positions having a substituted amino acid are 199, 200, 201,202, 205,207, 208,209,210,211, 212 or 215; more preferably, 200, 201, 202, 205 or 207.

Preferably, the substituting amino acid for position 199 is Cys, Ala, His, Thr, Pro, Gly, Gln, Asn, Ser, Asp or Glu.

Preferably, the substituting amino acid for position 200 is His, Thr, Pro, Gly, Gln, Asn, Ser, Asp or Glu.

Preferably, the substituting amino acid for position 201 is Gly, Gln, Asn, Ser, Asp or Glu.

Preferably, the substituting amino acid for position 202 is Pro, Gln, Asn, Ser, Asp or Glu.

Preferably, the substituting amino acid for position 203 is Met, Cys, His, Pro, Gly, Gln, Asn, Ser, Asp or Glu.

Preferably, the substituting amino acid for position 204 is Glu.

Preferably, the substituting amino acid for position 205 is Leu, Met, Cys, Ala, His, Thr, Pro, Gly, Gln, Asn, Ser, Asp or Glu.

Preferably, the substituting amino acid for position 206 Pro, Asn or Ser.

Preferably, the substituting amino acid for position 207 is Asp or Glu.

Preferably, the substituting amino acid for position 208 is Pro, Gly, Gln, Asn or Ser.

Preferably, the substituting amino acid for position 209 is Ile, Val, Met, Cys, Ala, His, Thr, Pro, Gly, Gln, Asn, Ser, Asp or Glu.

Preferably, the substituting amino acid for position 210 is Gly, Gln, Asn, Ser, Asp or Glu.

Preferably, the substituting amino acid for position 211 is Ala, Pro, Gln, Asn, Ser, Asp or Glu.

Preferably, the substituting amino acid for position 212 is Gln, Ser, Asp or Glu.

Preferably, the substituting amino acid for position 213 is Trp, Phe, Tyr, Leu, lie, Val, Met, Cys, Ala, His, Pro, Gly, Gln, Asn, Ser or Glu.

Preferably, the substituting amino acid for position 214 is Phe, Leu, Ile, Val, Met, Cys, Ala, His, Pro, Gly, Gln or Asn.

Preferably, the substituting amino acid for position 215 is Thr, Pro, Gln, Asn, Ser, Asp or Glu.

Preferably, the substituting amino acid for.position 216 is His, Thr, Pro, Gly, Gln, Asn, Ser, Asp or Glu.

Preferably, the substituting amino acid for position 218 is Glu.

Preferably, the substituting amino acid for position 219 is Pro, Gln, Asn, Ser, Asp or Glu.

Preferably, the substituting amino acid for position 220 is Pro, Gly, Gln, Asn, Asp or Glu.

More preferably, the substituting amino acid for any of positions 199, 200, 201, 202, 203, 205, 207, 208, 209, 210, 211, 212, 213, 214, 215, 216, 219 and 220 is, with references to Table 1, neutral or negatively charged and equally or more hydrophilic, preferably more hydrophilic, than the amino acid at the subject position in wild-type subtilisin BPN'.

More preferably still, the substituting amino acid for any of positions 199, 200, 201, 202, 203, 205, 207, 209, 210, 211, 212, 215, 216, 219 and 220 is Asp, or Glu; and the substituting amino acid for positions 204, 213 or 218 is Glu.

B. Variants Comprising at Least Two Amino Acid Substitutions

In another embodiment of the present invention, the BPN' variant comprises wild-type amino acid sequence wherein the wild-type amino acid sequence at two or more of positions 199, 200, 201, 202, 203, 204, 205, 206, 207, 208, 209, 210, 211, 212, 213, 214, 215, 216, 217, 218, 219 or 220 is substituted; whereby the BPN' variant has decreased adsorption to, and increased hydrolysis of, an insoluble substrate as compared to wild-type subtilisin BPN'. Preferably, the positions having a substituting amino acid are 99, 200, 201, 202, 205, 207, 208, 209, 210, 211, 212, or 215; more preferably, positions 200, 201, 202, 205 or 207.

Preferably, the substituting amino acid for position 199 is Cys, Ala, His, Thr, Pro, Gly, Gln, Asn, Ser, Asp or Glu.

Preferably, the substituting amino acid for position 200 is His, Thr, Pro, Gly, Gln, Asn, Ser, Asp or Glu.

Preferably, the substituting amino acid for position 201 is Gly, Gln, Asn, Ser, Asp or Glu.

Preferably, the substituting amino acid for position 202 is Pro, Gln, Asn, Ser, Asp or Glu.

Preferably, the substituting amino acid for position 203 is Met, Cys, Ala, His, Thr, Pro, Gly, Gln, Asn, Ser, Asp or Glu.

Preferably, the substituting amino acid for position 204 is Asp or Glu.

Preferably, the substituting amino acid for position 205 is Leu, Val, Met, Cys, Ala, His, Thr, Pro, Gly, Gln, Asn, Ser, Asp or Glu.

Preferably, the substituting amino acid for position 206 is Pro, Asn, Ser, Asp, or Glu.

Preferably, the substituting amino acid for position 207 is Asp or Glu.

Preferably, the substituting amino acid for position 208 is Pro, Gly, Gln, Asn, Ser, Asp or Glu.

Preferably, the substituting amino acid for position 209 is Ile, Val, Met, Cys, Ala, His, Thr, Pro, Gly, Gln, Asn, Ser. Asp or Glu.

Preferably, the substituting amino acid for position 210 is Ala, Gly, Gln, Asn, Ser, Asp or Glu.

Preferably, the substituting amino acid for position 211 is Ala, Pro, Gln, Asn, Ser, Asp or Glu.

Preferably, the substituting amino acid for position 212 is Gln, Ser, Asp or Glu.

Preferably, the substituting amino acid for position 213 is Trp, Phe, Tyr, Leu, Ile, Val, Met, Cys, Ala, His, Thr, Pro,. Gly, Gln, Asn, Ser, Asp or Glu.

Preferably, the substituting amino acid for position 214 is Phe, Leu, Ile, Val, Met, Cys, Ala, His, Thr, Pro, Gly, Gln, Asn, Ser, Asp or Glu.

Preferably, the substituting amino acid for position 215 is Thr, Pro, Gln, Asn, Ser, Asp or Glu.

Preferably, the substituting amino acid for position 216 is His, Thr, Pro, Gly, Gln, Asn, Ser, Asp or Glu.

Preferably, the substituting amino acid for position 217 is Leu, Ile, Val, Met, Cys, Ala, His, Thr, Pro, Gly, Gln, Asn, Ser, Asp or Glu.

Preferably, the substituting amino acid for position 218 is Gln, Ser, Asp or Glu.

Preferably, the substituting amino acid for position 2.19 is Pro, Gln, Asn, Ser, Asp or Glu.

Preferably, the substituting amino. acid for position 220 is Pro, Gly, Gln, Asn, Ser, Asp or Glu.

More preferably, the substituting amino acid for any of positions 199, 200, 201, 202, 203, 204, 205, 206, 207, 208, 209, 210, 211, 212, 213, 214, 215, 216, 217, 218, 219 or 220 is, with reference to Table 1, neutral or negatively charged and equally or more more hydrophilic, preferably more hydrophilic, than the amino acid at the subject position in wild-type subtilisin BPN'.

More preferably still, the substituting amino acid for any of positions 199, 200, 201, 202, 203, 204, 205, 206, 207, 208, 209, 210, 211, 212, 213, 214, 215, 216, 218, 219 or 220 is Asp and Glu; for position 217 is Leu, Asp or Glu; and for position 213 is Asp.

C. Variants Comprising at Least Three Amino Acid Substitutions

In another embodiment of the present invention, the BPN' variant comprises wild-type amino acid sequence wherein the wild-type amino acid sequence of three or more of positions 199, 200, 201, 202, 203, 204, 205, 206, 207, 208, 209, 210, 211, 212, 213, 214, 215, 216, 217, 218, 219 and 220, is substituted; whereby the BPN' variant has decreased adsorption to, and increased hydrolysis of, an insoluble substrate as compared to wild-type subtilisin BPN'. Preferably, the positions having a substituting amino acid are 199, 200, 201, 202, 205, 207, 208, 209, 210, 211, 212, or215; more preferably positions 200, 201, 202, 205 or 207.

Preferably, the substituting amino acid for position 199 is Cys, Ala, His, Thr, Pro, Gly, Gln, Asn, Ser, Asp or Glu.

Preferably, the substituting amino acid for position 200 is His, Thr, Pro, Gly, Gln, Asn, Ser, Asp or Glu.

Preferably, the substituting amino acid for position 201 is Gly, Gln, Asn, Ser, Asp or Glu.

Preferably, the substituting amino acid for position 202 is Pro, Gln, Asn, Ser, Asp or Glu.

Preferably, the substituting amino acid for position 203 Met, Cys, Ala, His, Thr, Pro, Gly, Gln, Asn, Ser, Asp or Glu.

Preferably, the substituting amino acid for position 204 is selected from the group consisting of Asp or Glu.

Preferably, the substituting amino acid for position 205 is Leu, Val, Met, ys, Ala, His, Thr, Pro, Gly, Gln, Asn, Ser, Asp or Glu.

Preferably, the substituting amino acid for position 206 is Pro, Asn, Ser, Asp, or Glu.

Preferably, the substituting amino acid for position 207 is Asp or Glu.

Preferably, the substituting amino acid for position 208 is Pro, Gly, Gln, Asn, Ser, Asp or Glu.

Preferably, the substituting amino acid for position 209 is Ile, Val, Met, Cys, Ala, His, Thr, Pro, Gly, Gln, Asn, Ser, Asp or Glu.

Preferably, the substituting amino acid for position 210 is Ala, Gly, Gln, Asn, Ser, Asp or Glu.

Preferably, the substituting amino acid for position 211 is Ala, Pro, Gln, Asn, Ser, Asp or Glu.

Preferably, the substituting amino acid for position 212 is Gln, Ser, Asp or Glu.

Preferably, the substituting amino acid for position 213 is Trp, Phe, Tyr, Leu, Ile, Val, Met, Cys, Ala, His, Thr, Pro, Gly, Gln, Asn, Ser, Asp or Glu.

Preferably, the substituting amino acid for position 214 is Phe, Leu, Ile, Val, Met, Cys, Ala, His, Thr, Pro, Gly, Gln, Asn, Ser, Asp or Glu.

Preferably, the substituting amino acid for position 215 is Thr, Pro, Gln, Asn, Ser, Asp or Glu.

Preferably, the substituting amino acid for position 216 is His, Thr, Pro, Gly, Gln, Asn, Ser, Asp or Glu.

Preferably, the substituting amino acid for position 217 is Leu, Ile, Val, Met, Cys, Ala, His, Thr, Pro, Gly, Gln, Asn, Ser, Asp or Glu.

Preferably, the substituting amino acid for position 218 is Gln, Ser, Asp or Glu.

Preferably, the substituting amino acid for position 219 is Pro, Gln, Asn, Ser, Asp or Glu.

Preferably, the substituting amino acid for position 220 is Pro, Gly, Gln, Asn, Ser Asp or Glu.

More preferably, the substituting amino acid for any of positions 199, 200, 201, 202, 203, 205, 206, 207, 208, 209, 210, 211, 212, 213, 214, 215, 216, 217, 218, 219 or 220 is, with reference to Table 1, neutral or negatively charged and equally or more hydrophilic, preferably more hydrophilic, than the amino acid at the subject position in wild-type subtilisin BPN'.

More preferably still, the substituting amino acid for any of positions 199, 200, 201, 202, 203, 204, 205, 206, 207, 208, 209, 210, 211, 212, 213, 214, 215, 216, 218, 219 or 220 is Asp or Glu; for position 217 is Leu, Asp or 35 Glu; and for position 213 is Asp.

D. Preparation of Enzyme Variants

EXAMPLE 1

Mutant BPN' Genes

A phagemid (pSS-5) containing the wild type subtilisin BPN' gene (Mitchinson, C. and J. A. Wells, (1989), "Protein Engineering of Disulfide Bonds in Subtilisin BPN', BIOCHEMISTRY, Vol. 28, pp. 4807–4815) is transformed into *Eschetichia coli* ungstrain CJ236 and a single stranded uracil-containing DNA template is produced using the VCSM13 helper phage (Kwnkel, T. A., J. D. Roberts and R. A. Zakour, "Rapid and efficient site-specific mutagenesis without phenotypic selection", METHODS IN ENZYMOLOGY, Vol. 154, pp. 367–382, (1987); as modified by Yuckenberg, P. D., F. Witney, J. Geisselsoder and J. McClary, "Site-directed in vitro mutagenesis using uracil-containing DNA and phagemid vectors", DIRECTED MUTAGENESIS—A PRACTICAL APPROACH, ed. M. J. McPherson, pp. 27–48, (1991); both of which are incorporated herein by reference). A single primer site-directed mutagenesis modification of the method of Zoller and Smith (Zoller, M. J., and M. Smith, "Oligonucleotide-directed mutagenesis using M13-derived vectors: an efficient and general procedure for the production of point mutations in any fragment of DNA", NUCLEIC ACIDS RESEARCH, Vol. 10, pp. 6487–6500, (1982), incorporated herein by reference) is used to produce all mutants (basically as presented by Yuckenberg, et al., 1991, above). Oligonucleotides are made using an Applied Biosystem Inc. 380B DNA synthesizer. Mutagenesis reaction products are transformed into Escherichia coli strain MM294 (American Type Culture Collection *E. Coli*. 33625). All mutants are confirmed by DNA sequencing and the isolated DNA is transformed into the *Bacillus subtilis* expression strain BG2036 (Yang, M. Y., E. Ferrari and D. J. Henner, (1984), "Cloning of the Neutral Protease Gene of *Bacillus subtillis* and the Use of the Cloned Gene to Create an In Vitro-derived Deletion Mutation", JOURNAL OF BACTERIOLOGY, Vol. 160, pp. 15–21). For some of the mutants a modified pSS-5 with a frameshift-stop codon mutation at amino acid 217 is used to produce the uracil template. Oligonucleotides are designed to restore the proper reading frame at position 217 and also encoded for random substitutions at positions 199, 200, 201, 202, 203, 204, 205, 206, 207, 208, 209, 210, 211, 212, 213, 214, 215, 216, 217, 218, 219 and 220 (equimolar and/or variable mixtures of all four nucleotides for all three bases at these codons). Mutations that correct for the frameshift-stop and produce a functional enzyme are identified by their ability to digest casein. The random substitutions are determined by DNA sequencing.

EXAMPLE 2

Fermentation

The *Bacillus subtilis* cells (BE2036) containing a subtilisin mutant of interest are grown to mid-log phase in a one liter culture of LB-glucose broth and inoculated into a Biostat ED fermenter (B. Braun Biotech, Inc., Allentown, Pa.) in a total volume of 10 liters. The fermentation media contains Yeast Extract, starch, antifoam, buffers and trace minerals (see FERMENTATION: A PRACTICAL APPROACH, Ed. B. McNeil and L. M. Harvey, 1990). The broth is kept at a constant pH of 7.0 during the fermentation run. Chloramphenical is added for antibiotic selection of mutagenized plasmid. The cells are grown overnight at 37° C. to an $A_{600}$ of about 60 and harvested.

EXAMPLE 3

Purification

The fermentation broth is taken through the following steps to obtain pure enzyme. The broth is cleared of *Bacillus subtilis* cells by centrifugation, and clarified by removing fine particulates with a 100K cutoff membrane. This is followed by concentration on a 10K cutoff membrane, and flow dialysis to reduce the ionic strength and adjust the pH to 5.5 using 0.025M MES buffer (2-(N-morpholino) ethanesulfonic acid). The enzyme is further purified by loading it onto either a cation exchange chromatography column or an affinity adsorption chromatography column and eluting it from the column with a NaCl or a propylene glycol gradient (see Scopes, R. K., PROTEIN PURIFICATION PRINCIPLES AND PRACTICE, Springer-Verlag, New York (1984), incorporated herein by reference).

The pNA assay (DelMar, E. G., C. Largman, J. W. Brodrick and M. C. Geokas, ANAL. BIOCHEM., Vol. 99, pp. 316–320, (1979), incorporated herein by reference) is used to determine the active enzyme concentration for fractions collected during gradient elution. This assay measures the rate at which p-nitroaniline is released as the enzyme hydrolyzes the soluble synthetic substrate, succinyl-alanine-alanine-proline-phenylalanine-pnitroanilide (sAAPF-pNA). The rate of production of yellow color from the hydrolysis reaction is measured at 410 nm on a spectrophotometer and is proportional to the active enzyme concentration. In addition, absorbance measurements at 280 nm are used to determine the total protein concentration. The active enzyme/total-protein ratio gives the enzyme purity, and is used to identify fractions to be pooled for the stock solution.

To avoid autolysis of the enzyme during storage, an equal weight of propylene glycol is added to the pooled fractions obtained from the chromatography column. Upon completion of the purification procedure the purity of the stock enzyme solution is checked with SBS-PAGE (sodium dodecyl sulfate polyacrylamide gel electrophoresis) and the absolute enzyme concentration is determined via an active site titration method using trypsin inhibitor type II-T: turkey egg white purchased from Sigma Chemical Company (St. Louis, Mo.). The measured conversion factors will show which changes made in the enzyme molecule at the various positions result in the enzyme variant having increased activity over the wild-type, against the soluble substrate pNA.

In preparation for use, the enzyme stock solution is eluted through a Sephadex-G25 (Pharmacia, Piscataway, New Jersey) size exclusion column to remove the propylene glycol and exchange the buffer. The MES buffer in the enzyme stock solution is exchanged for 0.1M Tris buffer (Tris(hydroxymethyl-aminomethane) containing 0.01M $CaCl_2$ and pH adjusted to 8.6 with HCl. All experiments are carried out at pH 8.6 in Tris buffer thermostated at 25° C.

E. Characterization of Enzyme Variants

EXAMPLE 4

Model Surface Preparation

Aminopropyl controlled pore glass (CPG) purchased from CPG Inc. (Fairfield, N.J.) is used as a support for covalently attaching the sMPF-pNA substrate purchased from Bachem, Inc. (Torrence, Calif.).

The reaction is carried out in dimethyl sulfoxide and (1-ethyl-3-[3-(dimethylamino)propyl] carbodiimide -hydrochloride) (EDC) is used as a coupling agent. Upon completion (monitored by pNA assay), the excess solvent is removed, and the CPG:sAAPF-pNA is rinsed with dimethyl sulfoxide (DMSO) and doubly-distilled water. This is followed by oven drying with a $N_2$ purge at about 70° C. The reaction scheme and preparation of the immobilized substrate are conducted as described by Brode, P. F. III, and D. S. Rauch, "Subtilisin BPN': Activity on an Immobilized Substrate," LANGMUIR, Vol. 8, p. 1325–1329, (1992), incorporated herein by reference.

The CPG surface will have 62,000±7,000 pNA molecules/ $\mu m^2$. The surface area will remain unchanged from the value of 50.0 $m^2/g$ reported by CPG Inc. for the CPG as received. This suggests that the procedure used to add sAAPF-pNA to CPG does not damage the porous structure (mean diameter is 486 Å).

EXAMPLE 5

Surface Hydrolysis Assay

Using CPG:sMPF-pNA, adsorption of an enzyme variant and hydrolysis of a CPG-bound peptide can be measured in a single experiment. A small volume of enzyme variant stock solution is added to a flask containing Tris buffer and CPG:sAAPF-pNA which has been degassed. The flask is shaken on a wrist-action shaker for a period of 90 minutes during which the shaker is stopped at various time intervals (for example, every 2 minutes during the early stages of adsorption hydrolysis—e.g., the first 20 minutes— and every 10 minutes towards the end of the experiment). The CPG:sAAPF-pNA is allowed to settle and the solution is sampled. Both the experimental procedure and the calculation of the adsorption and hydrolysis are conducted as described by Brode et al., 1992, above.

All enzymes are monitored for stability against autolysis and should show no appreciable autolytic loss over the time course of this experiment. Therefore, enzyme adsorption can be determined by measuring solution depletion. The difference between the initial enzyme variant concentration and the concentration measured at each individual time point gives the amount of enzyme variant adsorbed. The amount of pNA hydrolyzed from the surface is measured by taking an absorbance reading on an aliquot of the sample at 410 nm. The total amount of pNA hydrolyzed is calculated by adding the amount sampled and the amount remaining in the flask. This value is corrected by subtracting the amount of pNA that is hydrolyzed by Tris buffer at pH 8.6 when no enzyme is present. This base-hydrolysis ranges from 7–29% of the total hydrolysis depending on the efficiency of the enzyme.

EXAMPLE 6

Soluble Substrate Kinetic Analysis

The rates of hydrolysis of the soluble substrate sAAPF-pNA are monitored by measuring the adsorbance increase as a function of time at 410 nm on a DU-70 spectrophotometer. The enzyme concentration is held constant and is prepared to be in the range of 6–10 nanomolar while the substrate concentration is varied from 90–700 $\mu M$ sAAPF-pNA for each kinetic determination. An adsorbance data point is taken each second over a period of 900 seconds and the data are transferred to a LOTUS™ spreadsheet (Lotus Development Corporation, Cambridge, Mass.). Analysis for kinetic parameters is conducted by the standard Lineweaver Burk analysis in which the data in the initial part of the run (generally the first minute) are fit to a linear regression curve to give $v_o$. The $v_o$ and $s_o$ data are plotted in the standard inverse fashion to give $K_M$ and $k_{cat}$.

F. Example BPN' Variants

BPN' variants of the present invention which have decreased adsorption to and increased hydrolysis of surface bound substrates are exemplified in Tables 2–11, below (preferred specific variants are exemplified in Table 12, below). In describing the specific mutations, the original amino acid occurring in wild-type is given first, the position number second, and the substituted amino acid third.

TABLE 2

| Single Mutation BPN' Variants |
|---|
| Met199Ala |
| Met199Asn |
| Met199Asp |
| Met199Cys |
| Met199Gln |
| Met199Glu |
| Met199Gly |
| Met199His |
| Met199Pro |
| Met199Ser |
| Met199Thr |
| Ala200Asn |
| Ala200Asp |
| Ala200Gln |
| Ala200Glu |
| Ala200Gly |
| Ala200His |
| Ala200Pro |
| Ala200Ser |
| Ala200Thr |
| Pro201Asn |
| Pro201Asp |
| Pro201Gln |
| Pro201Glu |
| Pro201Gly |
| Pro201Ser |
| Gly202Asn |
| Gly202Asp |
| Gly202Gln |
| Gly202Glu |
| Gly202Pro |
| Gly202Ser |
| Val203Asn |
| Val203Asp |
| Val203Cys |
| Val203Gln |
| Val203Glu |
| Val203Gly |
| Val203His |
| Val203Met |
| Val203Pro |
| Val203Ser |
| Ser204Glu |
| Ile205Ala |
| Ile205Asn |
| Ile205Asp |
| Ile205Cys |
| Ile205Gln |
| Ile205Glu |
| Ile205Gly |
| Ile205His |
| Ile205Leu |
| Ile205Met |
| Ile205Pro |
| Ile205Ser |
| Ile205Thr |
| Gln206Asn |
| Gln206Pro |
| Gln206Ser |

TABLE 2-continued

Single Mutation BPN' Variants

Ser207Asp
Ser207Glu
Thr208Asn
Thr208Gln
Thr208Gly
Thr208Pro
Thr208Ser
Leu209Ala
Leu209Asn
Leu209Asp
Leu209Cys
Leu209Gln
Leu209Glu
Leu209Gly
Leu209His
Leu209Ile
Leu209Met
Leu209Pro
Leu209Ser
Leu209Thr
Leu209Val
Pro210Asn
Pro210Asp
Pro210Gln
Pro210Glu
Pro210Gly
Pro210Ser
Gly211Ala
Gly211Asn
Gly211Asp
Gly211Gln
Gly211Glu
Gly211Pro
Gly211Ser
Asn212Asp
Asn212Gln
Asn212Glu
Asn212Ser
Lys213Asp
Lys213Glu
Lys213Trp
Lys213Phe
Lys213Tyr
Lys213Leu
Lys213Ile
Lys213Val
Lys213Met
Lys213Cys
Lys213Ala
Lys213His
Lys213Pro
Lys213Gly
Lys213Gln
Lys213Asn
Lys213Ser
Tyr214Phe
Tyr214Ala
Tyr214Asn
Tyr214Cys
Tyr214Gln
Tyr214Gly
Tyr214His
Tyr214Ile
Tyr214Leu
Tyr214Met
Tyr214Pro
Tyr214Val
Gly215Thr
Gly215Asn
Gly215Asp
Gly215Gln
Gly215Glu
Gly215Pro
Gly215Ser
Ala216Asn
Ala216Asp
Ala216Gln

TABLE 2-continued

Single Mutation BPN' Variants

Ala216Glu
Ala216Gly
Ala216His
Ala216Pro
Ala216Ser
Ala216Thr
Asn218Glu
Gly219Asn
Gly219Asp
Gly219Gln
Gly219Glu
Gly219Pro
Gly219Ser
Thr220Asn
Thr220Asp
Thr220Gln
Thr220Glu
Thr220Gly
Thr220Pro

TABLE 3

Double Mutation BPN' Variants

Gln206Ser + Lys213Glu
Ile205Gly + Asn212Glu
Leu209Asn + Thr220Gln
Ile205Leu + Asn218Gln
Ala216Gly + Thr220Pro
Thr208Asn + Ala216Thr
Gly211Gln + Lys213Glu
Tyr217Pro + Gly219Glu
Ile205Gly + Lys213Glu
Pro210Asn + Gly215Gln
Val203Glu + Pro210Gln
Gly202Gln + Leu209Gln
Thr208Pro + Gly219Asp
Ala200His + Pro210Glu
Lys213Asp + Asn218Ser
Tyr214Ser + Thr220Gln
Leu209Cys + Gly219Glu
Val203Asp + Leu209Gln
Val203Asp + Leu209Val
Gln206Ser + Pro210Glu
Gly202Gln + Gln206Asn
Ala200Asn + Gly219Gln
Gly202Asn + Tyr217His
Ala200Gln + Leu209Asn
Gln206Ser + Leu209Gln
Asn212Asp + Tyr214Asn
Gly202Ser + Ser204Glu
Leu209Gln + Gly219Gln
Gly202Gln + Pro210Glu
Ala200Pro + Ser204Asp
Pro210Gly + Thr220Gly
Pro201Ser + Gln206Glu
Val203His + Tyr214Ile
Ala200Gln + Val203His
Gly211Pro + Gly215Ser
Ile205Gly + Tyr214Leu
Pro201Asn + Lys213Asp
Ala200Asn + Ala216Asp
Pro201Gln + Gly202Ser
Ser204Glu + Gln206Ser
Val203Pro + Pro210Glu
Gly215Pro + Thr220Glu
Thr208Ser + Ala216Gly
Ser204Asp + Leu209Thr
Asn212Asp + Tyr217Pro
Val203Gln + Tyr214Glu
Gln206Asn + Lys213Glu
Ile205Gln + Tyr217Cys
Gln206Ser + Gly219Asp
Tyr214Gly + Asn218Asp

TABLE 3-continued

Double Mutation BPN' Variants

Val203Glu + Gly219Gln
Ile205Gly + Asn218Asp
Gly211Ser + Tyr214Glu
Pro201Ser + Gly215Pro
Pro201Asn + Asn218Asp
Ala216His + Thr220Glu
Gln206Asp + Thr208Gln
Ser204Asp + Ala216Gly
Val203Pro + Ala216Ser
Asn212Gln + Lys213Asp
Gly215Asp + Ala216Pro
Ala200Ser + Gly202Pro
Thr208Gly + Lys213Asp
Ala216Pro + Thr220Gly
Pro201Gln + Tyr214Gln
Gln206Asp + Tyr214Ser
Gln206Ser + Gly211Ser
Lys213Asp + Gly215Pro
Ser204Glu + Ala216Gln
Gly202Asn + Asn212Asp
Pro201Asn + Leu209Thr
Gly211Ser + Ala216Gln
Gly202Gln + Gly219Asp
Gln206Ser + Tyr217Ala
Gly215Asn + Asn218Glu
Gly211Ser + Ala216Glu
Ser204Asp + Gln206Ser
Ile205Thr + Gly211Glu
Ala200Pro + Ile205Pro
Thr208Pro + Leu209Ala
Ala200Gln + Gly215Ser
Ile205Ala + Gln206Glu
Leu209Val + Lys213Asp
Pro201Ser + Val203Thr
Ala200Pro + Lys213Asp
Pro201Ser + Ser204Glu
Thr208Asn + Thr220Glu
Gln206Ser + Tyr217Asp
Leu209Cys + Tyr214Glu
Val203Thr + Asn218Glu
Ala200Asn + Val203Asp
Pro201Gln + Lys213Glu
Gly202Pro + Gly211Glu
Thr208Gly + Thr220Pro
Ala200Pro + Tyr217Leu
Gly211Asp + Thr220Pro
Pro210Asn + Asn212Asp
Thr208Gln + Gly211Asn
Gly202Pro + Gly211Gln
Gly202Asn + Ile205Asn
Gly202Pro + Asn218Ser
Ala200Pro + Ile205Gln
Pro201Gln + Gly215Asp
Ala200Gly + Lys213Asp
Ala216Thr + Tyr217Asn
Gly211Asn + Gly219Glu
Thr208Ser + Tyr217Ile
Gly202Gln + Val203Ala
Ala200Gly + Gln206Asp
Pro210Glu + Ala216Asn
Pro201Asn + Gly215Asn
Gly202Pro + Ala216Pro
Thr208Gly + Ala216His
Ala200Pro + Ile205His
Leu209Cys + Lys213Asp
Val203Thr + Thr208Pro
Tyr214Val + Gly219Asp
Leu209His + Lys213Asp
Val203Thr + Ile205Thr
Tyr214Pro + Gly215Pro
Val203Pro + Thr220Asp
Asn212Glu + Gly219Ser
Gln206Ser + Asn212Glu
Gly202Asn + Gly215Asp
Tyr214Met + Tyr217Gln
Asn218Glu + Thr220Asn
Ala216Ser + Thr220Asn

TABLE 3-continued

Double Mutation BPN' Variants

Thr208Gly + Asn218Asp
Leu209Met + Ala216Asp
Pro210Glu + Tyr217Gln
Ser204Glu + Ala216Asn
Gly211Asn + Gly215Asp
Val203Cys + Ala216Ser
Tyr214Ala + Tyr217Asp
Tyr217His + Asn218Asp
Thr208Gly + Gly219Glu
Ala200His + Gln206Asp
Asn212Ser + Tyr217Ile
Val203Gln + Asn212Glu
Pro201Gly + Tyr214Ser
Gly211Gln + Tyr217Leu
Pro201Asn + Pro210Glu
Asn212Asp + Tyr217Ser
Ala200Asn + Asn218Asp
Gly211Asn + Thr220Asp
Gln206Asp + Thr220Pro
Ser204Asp + Ile205Gly
Val203Ser + Tyr217Gly
Gly202Asn + Tyr217Leu
Gly215Pro + Gly219Asn
Gln206Glu + Gly215Gln
Gly202Ser: + Thr208Asn
Pro210Glu + Gly211Pro
Gly219Pro + Thr220Asp
Val203Met + Thr220Ser
Ala200Ser + Gly211Pro
Ala200Gly + Gln206Glu
Ala216Pro + Thr220Pro
Ile205Met + Gly211Asp
Ala200Gly + Thr220Asp
Ile205Asn + Pro210Glu
Gln206Asp + Asn218Ser
Pro201Gly + Pro210Glu
Ala200HiS + Val203Gln
Gly211Asp + Ala216Ser
Val203Ser + Asn218Glu
Ser204Glu + Thr220Ser
Thr208Gln + Tyr214His
Ile205Pro + Pro210Asp
Leu209Thr + Pro210Asn
Gln206Asp + Gly215Asn
Ala200His + Tyr217Asn
Tyr217Ala + Asn218Asp
Tyr214Ile + Thr220Asp
Ala200Ser + Gly215Pro
Pro210Glu + Tyr214Leu
Leu209Pro + Asn212Glu
Thr208Asn + Gly211Asp
Ala200Gly + Tyr214Asn
Ser204Asp + Gly215Gln

TABLE 4

Triple Mutation BPN' Variants

| | | |
|---|---|---|
| Gln206Glu + | Pro210Asn + | Gly215Gln |
| Thr208Pro + | Leu209Gln + | Gly219Asp |
| Pro201Asn + | Lys213Asp + | Asn218Ser |
| Thr208Asn + | Leu209Cys + | Thr220Asn |
| Ile205Thr + | Gln206Ser + | Pro210Glu |
| Gly202Ser + | Thr208Gln + | Gly215Gln |
| Gln206Asp + | Leu209Pro + | Gly219Pro |
| Ala200Thr + | Val203Cys + | Asn212Asp |
| Ala200His + | Leu209Ile + | Pro210Asn |
| Ser204Asp + | Gly211Ser + | Gly219Gln |
| Val203Gly + | Lys213Asp + | Tyr214His |
| Gly202Asn + | Gly211Asp + | Asn212Ser |
| Tyr214Ser + | Tyr217Met + | Asn218Asp |
| Ala200Gly + | Asn212Asp + | Tyr214His |
| Ala200Asn + | Gly219Gln + | Thr220Glu |
| Ala200Gln + | Ser204Glu + | Leu209Ile |

TABLE 4-continued

Triple Mutation BPN' Variants

| | | | | | |
|---|---|---|---|---|---|
| Gly202Ser | + Gln206Ser | + Thr220Pro | Ile205Val | + Asn218Ser | + Gly219Ser |
| Pro210Asn | + Asn212Ser | + Asn218Glu | Gly202Gln | + Ser204Glu | + Asn212Gln |
| Tyr214Ser | + Ala216Pro | + Asn218Gln | Gly202Gln | + Ile205Met | + Lys213Glu |
| Val203Met | + Ile205Ser | + Ala216Gln | Ser204Asp | + Leu209Ile | + Gly219Gln |
| Leu209Met | + Lys213Glu | + Tyr214His | Leu209Met | + Gly211Asn | + Gly219Glu |
| Gly202Asn | + Tyr214Met | + Ala216Pro | Pro201Gly | + Ile205His | + Thr220Asp |
| Leu209Ala | + Asn212Glu | + Thr220Gly | Asn212Gln | + Gly215Ser | + Thr222Gln |
| Ile205Pro | + Ala216His | + Asn218Asp | Ala200Asn | + Gly211Pro | + Lys213Glu |
| Pro210Gly | + Ala216Pro | + Tyr217Ala | Gly211Ser | + Asn212Glu | + Asn218Ser |
| Val203Pro | + Pro210Gln | + Tyr217Asp | Pro210Gln | + Asn212Asp | + Tyr214Leu |
| Pro201Asn | + Asn212Asp | + Gly215Gln | Gly202Asn | + Lys213Asp | + Tyr217Gln |
| Pro201Ser | + Gly202Ser | + Ile205Leu | Ala200Gly | + Ser204Asp | + Gly215Pro |
| Pro201Ser | + Val203Gly | + Thr220Ser | Gly202Ser | + Ser204Asp | + Leu209Gln |
| Gly202Gln | + Pro210Gly | + Gly211Pro | Ala200Gln | + Val203Thr | + Ile205Ser |
| Ser204Glu | + Ile205Cys | + Thr208Ser | Val203Ser | + Gly215Ser | + Gly219Asp |
| Ile205Cys | + Thr208Asn | + Tyr214Cys | Gly202Pro | + Val203Asp | + Tyr217Pro |
| Leu209Cys | + Pro210Asn | + Tyr217Leu | Ala200Asn | + Tyr217Ser | + Thr220Asp |
| Leu209Gln | + Gly211Gln | + Asn212Ser | Ala200Ser | + Gln206Asp | + Gly215Asn |
| Leu209Pro | + Tyr214Pro | + Asn218Glu | Val203Pro | + Ser204Asp | + Leu209His |
| Ala200Pro | + Pro201Asn | + Ala216Pro | Pro201Ser | + Gln206Asp | + Gly215Asn |
| Val203His | + Ser204Glu | + Leu209Val | Ala200Pro | + Ser204Asp | + Ile205Pro |
| Gln206Ser | + Thr208Pro | + Gly211Asn | Val203Met | + Tyr214Cys | + Thr220Asn |
| Pro201Gly | + Gly202Ser | + Leu209Ala | Thr208Gln | + Lys213Asp | + Tyr214Thr |
| Pro201Gln | + Leu209Cys | + Asn212Ser | Ile205Val | + Gln206Ser | + Lys213Asp |
| Gln206Asn | + Leu209His | + Tyr217Gln | Ala200Gly | + Val203His | + Gly211Glu |
| Pro210Ser | + Asn212Asp | + Tyr217His | Val203Thr | + Ile205His | + Asn212Asp |
| Gly202Ser | + Tyr214Thr | + Asn218Ser | Pro201Ser | + Tyr214Val | + Ala216Thr |
| Ala200Ser | + Leu209Gln | + Pro210Asp | Ile205Thr | + Tyr217Pro | + Gly219Asp |
| Gly202Ser | + Ser204Asp | + Thr220Gln | Thr208Asn | + Ala216Glu | + Asn218Ser |
| Val203Met | + Thr208Asn | + Gly219Asp | Val203Glu | + Ile205Ser | + Leu209Ser |
| Ala200Asn | + Asn212Asp | + Tyr214Ser | Ala200Ser | + Ile205Met | + Gln206Ser |
| Gly202Gln | + Gly215Asn | + Thr220Glu | Ala200Thr | + Pro210Gly | + Asn218Ser |
| Tyr217Ala | + Asn218Asp | + Thr220Gly | Thr208Gln | + Lys213Asp | + Tyr214His |
| Ala200Ser | + Gly202Gln | + Ser204Asp | Gly202Pro | + Thr208Pro | + Lys213Asp |
| Thr208Asn | + Gly219Asn | + Thr220Ser | Ala200Pro | + Gln206Asp | + Thr220Gly |
| Thr208Gly | + Gly211Glu | + Asn218Ser | Gln206Glu | + Leu209Val | + Gly219Gln |
| Gly202Pro | + Leu209Met | + Tyr217Glu | Asn218Glu | + Gly219Gln | + Thr220Pro |
| Pro201Gly | + Tyr217Ile | + Asn218Glu | Gly211Asn | + Tyr217Asp | + Thr220Asn |
| Val203His | + Gly215Asp | + Tyr217His | Ser204Asp | + Leu209Gly | + Gly211Ser |
| Ile205Gly | + Gln206Asn | + Thr220Asp | Pro201Ser | + Thr208Gly | + Leu209Ser |
| Ile205Leu | + Gln206Asp | + Tyr214Val | Thr208Asn | + Tyr214Ile | + Gly215Pro |
| Gln206Glu | + Gly215Pro | + Gly219Asn | Leu209Pro | + Gly211Glu | + Gly219Pro |
| Pro201Asn | + Thr208Gly | + Ala216Ser | Ala200Pro | + Pro201Ser | + Thr220Gln |
| Gly202Ser | + Thr208Asn | + Thr220Asp | Val203Asn | + Thr208Gly | + Leu209Gln |
| Ala200His | + Pro201Gly | + Leu209Gln | Pro210Ser | + Asn212Glu | + Gly215Gln |
| Ile205Ala | + Leu209Ala | + Asn218Asp | Pro201Asn | + Gln206Glu | + Pro210Gly |
| Gly202Gln | + Tyr214Asp | + Asn218Ser | Pro201Gly | + Gly211Gln | + Lys213Glu |
| Ile205Met | + Asn212Glu | + Tyr214Gly | Pro201Ser | + Gly202Gln | + Val203Asn |
| Pro201Ser | + Gly202Gln | + Asn218Glu | Pro201Gln | + Val203Cys | + Lys213Asp |
| Ser204Glu | + Thr208Gln | + Tyr214His | Val203Asn | + Gly215Glu | + Tyr217Gly |
| Gln206Asp | + Gly215Asn | + Tyr217Asn | Ala200Gln | + Gly211Asn | + Ala216Asn |
| Tyr217Ala | + Asn218Asp | + Gly219Asn | Gly202Ser | + Asn212Glu | + Gly219Asn |
| Ala200Ser | + Lys213Asp | + Gly215Pro | Gly215Glu | + Ala216His | + Tyr217Ile |
| Leu209Pro | + Asn212Glu | + Tyr214Leu | Gly211Asp | + Tyr214Met | + Gly219Pro |
| Ala200Gly | + Tyr214Asn | + Tyr217Ile | Ala200Gln | + Ser204Glu | + Ile205Ser |
| Ser204Asp | + Gly215Gln | + Ala216Gln | Pro201Ser | + Gly202Gln | + Lys213Asp |
| Ala200Gly | + Ile205Gln | + Gly215Asp | Ala200Gly | + Gly211Ser | + Tyr217Glu |
| Ala200Gly | + Tyr214Cys | + Thr220Pro | Pro201Gly | + Thr208Pro | + Ala216Ser |
| Ala200Gly | + Leu209Gln | + Lys213Glu | Gly202Pro | + Ser204Asp | + Ile205Gln |
| Gln206Asn | + Gly215Pro | + Thr220Asp | Pro201Ser | + Ile205Ser | + Thr208Gln |
| Ile205Pro | + Gly215Asp | + Ala216Pr | Pro201Asn | + Asn212Gln | + Tyr214Asn |
| Ser204Glu | + Ile205Val | + Pro210Gly | Ala200Thr | + Val203Pro | + Asn212Asp |
| Pro201Asn | + Gly202Gln | + Gly211Gln | Pro201Asn | + Val203Met | + Thr220Asn |
| Pro201Gly | + Ile205Cys | + Gly219Asp | Gly202Gln | + Pro210Asp | + Tyr214Gln |
| Pro201Asn | + Pro210Asn | + Lys213Glu | Pro201Gly | + Tyr214Ala | + Gly215Gln |
| Gly202Ser | + Val203Glu | + Leu209Gly | Pro201Ser | + Asn212Glu | + Ala216Gln |
| Pro201Gly | + Val203His | + Leu209Pro | Val203Thr | + Tyr217Gln | + Gly219Asp |
| Ala200Ser | + Tyr214Glu | + Thr220Gln | Thr208Gln | + Pro210Ser | + Tyr214Ile |
| Gly202Gln | + Leu209Ile | + Asn219Asp | Val203Ser | + Ile205Thr | + Ala216His |
| Ala200Asn | + Gly215Asp | + Gly219Pro | Gln206Asp | + Thr208Gly | + Gly219Asn |
| Gly202Pro | + Ser204Asp | + Thr208Gly | Pro201Asn | + Gly211Glu | + Asn212Gln |
| Val203His | + Gly211Ser | + Tyr217Gln | Thr208Asn | + Lys213Glu | + Tyr217Ser |
| Ala200Gln | + Gln206Asp | + Asn212Gln | Gln206Asn | + Gly215Asp | + Ala216Asp |
| Thr208Gln | + Gly211Ser | + Gly215Asn | Val203Met | + Pro210Asp | + Gly211Glu |
| Ala200Thr | + Gly202Gln | + Ala216His | Ala200Asn | + Pro210Asp | + Gly211Glu |
| Val203Gly | + Gln206Glu | + Leu209Ser | Leu209Gln | + Pro210Asp | + Gly211Glu |
| Leu209Thr | + Asn218Gln | + Gly219Glu | Val203His | + Pro210Glu | + Gly211Glu |

TABLE 4-continued

Triple Mutation BPN' Variants

| | | | | | |
|---|---|---|---|---|---|
| Pro210Asp | + | Gly211Asp | + | Ala216His | |
| Leu209Ala | + | Asn218Glu | + | Gly219Asp | |
| Ile205Cys | + | Tyr217Glu | + | Asn218Glu | |
| Ala200Gly | + | Gly219Glu | + | Thr220Asp | |
| Leu209Cys | + | Asn212Asp | + | Lys213Glu | |
| Thr208Gln | + | Asn212Glu | + | Lys213Glu | |
| Pro201Gln | + | Asn212Asp | + | Lys213Asp | |
| Ile205Asn | + | Ala216Glu | + | Tyr217Asp | |
| Ala200His | + | Gln206Glu | + | Ala216Glu | |
| Gln206Glu | + | Ala216Asp | + | Tyr217Glu | |

TABLE 5

Quadruple Mutation BPN' Variants

| | | | | | | | |
|---|---|---|---|---|---|---|---|
| Pro201Gly | + | Ile205Ser | + | Tyr217Leu | + | Thr220Pro |
| Ala200Thr | + | Thr208Gln | + | Lys213Asp | + | Tyr217Leu |
| Leu209Asn | + | Gly211Glu | + | Tyr217Leu | + | Asn218Gln |
| Pro201Ser | + | Thr208Ser | + | Tyr217Leu | + | Asn218Ser |
| Val203His | + | Leu209Val | + | Lys213Glu | + | Tyr217Leu |
| Ala200Gly | + | Pro201Asn | + | Gly211Ser | + | Tyr217Leu |
| Pro201Gly | + | Gln206Ser | + | Tyr217Leu | + | Gly219Pro |
| Gly202Ser | + | Gln206Glu | + | Thr208Asn | + | Tyr217Leu |
| Pro210Gln | + | Tyr214Leu | + | Tyr217Leu | + | Gly219Gln |
| Leu209Cys | + | Asn212Gln | + | Lys213Asp | + | Tyr217Leu |
| Gly202Asn | + | Ser204Glu | + | Asn212Gln | + | Tyr217Gly |
| Gly202Asn | + | Tyr214Ser | + | Ala216Gly | + | Tyr217Leu |
| Pro210Asp | + | Gly211Ser | + | Tyr217Leu | + | Thr220Gln |
| Gly202Pro | + | Ile205Leu | + | Gly215Ser | + | Tyr217Leu |
| Thr208Ser | + | Pro210Ser | + | Ala216Gln | + | Tyr217Leu |
| Pro201Gly | + | Ser204Glu | + | Tyr214Gln | + | Tyr217His |
| Ala200Thr | + | Pro201Gly | + | Tyr217Leu | + | Asn218Asp |
| Ala216Gln | + | Tyr217Leu | + | Asn218Asp | + | Thr220Gln |
| Ala200Pro | + | Ser204Asp | + | Tyr214His | + | Tyr217Leu |
| Ala200His | + | Ile205Ser | + | Asn212Gln | + | Tyr217Leu |
| Leu209Ser | + | Ala216His | + | Tyr217Leu | + | Thr220Asn |
| Ile205Thr | + | Lys213Asp | + | Gly215Ser | + | Tyr217Leu |
| Gln206Asn | + | Leu209Met | + | Tyr217Leu | + | Asn218Glu |
| Ala200Thr | + | Gly215Asn | + | Tyr217Leu | + | Thr220Asn |
| Pro201Gly | + | Val203Ala | + | Asn212Ser | + | Tyr217Leu |
| Ala200His | + | Leu209Ser | + | Pro210Glu | + | Tyr217Leu |
| Ser204Glu | + | Gln206Ser | + | Tyr217Leu | + | Thr220Asn |
| Asn212Asp | + | Tyr214His | + | Gly215Pro | + | Tyr217Leu |
| Gly202Pro | + | Val203Cys | + | Thr208Gly | + | Tyr217Leu |
| Gly202Gln | + | Tyr214Gln | + | Ala216Ser | + | Tyr217Leu |
| Gly202Ser | + | Ser204Glu | + | Thr208Gly | + | Tyr217Leu |
| Gly202Pro | + | Thr208Gly | + | Lys213Glu | + | Tyr217Leu |
| Thr208Gly | + | Leu209Ile | + | Gly215Glu | + | Tyr217Leu |
| Ala200Ser | + | Gly202Gln | + | Tyr217Leu | + | Gly219Asn |
| Thr208Ser | + | Gly211Ser | + | Ala216Thr | + | Tyr217Leu |
| Val203Thr | + | Leu209Val | + | Ala216Pro | + | Tyr217Leu |
| Thr208Pro | + | Gly211Pro | + | Tyr217Leu | + | Gly219Pro |
| Ala200Gly | + | Gly202Ser | + | Tyr217Leu | + | Thr220Gly |
| Pro201Ser | + | Ile205Pro | + | Tyr217Leu | + | Asn218Glu |
| Leu209Gly | + | Pro210Asn | + | Gly215Glu | + | Tyr217Pro |
| Ala200Pro | + | Gly215Gln | + | Ala216Asp | + | Tyr217Leu |
| Pro201Gln | + | Thr208Ser | + | Gly215Ser | + | Tyr217Leu |
| Ala200Pro | + | Leu209Thr | + | Asn212Gln | + | Tyr217Asn |
| Val203Pro | + | Thr208Gln | + | Tyr217Leu | + | Gly219Ser |
| Leu209Cys | + | Pro210Gly | + | Gly215Glu | + | Tyr217Leu |
| Ala200His | + | Ser204Asp | + | Leu209Cys | + | Tyr217Leu |
| Ile205Val | + | Ala216Glu | + | Tyr217Leu | + | Gly219Pro |
| Ala200Gln | + | Val203Ser | + | Gly215Asp | + | Tyr217Leu |
| Leu209His | + | Ala216Pro | + | Tyr217Leu | + | Asn218Asp |
| Gly202Pro | + | Leu209Thr | + | Tyr217Leu | + | Asn218Asp |
| Pro201Asn | + | Lys213Glu | + | Tyr217Leu | + | Asn218Gln |
| Pro201Asn | + | Gln206Glu | + | Ala216Asn | + | Tyr217Leu |
| Val203Asp | + | Ile205Cys | + | Tyr217Gln | + | Thr220Gln |
| Gly202Ser | + | Tyr214Pro | + | Tyr217Leu | + | Gly219Glu |
| Tyr214Ile | + | Gly215Asp | + | Ala216Gly | + | Tyr217Leu |
| Gly202Pro | + | Gly215Pro | + | Tyr217Leu | + | Asn218Ser |
| Gly202Pro | + | Val203Asp | + | Leu209Ser | + | Tyr217Ala |
| Ala200Pro | + | Leu209Met | + | Tyr217Leu | + | Gly219Asp |
| Tyr214Ser | + | Gly215Gln | + | Tyr217Met | + | Gly219Glu |

TABLE 5-continued

Quadruple Mutation BPN' Variants

| | | | | | | | |
|---|---|---|---|---|---|---|---|
| Ala200Ser | + | Ala216His | + | Tyr217Leu | + | Gly219Asp |
| Gly202Gln | + | Val203Asp | + | Tyr217Leu | + | Thr220Asn |
| Val203Ala | + | Gln206Glu | + | Gly215Gln | + | Tyr217Leu |
| Ala200Pro | + | Thr208Ser | + | Tyr217Leu | + | Gly219Asp |
| Ala200Pro | + | Gly211Pro | + | Tyr217Leu | + | Thr220Asp |
| Thr208Pro | + | Leu209Ala | + | Tyr217Leu | + | Asn218Ser |
| Thr208Gly | + | Tyr214His | + | Tyr217Leu | + | Gly219Ser |
| Gly202Asn | + | Ser204Glu | + | Tyr217Met | + | Gly219Asn |
| Gln206Ser | + | Leu209His | + | Pro210Glu | + | Tyr217Pro |
| Ala200Ser | + | Tyr214Thr | + | Ala216Asn | + | Tyr217Leu |
| Pro201Ser | + | Ser204Glu | + | Asn212Ser | + | Tyr217Gln |
| Ala200His | + | Ile205Leu | + | Tyr217Leu | + | Asn218Gln |
| Val203Ala | + | Lys213Asp | + | Tyr217Leu | + | Gly219Pro |
| Pro201Gly | + | Gln206Asn | + | Tyr217Leu | + | Thr220Glu |
| Ser204Glu | + | Gly211Gln | + | Tyr217Leu | + | Asn218Ser |
| Pro201Gly | + | Leu209Asn | + | Pro210Gln | + | Tyr217Leu |
| Pro201Gln | + | Asn212Asp | + | Tyr217Ala | + | Gly219Gln |
| Ile205Asn | + | Gln206Asp | + | Thr208Asn | + | Tyr217Leu |
| Ser204Asp | + | Ile205Leu | + | Tyr214Ile | + | Tyr217Leu |
| Gly215Asn | + | Tyr217Leu | + | Gly219Glu | + | Thr220Gln |
| Ile205His | + | Leu209Ser | + | Lys213Glu | + | Tyr217Leu |
| Pro201Ser | + | Ile205His | + | Tyr217Leu | + | Asn218Glu |
| Gly202Ser | + | Gly211Glu | + | Asn212Ser | + | Tyr217Leu |
| Gly202Asn | + | Val203Cys | + | Thr208Ser | + | Tyr217Thr |
| Pro201Gln | + | Pro210Glu | + | Gly215Pro | + | Tyr217Leu |
| Thr208Gln | + | Gly211Pro | + | Lys213Glu | + | Tyr217Leu |
| Thr208Gln | + | Ala216Glu | + | Tyr217Leu | + | Thr220Pro |
| Pro201Gly | + | Gly202Asn | + | Tyr217Leu | + | Gly219Glu |
| Val203Ala | + | Thr208Asn | + | Asn212Gln | + | Tyr217Leu |
| Gly202Ser | + | Val203Met | + | Pro210Asp | + | Tyr217Leu |
| Val203Ala | + | Asn212Asp | + | Tyr217Leu | + | Thr220Gln |
| Thr208Gly | + | Leu209Ile | + | Tyr217Leu | + | Asn218Gln |
| Pro201Gln | + | Ile205Asn | + | Thr208Asn | + | Tyr217Leu |
| Val203His | + | Ile205Asn | + | Tyr217Leu | + | Asn218Glu |
| Val203Met | + | Thr208Pro | + | Tyr217Leu | + | Thr220Glu |
| Ile205Asn | + | Pro210Gly | + | Tyr217Leu | + | Thr220Gly |
| Thr208Gln | + | Gly211Asp | + | Tyr214Thr | + | Tyr217Leu |
| Pro201Gln | + | Leu209Cys | + | Tyr214Ala | + | Tyr217Leu |
| Pro201Gln | + | Ile205Gly | + | Gln206Glu | + | Tyr217Leu |
| Gly202Gln | + | Thr208Gly | + | Gly215Glu | + | Tyr217Leu |
| Leu209Pro | + | Asn212Asp | + | Ala216Gln | + | Tyr217Val |
| Gly202Ser | + | Lys213Gln | + | Tyr214Gln | + | Tyr217Leu |
| Ser204Asp | + | Thr208Gly | + | Tyr214Cys | + | Tyr217Leu |
| Gln206Ser | + | Thr208Gln | + | Gly211Asp | + | Tyr217Leu |
| Ala200Gln | + | Pro201Ser | + | Pro210Asp | + | Tyr217Leu |
| Thr208Gln | + | Tyr217Leu | + | Asn218Ser | + | Gly219Gln |
| Pro210Asn | + | Tyr214Ile | + | Tyr217Leu | + | Thr220Gly |
| Tyr214Gln | + | Ala216Asn | + | Tyr217Leu | + | Asn218Gln |
| Val203Ala | + | Thr208Asn | + | Lys213Glu | + | Tyr217Leu |
| Gly202Gln | + | Ser204Glu | + | Asn212Gln | + | Tyr217Asn |
| Pro201Gly | + | Ser204Glu | + | Gly215Pro | + | Tyr217Gly |
| Ala200Ser | + | Gly202Ser | + | Asn212Gln | + | Tyr217Leu |
| Gln206Ser | + | Gly211Glu | + | Tyr214Asn | + | Tyr217Gln |
| Gly202Asn | + | Val203Gly | + | Thr208Gly | + | Tyr217His |
| Ala200His | + | Asn212Gln | + | Lys213Asp | + | Tyr217Leu |
| Ala200Ser | + | Ile205Gln | + | Gln206Ser | + | Tyr217Leu |
| Gln206Asn | + | Leu209Val | + | Tyr217Leu | + | Gly219Gln |
| Thr208Pro | + | Pro210Ser | + | Lys213Asp | + | Tyr217Leu |
| Val203Ala | + | Tyr217Leu | + | Gly219Asp | + | Thr220Asn |
| Ser204Asp | + | Gly215Asn | + | Tyr217His | + | Thr220Asn |
| Ile205Leu | + | Gln206Asn | + | Thr208Gly | + | Tyr217Leu |
| Gly202Pro | + | Ile205Thr | + | Tyr214Ser | + | Tyr217Leu |
| Ile205Asn | + | Asn212Gln | + | Tyr214His | + | Tyr217Leu |
| Gly202Ser | + | Ile205His | + | Lys213Asp | + | Tyr217Leu |
| Val203Cys | + | Leu209Asn | + | Tyr214Gly | + | Tyr217Leu |
| Gly202Asn | + | Val203Pro | + | Gly211Asp | + | Tyr217Leu |
| Ala200Pro | + | Asn212Gln | + | Gly215Pro | + | Tyr217Leu |
| Gly202Ser | + | Val203His | + | Tyr214Ser | + | Tyr217Leu |
| Ala200Asn | + | Gly202Ser | + | Val203Pro | + | Tyr217Leu |
| Ala200Asn | + | Val203Gln | + | Tyr217Leu | + | Gly219Asn |
| Ala200Gln | + | Thr208Gln | + | Gly211Asn | + | Tyr217Leu |
| Leu209Ser | + | Gly215Pro | + | Tyr217Leu | + | Gly219Ser |
| Ala200Gly | + | Gln206Asp | + | Pro210Gly | + | Tyr217Leu |
| Ala200Ser | + | Gly202Asn | + | Ala216Gln | + | Tyr217Leu |
| Ile205Cys | + | Thr208Pro | + | Tyr214Ser | + | Tyr217Leu |
| Ala200Asn | + | Val203Gly | + | Asn212Asp | + | Tyr217Leu |
| Pro201Gly | + | Gly202Ser | + | Ala216Gln | + | Tyr217Leu |

TABLE 5-continued

Quadruple Mutation BPN' Variants

| | | | |
|---|---|---|---|
| Pro201Gln | + Pro210Asp | + Ala216Gly | + Tyr217Leu |
| Val203Gln | + Asn212Ser | + Tyr217Leu | + Thr220Asn |
| Gly202Ser | + Leu209Ile | + Gly211Glu | + Tyr217Leu |
| Thr208Gly | + Gly211Asp | + Gly215Pro | + Tyr217Ala |
| Pro201Asn | + Gly202Gln | + Lys213Asp | + Tyr217Leu |
| Pro201Asn | + Val203Asp | + Ile205Gln | + Tyr217Leu |
| Thr208Gln | + Tyr217Leu | + Gly219Pro | + Thr220Asn |
| Ala200Ser | + Thr208Gln | + Leu209Cys | + Tyr217Ile |
| Pro201Ser | + Gly202Asn | + Gly215Glu | + Tyr217Leu |
| Val203Met | + Gln206Asp | + Leu209Thr | + Tyr217Cys |
| Pro201Asn | + Gly215Asp | + Tyr217Leu | + Gly219Asn |
| Ile205Gly | + Asn212Asp | + Tyr217Leu | + Asn218Gln |
| Ile205Asn | + Pro210Ser | + Tyr217Leu | + Gly219Gln |
| Gly202Gln | + Leu209Ser | + Tyr217Leu | + Thr220Asp |
| Ile205Ser | + Thr208Ser | + Tyr217Pro | + Thr220Glu |
| Ser204Glu | + Asn212Ser | + Tyr217Leu | + Gly219Asn |
| Gly202Asn | + Thr208Pro | + Asn212Gln | + Tyr217Leu |
| Pro201Asn | + Gly202Pro | + Tyr217Leu | + Thr220Gln |
| Thr208Asn | + Tyr214Met | + Tyr217Leu | + Gly219Glu |
| Ala200Pro | + Ser204Asp | + Gly215Ser | + Tyr217Leu |
| Ile205Ala | + Gln206Glu | + Leu209Gly | + Tyr217Leu |
| Val203Met | + Ile205Gly | + Gly211Ser | + Tyr217Leu |
| Ala200Asn | + Lys213Asp | + Tyr214Gln | + Tyr217Leu |
| Ala200Gly | + Pro210Gly | + Ala216Asp | + Tyr217Leu |
| Ala200Gly | + Gln206Asp | + Tyr214Val | + Tyr217Ser |
| Leu209Val | + Pro210Gln | + Tyr217Leu | + Gly219Gln |
| Thr208Gln | + Asn212Ser | + Tyr217Leu | + Thr220Asp |
| Gly202Pro | + Ala216Gly | + Tyr217Glu | + Gly219Gln |
| Gly202Gln | + Gly211Pro | + Tyr217Leu | + Asn218Gln |
| Ala200Thr | + Thr208Gln | + Gly215Gln | + Tyr217Leu |
| Ala200Ser | + Pro201Gln | + Gly202Leu | + Tyr217Leu |
| Ala200His | + Tyr214Cys | + Ala216Glu | + Tyr217Leu |
| Ser204Asp | + Leu209Gly | + Gly211Gln | + Tyr217Leu |
| Ala200Gly | + Gln206Ser | + Thr208Pro | + Tyr217Cys |
| Gly202Ser | + Ser204Glu | + Leu209Thr | + Tyr217Leu |
| Ala200His | + Leu209Ala | + Ala216Asp | + Tyr217Leu |
| Pro210Glu | + Tyr214Ile | + Tyr217Leu | + Thr220Gln |
| Gln206Ser | + Thr208Pro | + Tyr217Leu | + Thr220Pro |
| Gly202Asn | + Leu209Val | + Tyr217Ala | + Gly219Asp |
| Ile205Cys | + Gly211Asn | + Ala216Gly | + Tyr217Leu |
| Ala200Pro | + Val203His | + Tyr217Leu | + Thr220Asp |
| Pro201Asn | + Val203Ala | + Tyr214Glu | + Tyr217Leu |
| Asn212Glu | + Lys213Glu | + Ala216Thr | + Tyr217Leu |
| Gly202Asn | + Asn212Glu | + Lys213Asp | + Tyr217Leu |

TABLE 6

Quintuple Mutation BPN' Variants

Gly202Pro + Val203Gly + Gly211Pro + Ala216Pro + Tyr217Leu
Pro201Ser + Thr208Ser + Tyr217Leu + Asn218Ser + Gly219Ser
Ala200His + Ile205Pro + Gln206Asn + Tyr214Thr + Tyr217Leu
Thr208Asn + Leu209Ala + Ala216Ser + Tyr217Leu + Thr220Gln
Val203Ser + Ile205Val + Gln206Asp + Leu209Cys + Tyr217Leu
Ala200Pro + Lys213Asp + Tyr214Ile + Tyr217Leu + Thr220Ser
Pro201Gly + Gln206Glu + Leu209Asn + Tyr217Leu + Gly219Ser
Ala200Ser + Ser204Asp + Gly215Pro + Tyr217Leu + Thr220Asn
Ala200Pro + Leu209Gln + Ala216Ser + Tyr217Leu + Asn218Asp
Ala200Gly + Gln206Glu + Thr208Ser + Leu209Thr + Tyr217Cys
Pro201Asn + Gly211Asn + Tyr217Met + Gly219Pro + Thr220Gln
Ala200Thr + Gly202Gln + Ile205Leu + Tyr217Leu + Thr220Glu
Pro201Gly + Ile205Cys + Thr208Asn + Tyr214Asn + Tyr217Thr
Ala200Asn + Thr208Gln + Ala216Gln + Tyr217Leu + Gly219Asp
Val203Cys + Leu209Met + Asn212Gln + Tyr214Met + Tyr217Leu
Pro201Gly + Val203Ala + Pro210Glu + Asn212Ser + Tyr217Leu
Val203Gly + Gln206Asp + Leu209Pro + Pro210Ser + Tyr217Leu
Ala200Gly + Ile205Val + Lys213Glu + Ala216Thr + Tyr217Leu
Ala200His + Ile205Ser + Pro210Asn + Gly211Glu + Tyr217Leu
Ala200Pro + Val203Cys + Tyr214Asn + Tyr217Leu + Thr220Pro
Ala200Gln + Ile205His + Tyr214Ala + Gly215Glu + Tyr217Met
Val203Pro + Thr208Ser + Leu209Thr + Gly211Asp + Tyr217Leu
Pro201Gly + Gln206Asn + Thr208Gly + Gly215Pro + Tyr217Leu
Gln206Ser + Thr208Gly + Asn212Gln + Lys213Asp + Tyr217Leu
Gly202Asn + Gln206Asp + Gly211Ser + Asn212Ser + Tyr217Leu

TABLE 6-continued

Quintuple Mutation BPN' Variants

Pro210Asn + Asn212Glu + Tyr214Gln + Tyr217Leu + Thr220Asn
Ala200Gly + Gln206Asp + Thr208Asn + Tyr217Leu + Thr220Asn
Pro201Ser + Pro210Ser + Asn212Ser + Lys213Asp + Tyr217Leu
Gly202Pro + Val203Glu + Ile205Asn + Tyr217Leu + Gly219Asn
Pro201Ser + Gln206Ser + Tyr214Gln + Tyr217Leu + Thr220Gln
Leu209Ala + Gly211Asp + Gly215Gln + Ala216Ser + Tyr217Leu
Ala200Thr + Val203His + Gln206Asp + Gly211Asn + Tyr217Leu
Gly202Gln + Gln206Asn + Asn212ser + Tyr217Leu + Asn218Glu
Ala200Gly + Pro210Gln + Tyr214Val + Tyr217Leu + Gly219Asp
Val203His + Ile205Met + Gly215Asn + Tyr217Gln + Asn218Glu
Val203Met + Ile205Asn + Thr208Pro + Tyr217Leu + Thr220Glu
Ile205Asn + Pro210Gly + Tyr214His + Tyr217Leu + Thr220Gly
Val203Asn + Leu209Val + Tyr217Val + Asn218Asp + Thr220Ser
Ala200Asn + Pro210Gln + Gly211Asp + Gly215pro + Tyr217Leu
Ala200Pro + Gly202Gln + Pro210Asn + Tyr214Ser + Tyr217Leu
Gly202Asn + Thr208Asn + Ala216Gly + Tyr217Leu + Asn218Asp
Gln206Ser + Thr208Gly + Pro210Ser + Tyr214Gln + Tyr217Leu
Gly202Pro + Ile205Asn + Gly211Asp + Gly215Pro + Tyr217Cys
Ala200His + Ile205Cys + Gln206Glu + Ala216Pro + Tyr217Ser
Ala200Asn + Pro201Ser + Gly202Ser + Tyr217Leu + Thr220Pro
Ala200Pro + Ser204Glu + Thr208Ser + Ala216Asn + Tyr217Leu
Leu209Ala + Gly211Ser + Ala216Glu + Tyr217Leu + Asn218Gln
Gly202Gln + Ile205Gln + Gly211Asn + Tyr217Leu + Asn218Gln
Gly202Asn + Leu209His + Gly211Asn + Tyr217Leu + Asn218Glu
Ile205Pro + Gln206Ser + Tyr217Leu + Asn218Asp + Thr220Gly
Ala200Pro + Ser204Glu + Thr208Pro + Asn212Gln + Tyr217Leu
Ala200Asn + Leu209Gly + Pro210Gly + Asn212Asp + Tyr217Leu
Ile205Gly + Leu209Gln + Lys213Asp + Gly215Gln + Tyr217Leu
Ala200Gln + Tyr214Leu + Gly215Asp + Tyr217Leu + Thr220Gln
Val203Cys + Leu209Ala + Pro210Asn + Tyr217Leu + Gly219Gly
Gly202Asn + Ile205Pro + Gly211Glu + Tyr217Leu + Asn218Gln
Ile205Gly + Tyr214Met + Tyr217Asn + Asn218Ser + Gly219Asn
Pro201Asn + Gly202Pro + Ser204Glu + Leu209Ser + Tyr217Leu
Ala200His + Val203Met + Pro210Asn + Gly211Asp + Tyr217Leu
Ala200Ser + Ile205His + Leu209Gly + Tyr217Leu + Thr220Asp
Pro201Asn + Val203Met + Ser204Glu + Ile205Pro + Tyr217Leu
Pro201Ser + Gly202Ser + Gly215Ser + Ala216Glu + Tyr217Leu
Val203Thr + Leu209Gln + Ala216Pro + Tyr217Asn + Asn218Asp
Ala200Pro + Thr208Gln + Leu209His + Lys213Asp + Tyr217His
Ala200Ser + Ile205Ala + Gly215Asp + Tyr217Leu + Gly219Asn
Ala200Gln + Ile205Ala + Gly211Glu + Ala216Ser + Tyr217Leu
Ile205Cys + Leu209Thr + Pro210Gln + Tyr217Cys + Asn218Asp
Ala200Thr + Leu209Ala + Gly211Pro + Tyr217Leu + Gly219Glu
Pro201Asn + Val203His + Leu209Ser + Tyr217Leu + Gly219Ser
Pro201Asn + Thr208Asn + Gly215Pro + Tyr217Leu + Gly219Glu
Val203Asn + Gln206Asp + Ala216Thr + Tyr217Leu + Thr220Asn
Val203His + Ile205Asn + Pro210Glu + Tyr217Gly + Gly219Gln
Ala200Asn + Pro201Gly + Lys213Asp + Gly215Asn + Tyr217Leu
Val203Cys + Gln206Asn + Gly215Asp + Tyr217Gly + Asn218Ser
Thr208Gln + Pro210Gln + Lys213Asp + Gly215Gln + Tyr217Gly
Gln206Asn + Leu209Cys + Pro210Ser + Tyr214Ser + Tyr217Leu
Gly202Ser + Tyr214Ile + Tyr217Met + Asn218Glu + Thr220Gln
Pro201Ser + Gln206Asp + Leu209His + Ala216Asn + Tyr217Leu
Ala200Ser + Val203Pro + Leu209His + Tyr217Ser + Gly219Asp
Pro201Gln + Val203Gys + Gly211Asn + Tyr217Leu + Asn218Ser
Ala200Pro + Gly211Asn + Lys213Glu + Tyr214Pro + Tyr217Leu
Ala200Asn + Thr208Pro + Ala216Gly + Tyr217Gly + Gly219Asn
Val203His + Ile205Leu + Pro210Glu + Tyr214Gly + Tyr217Leu
Leu209Met + Pro210Asn + Lys213Asp + Tyr217Leu + Thr220Gln
Ala200Thr + Ile205His + Gln206Asp + Pro210Asn + Tyr217Leu
Ala200Gln + Val203Ser + Tyr214Val + Tyr217Leu + Asn218Glu
Ala200Asn + Pro210Glu + Gly211Ser + Tyr214Val + Tyr217Leu
Gly202Pro + Val203Ser + Lys213Asp + Gly215Gln + Tyr217Leu
Val203Cys + Ile205Thr + Gly211Gln + Gly215Asp + Tyr217Leu
Gly202Gln + Val203Ala + Gly211Asn + Tyr217Leu + Asn218Gln
Ala200Gln + Gln206Ser + Pro210Ser + Tyr217Leu + Gly219Asn
Gly202Gln + Val203Ala + Gln206Asn + Leu209Gly + Tyr217Leu
Ala200His + Ser204Glu + Thr208Ser + Pro210Asn + Tyr217Leu
Ala200Thr + Leu209Asn + Gly215Ser + Tyr217Asn + Gly219Pro
Val203Gln + Pro210Ser + Tyr217Leu + Gly219Ser + Thr220Pro
Ala200Ser + Lys213Asp + Tyr217Leu + Asn218Ser + Gly219Ser
Pro201Gly + Gly202Ser + Pro210Glu + Tyr217Leu + Gly219Asn
Ala200Asn + Ile205Cys + Gln206Glu + Tyr214Cys + Tyr217Leu
Pro201Gln + Leu209Val + Gly211Pro + Tyr217Leu + Asn218Asp
Gly211Asn + Asn212Ser + Tyr217Leu + Asn218Gln + Thr220Asn
Val203Asn + Leu209Pro + Gly211Ser + Gly215Gln + Tyr217Ala
Ala200Gly + Gly211Asn + Tyr214Gly + Tyr217Ala + Asn218Glu

TABLE 6-continued

Quintuple Mutation BPN' Variants

Ile205Met + Asn212Gln + Gly215Asp + Ala216Pro + Tyr217Leu
Pro201Gln + Ile205Met + Asn212Glu + Tyr217Leu + Thr220Gln
Ala200Asn + Thr208Ser + Lys213Glu + Gly215Pro + Tyr217Leu
Pro201Asn + Leu209Gly + Tyr214Leu + Gly215Glu + Tyr217Leu
Gly202Asn + Ile205Met + Asn212Ser + Lys213Asp + Tyr217Leu
Gly202Gln + Gln206Asn + Thr208Ser + Tyr214Glu + Tyr217Leu
Ala200Pro + Gln206Ser + Thr208Asn + Tyr217Asn + Thr220Gly
Val203Glu + Leu209His + Gly215Ser + Ala216Ser + Tyr217Leu
Ile205Asn + Pro210Asp + Asn212Gln + Tyr217Leu + Thr220Gln
Pro201Ser + Val203Gly + Gly211Pro + Ala216Gln + Tyr217Gln
Ala200Gln + Pro201Asn + Ile205Cys + Pro210Asp + Tyr217Leu
Ser204Glu + Thr208Asn + Asn212Gln + Tyr214Met + Tyr217Leu
Val203Asn + Thr208Ser + Asn212Glu + Tyr217Leu + Thr220Ser
Ile205Gly + Thr208Asn + Leu209Met + Asn212Asp + Tyr217Val
Ala200Pro + Thr208Ser + Tyr217Leu + Asn218Glu + Thr220Pro
Gln206Asp + Thr208Gln + Ala216Thr + Tyr217Leu + Thr220Pro
Ile205Ala + Gln206Asp + Thr208Asn + Tyr217Leu + Asn218Ala
Pro201Asn + Gly202Ser + Ser204Asp + Pro210Asn + Tyr217Leu
Pro201Asn + Tyr214Pro + Tyr217Leu + Asn218Asp + Thr220Asn
Ala200Pro + Gln206Asp + Leu209His + Pro210Gln + Tyr217Leu
Pro201Ser + Gly202Asn + Leu209His + Pro210Glu + Tyr217Leu
Ala200His + Thr208Asn + Leu209Thr + Asn212Gln + Tyr217Leu
Gly202Gln + Val203Ser + Gly215Asn + Tyr217Leu + Gly219Gln
Pro201Asn + Leu209Ala + Ala216Asn + Tyr217Leu + Thr220Asp
Pro201Asn + Gly202Gln + Lys213Glu + Tyr217Leu + Asn218Gln
Ala200His + Gly215Pro + Ala216Asp + Tyr217Leu + Asn218Gln
Leu209Met + Ala216Ser + Tyr217Thr + Gly219Glu + Thr220Ser
Gln206Asn + Ala216Pro + Tyr217Leu + Asn218Asp + Gly219Asp
Ala200Gly + Asn212Glu + Lys213Asp + Tyr217Cys + Asn218Gln
Ala200His + Asn212Asp + Lys213Asp + Tyr217Leu + Thr220Pro
Pro201Asn + Val203Cys + Asn212Glu + Lys213Asp + Tyr217Gly
Asn212Glu + Lys213Asp + Ala216Pro + Tyr217Leu + Thr220Asn
Pro201Asn + Val203Asp + Ser204Glu + Leu209Ser + Tyr217Leu
Val203Glu + Ser204Asp + Ile205Gln + Leu209Thr + Tyr217Leu
Gly202Pro + Asn212Ser + Ala216Glu + Tyr217Asp + Gly219Ser
Pro201Gln + Gly211Asp + Asn212Asp + Gly215Pro + Tyr217Leu
Gly211Glu + Asn212Glu + Gly215Ser + Ala216Gln + Tyr217Leu
Ile205Thr + Thr208Gly + Gly211Glu + Asn212Glu + Tyr217Leu
Gly211Asp + Asn212Glu + Lys213Glu + Ala216Asn + Tyr217Leu
Val203Glu + Gln206Asn + Leu209Asn + Tyr217Leu + Asn218Glu
Gly202Gln + Ser204Glu + Leu209Asn + Ala216Asp + Tyr217Leu
Ile205His + Lys213Glu + Tyr214Glu + Gly215Asp + Tyr217Leu
Gly202Gln + Val203Met + Ser204Glu + Tyr217Leu + Asn218Glu
Ser204Glu + Leu209Ala + Tyr217Leu + Asn218Glu + Thr220Gln
Gln206Asp + Leu209Ala + Tyr214Val + Gly215Glu + Tyr217Pro
Ser204Asp + Asn212Gln + Ala216Thr + Tyr217Glu + Thr220Asn
Ser204Asp + Ile205Pro + Leu209Pro + Ala216Ser + Tyr217Glu
Ile205Thr + Pro210Glu + Lys213Glu + Tyr217Leu + Thr220Pro
Pro201Gly + Ser204Glu + Gln206Asp + Tyr217Leu + Thr220Pro
Pro201Gly + Gly202Gln + Thr208Pro + Gly215Asp + Tyr217Asp
Thr208Pro + Gly211Gln + Lys213Glu + Gly215Asp + Tyr217Leu
Gly202Pro + Ile205Ser + Lys213Glu + Gly215Glu + Tyr217Leu
Ala200Gly + Val203Glu + Gln206Asp + Tyr217Leu + Asn218Glu
Val203Glu + Tyr214Ile + Ala216Glu + Tyr217Leu + Gly219Gln
Gly202Pro + Ser204Glu + Thr208Gly + Tyr217Leu + Gly219Asp
Ala200Thr + Ser204Glu + Tyr217Leu + Gly219Asp + Thr220Asn
Gly202Gln + Ser204Asp + Ile205His + Tyr217Leu + Gly219Asp
Val203Asp + Asn212Gln + Ala216Pro + Tyr217Leu + Thr220Asp
Pro201Gln + Ser204Glu + Tyr214Gln + Gly215Glu + Tyr217Leu
Val203Ala + Ser204Glu + Gly211Asn + Gly215Asp + Tyr217Leu
Thr208Ser + Pro210Glu + Gly211Asp + Gly215Glu + Tyr217Ala
Pro201Asn + Val203Asp + Gln206Asp + Tyr217Leu + Gly219Gln
Val203Glu + Gln206Glu + Leu209Gln + Asn212Ser + Tyr217Leu
Gln206Glu + Thr208Gln + Tyr217Leu + Asn218Asp + Thr220Ser
Ala200Asn + Gln206Glu + Leu209Thr + Tyr217Ser + Asn218Glu
Ala200Gly + Pro201Ser + Gln206Glu + Tyr217Leu + Asn218Asp
Val203Asn + Gln206Glu + Pro210Gly + Tyr217Leu + Asn218Asp
Gly211Glu + Lys213Asp + Gly215Asp + Ala216Glu + Tyr217Leu
Gly202Gln + Ala216Glu + Tyr217Leu + Asn218Glu + Thr220Asp
Pro210Asp + Gly215Glu + Ala216Asn + Tyr217Leu + Thr220Pro
Gly202Asn + Ile205Asn + Pro210Glu + Gly215Glu + Tyr217Leu
Asn212Asp + Tyr214Cys + Gly215Asp + Ala216Asp + Tyr217Leu
Gly202Gln + Gln206Asp + Gly211Glu + Tyr214Asp + Tyr217Leu
Ser204Asp + Leu209Ala + Gly215Asp + Tyr217His + Gly219Asp
Ile205Val + Thr208Gly + Gly215Glu + Tyr217Leu + Asn218Asp
Val203Asn + Thr208Gln + Gly215Glu + Tyr217Leu + Asn218Asp
Pro201Gly + Asn212Gln + Gly215Glu + Tyr217Leu + Asn218Asp
Gln206Asp + Tyr217Leu + Asn218Asp + Gly219Ser + Thr220Glu

TABLE 7

Sextuple Mutation BPN' Variants

Ala200Gln + Pro201Gln + Ile205Met + Asn212Asp + Tyr214Pro + Tyr217Leu
Ala200His + Pro201Gln + Gln206Asn + Thr208Gly + Tyr217Leu + Thr220Asn
Pro201Gly + Gly202Ser + Asn212Asp + Tyr214Gln + Ala216Ser + Tyr217Leu
Pro201Ser + Val203Met + Ile205Thr + Pro210Ser + Tyr217Leu + Gly219Glu
Gly202Ser + Ile205Gln + Ala216Asn + Tyr217Leu + Asn218Ser + Thr220Gln
Ala200Gln + Val203Gly + Gln206Glu + Ala216Ser + Tyr217Leu + Gly219Gln
Val203Glu + Leu209Ser + Tyr214Ala + Ala216Thr + Tyr217Leu + Gly219Gln
Gly202Ser + Thr208Gly + Gly215Ser + Tyr217Leu + Gly219Asn + Thr220Glu
Ala200Gly + Gly202Asn + Leu209Cys + Pro210Gly + Tyr217Leu + Thr220Asp
Pro201Ser + Thr208Ser + Gly215Ser + Tyr217Gly + Asn218Asp + Thr220Ser
Gly202Pro + Ser204Asp + Leu209Ala + Tyr217Met + Gly219Asn + Thr220Asn
Pro201Ser + Thr208Gln + Leu209Gln + Gly215Glu + Ala216Thr + Tyr217Leu
Ala200Thr + Gly202Asn + Val203Gln + Leu209Thr + Tyr217Leu + Asn218Gln
Pro201Ser + Gly211Asn + Gly215Gln + Ala216Gln + Tyr217Leu + Asn218Glu
Gly202Ser + Ile205Gln + Gln206Asn + Thr208Gly + Ala216Glu + Tyr217Leu
Val203Ala + Gly211Gln + Ala216Gln + Tyr217Asn + Gly219Pro + Thr220Asp
Gly202Gln + Ile205His + Leu209Pro + Tyr214Asp + Ala216Gln + Tyr217Leu
Val203Gly + Thr208Gln + Leu209Gln + Asn212Ser + Tyr217Cys + Gly219Pro
Gly202Gln + Val203Ser + Thr208Ser + Tyr217Gly + Asn218Asp + Thr220Ser
Gly202Pro + Leu209Ile + Lys213Asp + Gly215Gln + Tyr217Cys + Asn218Gln
Pro201Gly + Ile205Val + Gln206Asn + Asn212Ser + Tyr214Pro + Tyr217Leu
Ala200Gln + Gly202Pro + Val203Cys + Gly215Gln + Ala216Asp + Tyr217Leu
Ala200Gln + Gln206Ser + Asn212Gln + Gly215Pro + Tyr217Leu + Asn218Asp
Pro201Gln + Gly202Ser + Ala216Gln + Tyr217Leu + Asn218Gln + Gly219Pro
Ala200Pro + Gly202Pro + Ile205Thr + Gly211Glu + Gly215Gln + Tyr217Ile
Gln206Ser + Thr208Ser + Leu209Pro + Gly215Asp + Tyr217Leu + Asn218Gln
Thr208Gln + Pro210Asp + Tyr217Leu + Asn218Ser + Gly219Pro + Thr220Asn
Ala200Ser + Thr208Gln + Leu209Cys + Gly211Gln + Tyr217Ile + Gly219Asp
Pro201Gln + Ile205Ser + Asn212Asp + Gly215Asn + Tyr217Leu + Thr220Pro
Ala200Pro + Pro210Asn + Gly211Glu + Ala216Gln + Tyr217Leu + Thr220Pro
Ala200Gln + Ile205Met + Pro210Ser + Lys213Asp + Tyr217Leu + Asn218Gln
Ala200Pro + Thr208Asn + Tyr214Met + Gly215Ser + Tyr217Leu + Gly219Glu
Val203Gly + Ile205His + Gln206Asn + Tyr214Asp + Gly215Pro + Tyr217Leu

TABLE 7-continued

Sextuple Mutation BPN' Variants

Ala200Asn + Pro201Gly + Ile205Val + Gly211Asn + Gly215Gln + Tyr217Leu
Ala200Thr + Pro201Gly + Val203Asn + Gly211Asn + Tyr217Leu + Asn218Asp
Ser204Asp + Gln206Ser + Thr208Gln + Leu209Gly + Gly211Gln + Tyr217Leu
Ala200Gly + Gly202Ser + Ser204Glu + Thr208Gln + Leu209Thr + Tyr217Leu
Pro201Gly + Thr208Asn + Leu209Pro + Tyr214Pro + Ala216Gln + Tyr217Leu
Ala200Ser + Val203His + Ile205Leu + Leu209Pro + Tyr217Leu + Gly219Asn
Ser204Glu + Thr208Ser + Pro210Gly + Tyr214Ser + Gly215Gln + Tyr217Leu
Ile205Gly + Thr208Gln + Leu209Ser + Gly211Gln + Lys213Asp + Tyr217Leu
Pro201Asn + Thr208Ser + Pro210Gly + Gly215Asn + Tyr217Leu + Gly219Ser
Ile205Met + Pro210Ser + Tyr214Asp + Gly215Asn + Tyr217Leu + Thr220Ser
Gly202Gln + Thr208Gln + Gly211Asn + Gly215Ser + Tyr217Leu + Thr220Gly
Gly202Gln + Val203Met + Thr208Asn + Asn212Gln + Gly215Pro + Tyr217Leu
Pro201Gln + Gly202Ser + Val203Gln + Tyr217Cys + Gly219Asp + Thr220Ser
Val203Cys + Ile205His + Thr208Pro + Asn212Gln + Tyr214Gly + Tyr217Leu
Thr208Ser + Leu209Val + Pro210Asn + Lys213Glu + Gly215Ser + Tyr217Leu
Gly202Pro + Thr208Pro + Gly211Asn + Gly215Ser + Tyr217Leu + Gly219Asn
Ala200Gly + Thr208Gly + Lys213Glu + Ala216Ser + Tyr217Leu + Thr220Ser
Pro201Gly + Gln206Ser + Leu209Thr + Gly215Pro + Ala216His + Tyr217Leu
Pro201Gln + Gly202Pro + Ser204Asp + Ile205His + Pro210Ser + Tyr217Leu
Ala200Gln + Val203Pro + Ile205His + Thr208Gly + Ala216Ser + Tyr217Leu
Val203Met + Thr208Pro + Leu209Ile + Tyr214Glu + Tyr217Leu + Thr220Asn
Ala200His + Gly202Ser + Gln206Asp + Ala216Gln + Tyr217Leu + Gly219Pro
Ile205Thr + Gln206Ser + Gly211Asn + Lys213Asp + Ala216Gln + Tyr217Leu
Ala200Gly + Ile205Ala + Gln206Asp + Thr208Gln + Leu209Asn + Tyr217Leu
Ala200Ser + Thr208Asn + Ala216Ser + Tyr217Leu + Gly219Ser + Thr220Pro
Val203Ala + Ile205Gly + Leu209Ile + Gly215Pro + Tyr217Leu + Asn218Asp
Gly202Ser + Ile205Asn + Gln206Asp + Gly211Asn + Ala216Pro + Tyr217Leu
Ser204Glu + Gln206Ser + Leu209Asn + Ala216Thr + Tyr217Leu + Gly219Ser
Pro201Asn + Gln206Asp + Thr208Gln + Ala216Asn + Tyr217Leu + Thr220Pro
Ala200His + Val203Met + Gly211Gln + Tyr214Ile + Tyr217Leu + Asn218Glu
Ala200Asn + Gly202Asn + Gln206Glu + Thr208Pro + Tyr214Leu + Tyr217Leu
Gly202Gln + Ile205Pro + Gln206Ser + Lys213Glu + Tyr217Leu + Gly219Ser
Pro201Ser + Thr208Ser + Leu209Gly + Lys213Glu + Tyr217Leu + Asn218Ser
Ala200Gln + Thr208Asn + Leu209His + Gly211Asp + Ala216Asn + Tyr217Leu
Ala200His + Pro201Asn + Gly202Ser + Val203Asn + Lys213Asp + Tyr217Leu
Gly202Asn + Thr208Ser + Pro210Gln + Gly211Ser + Tyr217Leu + Asn218Glu
Ala200Gly + Val203Gln + Gln206Asn + Gly211Gln + Tyr217Leu + Gly219Pro
Gly202Ser + Val203Pro + Thr208Pro + Ala216His + Tyr217Gln + Gly219Pro
Gly202Ser + Ser204Glu + Asn212Gln + Tyr217Leu + Gly219Asn + Thr220Gln
Val203Ser + Thr208Gln + Pro210Asp + Gly215Asn + Ala216His + Tyr217Pro
Val203Ala + Leu209Thr + Asn212Gln + Lys213Glu + Ala216Ser + Tyr217Leu
Ala200Thr + Gln206Ser + Pro210Asn + Asn212Ser + Tyr217Leu + Asn218Asp
Ala200Gln + Ile205His + Leu209Asn + Tyr214Cys + Tyr217Leu + Thr220Ser
Gly202Gln + Ile205Pro + Thr208Pro + Gly211Glu + Tyr214Gln + Tyr217Leu
Ala200Gln + Ile205Ser + Thr208Gln + Ala216Asn + Tyr217Leu + Thr220Ser
Pro201Ser + Gly202Asn + Gly211Gln + Tyr214Asp + Tyr217Leu + Gly219Pro
Thr208Asn + Leu209His + Gly211Pro + Lys213Glu + Ala216Gly + Tyr217Leu
Ala200Thr + Leu209Gly + Asn212Asp + Tyr214Ala + Ala216Gly + Tyr217Leu
Ala200Thr + Pro201Gln + Thr208Gln + Lys213Glu + Gly215Ser + Tyr217Asn
Val203Ala + Gln206Ser + Thr208Ser + Gly215Asn + Ala216Pro + Tyr217Leu
Ala200Asn + Ile205Met + Thr208Ser + Asn212Glu + Gly215Pro + Tyr217Leu
Gly202Asn + Leu209Gly + Pro210Asn + Lys213Glu + Tyr217Pro + Asn218Gln
Ala200Pro + Gln206Asn + Thr208Gln + Gly215Gln + Ala216Thr + Tyr217Leu
Ala200Asn + Pro201Asn + Leu209Thr + Asn212Ser + Tyr217Leu + Thr220Gln
Gly202Gln + Ile205Gln + Asn212Ser + Tyr214Asn + Tyr217Leu + Gly219Gln
Val203Asn + Gln206Ser + Pro210Glu + Gly211Glu + Tyr217Leu + Gly219Asn
Ala200Thr + Ile205Asn + Gly211Asn + Asn212Asp + Lys213Asp + Tyr217Gln
Gln206Asn + Leu209Ala + Asn212Glu + Lys213Asp + Tyr217Leu + Thr220Pro
Ala200Asn + Pro210Gly + Gly211Gln + Asn212Glu + Lys213Asp + Tyr217Leu
Val203Thr + Thr208Gln + Gly211Asp + Asn212Glu + Tyr217Leu + Thr220Ser
Ile205Cys + Gly211Asp + Asn212Glu + Gly215Gln + Tyr217Leu + Thr220Pro
Pro201Ser + Gly202Ser + Gln206Asp + Ala216Glu + Tyr217Ser + Gly219Pro
Ala200Thr + Pro201Gly + Val203Glu + Thr208Pro + Tyr217Leu + Asn218Glu
Thr208Pro + Pro210Asp + Gly211Glu + Asn212Glu + Tyr214Ala + Tyr217Leu
Gly202Gln + Pro210Glu + Gly211Glu + Asn212Glu + Gly215Ser + Tyr217Leu
Ser204Asp + Tyr214Val + Ala216Asp + Tyr217Leu + Gly219Pro + Thr220Pro
Gly202Asn + Ser204Asp + Leu209Met + Gly211Gln + Ala216Glu + Tyr217Leu
Pro201Gly + Ser204Asp + Tyr214Gln + Ala216Asn + Tyr217Met + Asn218Asp
Ala200His + Pro210Asp + Asn212Glu + Lys213Glu + Tyr214Ala + Tyr217Leu
Pro201Asn + Ser204Asp + Gln206Glu + Pro210Gln + Ala216Asp + Tyr217Leu
Ile205Met + Pro210Ser + Gly211Glu + Lys213Glu + Tyr217Val + Gly219Gln
Thr208Asn + Pro210Gly + Gly211Asp + Lys213Asp + Ala216His + Tyr217Leu
Val203Thr + Pro210Asp + Asn212Asp + Tyr214Met + Ala216Gly + Tyr217Leu
Pro201Ser + Leu209Asn + Pro210Glu + Asn212Glu + Tyr214Ser + Tyr217Leu
Ala200Asn + Ser204Glu + Ala216Asp + Tyr217Leu + Asn218Asp + Thr220Pro
Pro201Asn + Pro210Glu + Lys213Asp + Tyr214Thr + Tyr217Leu + Asn218Gln

TABLE 7-continued

Sextuple Mutation BPN' Variants

Pro201Gln + Ser204Glu + Gly215Asp + Ala216Asp + Tyr217Leu + Thr220Pro
Ala200Thr + Ser204Asp + Gln206Glu + Thr208Pro + Leu209Ile + Tyr217Leu
Ala200His + Pro201Ser + Ser204Glu + Gln206Glu + Pro210Ser + Tyr217Leu
Ala200Thr + Pro201Ser + Ser204Glu + Gln206Asp + Thr208Ser + Tyr217Leu
Gly202Gln + Ser204Glu + Gln206Asp + Leu209Gln + Pro210Gln + Tyr217Leu
Ala200Ser + Ser204Asp + Gln206Asp + Tyr217Leu + Gly219Pro + Thr220Pro
Ala200Gln + Gln206Asn + Gly211Glu + Lys213Asp + Tyr214Asp + Tyr217Leu
Val203Glu + Ser204Glu + Thr208Ser + Leu209Thr + Tyr217Leu + Gly219Asp
Ile205Met + Gln206Asp + Asn212Gln + Tyr214Glu + Ala216Pro + Tyr217Leu
Val203Asp + Ser204Asp + Gln206Glu + Gly211Pro + Tyr214Leu + Tyr217Pro
Val203Asp + Ser204Glu + Ile205Leu + Gln206Glu + Leu209Ala + Tyr217Leu
Pro201Asn + Gly202Pro + Lys213Asp + Tyr214Leu + Gly215Glu + Tyr217Leu
Pro201Asn + Pro210Gln + Asn212Ser + Lys213Asp + Gly215Glu + Tyr217Leu
Gly202Ser + Gln206Asn + Thr208Gln + Tyr217Leu + Asn218Asp + Thr220Glu
Ala200Gly + Asn212Ser + Tyr217Leu + Asn218Asp + Gly219Asn + Thr220Asp
Ile205Asn + Leu209His + Gly211Ser + Tyr217Leu + Asn218Asp + Thr220Glu
Ala200Pro + Ile205Gly + Leu209Met + Tyr214Glu + Ala216Asp + Tyr217Cys
Gly202Gln + Thr208Asn + Leu209Cys + Pro210Asp + Tyr214Asp + Tyr217Leu
Ser204Asp + Gln206Ser + Tyr217Leu + Asn218Asp + Gly219Ser + Thr220Asp
Pro201Gln + Gly202Gln + Val203Asp + Ser204Glu + Tyr217Leu + Thr220Asp
Ala200Thr + Pro201Ser + Gly202Pro + Ser204Asp + Tyr217Leu + Gly219Asp
Ala200Thr + Ser204Glu + Ile205Gly + Gly215Ser + Tyr217Leu + Gly219Asp
Pro201Asn + Val203Asp + Gly215Gln + Tyr217Gln + Gly219Pro + Thr220Glu
Gln206Asp + Asn212Ser + Tyr214Pro + Gly215Glu + Tyr217Leu + Asn218Glu
Pro201Asn + Ser204Glu + Tyr214Ile + Gly215Asp + Tyr217Leu + Gly219Asn
Ala200Ser + Val203Pro + Ser204Glu + Tyr214Leu + Gly215Asp + Tyr217Leu
Val203Asp + Ser204Asp + Ile205Asn + Leu209Asn + Gly215Glu + Tyr217Leu
Pro201Gln + Thr208Gly + Pro210Ser + Gly211Asp + Tyr214Asp + Tyr217Leu
Ser204Asp + Lys213Asp + Tyr214Asp + Gly215Asp + Tyr217Leu + Gly219Pro
Ser204Glu + Gln206Asp + Lys213Glu + Ala216Glu + Tyr217Leu + Thr220Ser
Ile205Asn + Gln206Glu + Leu209Cys + Tyr214His + Tyr217Leu + Asn218Asp
Pro201Gln + Gln206Asp + Pro210Ser + Gly211Ser + Tyr217Leu + Asn218Asp
Pro201Ser + Gly202Asn + Gln206Glu + Gly215Asn + Tyr217Leu + Asn218Asp
Gly202Gln + Gln206Glu + Ala216Glu + Tyr217Leu + Asn218Asp + Thr220Asp
Ile205Ser + Leu209Thr + Pro210Asp + Lys213Asp + Ala216Glu + Tyr217Leu
Gly202Gln + Pro210Ser + Tyr214Glu + Gly215Glu + Tyr217Leu + Asn218Glu
Thr208Pro + Tyr214Met + Ala216Glu + Tyr217Leu + Gly219Asp + Thr220Gly
Val203Met + Ser204Asp + Gln206Glu + Lys213Asp + Tyr217His + Asn218Glu

TABLE 7-continued

Sextuple Mutation BPN' Variants

Ser204Glu + Ile205Gln + Gly211Asp + Lys213Glu + Tyr214Glu + Tyr217Gly
Pro201Gln + Leu209Asn + Asn212Asp + Tyr214Pro + Gly215Asp + Tyr217Leu
Pro201Gln + Asn212Glu + Tyr214Val + Gly215Glu + Tyr217Leu + Thr220Gly
Gly202Pro + Leu209Pro + Asn212Glu + Tyr214Leu + Gly215Glu + Tyr217Leu
Ala200Asn + Thr208Asn + Asn212Glu + Gly215Asp + Tyr217Leu + Gly219Asn
Pro201Asn + Gly202Pro + Leu209Met + Asn212Glu + Gly215Asp + Tyr217Leu
Pro201Gln + Ile205Ser + Asn212Ser + Lys213Glu + Ala216Glu + Tyr217Leu
Ala200His + Val203Met + Gly211Gln + Lys213Asp + Ala216Glu + Tyr217Leu
Ala200Gln + Asn212Gln + Lys213Glu + Gly215Asn + Ala216Glu + Tyr217His
Ile205Asn + Gln206Asp + Leu209Thr + Tyr217Leu + Gly219Asp + Thr220Glu
Pro201Gly + Ser204Asp + Gln206Asn + Lys213Asp + Tyr214Asp + Tyr217Leu
Ala200His + Gln206Asp + Leu209Ala + Pro210Glu + Ala216Asp + Tyr217Leu
Gly202Asn + Asn212Ser + Gly215Glu + Tyr217Leu + Asn218Asp + Thr220Asp
Ser204Asp + Ile205Ser + Gln206Ser + Ala216His + Tyr217Leu + Thr220Glu
Ser204Glu + Gln206Asn + Thr208Asn + Gly215Pro + Tyr217Leu + Thr220Asp
Gln206Glu + Leu209Asn + Pro210Asp + Asn212Asp + Tyr217Met + Thr220Pro
Val203Cys + Gln206Asp + Pro210Gly + Lys213Asp + Tyr217Leu + Asn218Asp
Val203Cys + Ser204Asp + Asn212Asp + Tyr217Leu + Asn218Glu + Thr220Glu
Ser204Asp + Ile205Met + Lys213Glu + Tyr217Leu + Asn218Asp + Thr220Glu
Pro201Ser + Ser204Glu + Asn212Glu + Tyr214Glu + Tyr217Leu + Asn218Glu
Thr208Pro + Gly211Asp + Tyr214Val + Gly215Asp + Tyr217Leu + Thr220Gln
Val203Gly + Ser204Glu + Pro210Asp + Tyr214Glu + Tyr217Gln + Gly219Pro
Pro201Gly + Leu209Gln + Pro210Asp + Gly211Asp + Tyr217Ser + Gly219Glu
Leu209Ile + Gly211Glu + Gly215Ser + Tyr217Ala + Asn218Asp + Gly219Asp
Val203Asp + Leu209Gly + Gly211Gln + Asn212Asp + Lys213Asp + Tyr217Leu
Gly202Gln + Ser204Glu + Ile205Gly + Asn212Glu + Lys213Glu + Tyr217Leu
Ser204Glu + Thr208Gln + Asn212Asp + Lys213Glu + Gly215Gln + Tyr217Leu
Ser204Glu + Thr208Gly + Asn212Glu + Lys213Glu + Gly215Gln + Tyr217Leu
Ala200Gly + Leu209Cys + Asn212Asp + Lys213Asp + Tyr217Leu + Gly219Asp
Ile205Gln + Pro210Ser + Asn212Glu + Lys213Asp + Tyr217Val + Gly219Glu
Val203Glu + Ser204Glu + Gln206Asn + Thr208Gln + Gly211Asp + Tyr217Leu
Pro201Gln + Val203Asp + Ser204Glu + Ile205Ser + Lys213Asp + Tyr217Leu
Ala200Ser + Val203Glu + Thr208Pro + Lys213Glu + Tyr214Glu + Tyr217Leu

TABLE 8

Heptuple Mutation BPN' Variants

Ala200Pro + Ile205Gln + Gln206Asp + Leu209Thr + Pro210Asn + Ala216Ser + Tyr217Leu
Ala200Gln + Pro201Asn + Val203Met + Ile205Ala + Gln206Asp + Ala216Pro + Tyr217Leu

TABLE 8-continued

Heptuple Mutation BPN' Variants

Val203His + Ile205Met + Leu209Pro + Pro210Gln + Gly215Asn + Tyr217Leu + Gly219Asp
Ala200Ser + Val203Thr + Ile205Thr + Gly211Gln + Gly215Asp + Tyr217Leu + Gly219Pro
Leu209Met + Gly211Gln + Lys213Glu + Tyr214Ser + Ala216Ser + Tyr217Leu + Gly219Pro
Ala200Ser + Pro201Gln + Val203His + Ile205Gln + Gly211Pro + Ala216Gln + Tyr217Leu
Ala200Gly + Pro201Gly + Gly202Ser + Val203Thr + Pro210Glu + Gly211Ser + Tyr217Leu
Pro201Asn + Gly202Pro + Ile205Gly + Tyr214Met + Tyr217Leu + Asn218Ser + Gly219Asn
Ala200His + Pro201Asn + Val203Met + Thr208Pro + Gly211Asp + Tyr214Ala + Tyr217Ser
Pro201Asn + Gly202Asn + Gly211Pro + Asn212Glu + Tyr214Val + Tyr217Leu + Thr220Gly
Pro201Ser + Val203Cys + Ser204Glu + Ile205Gln + Gly211Asn + Tyr217Leu + Asn218Ser
Pro201Gln + Val203Met + Gln206Asp + Thr208Gly + Gly211Pro + Tyr214Cys + Tyr217Leu
Ile205Gly + Leu209Ser + Pro210Ser + Gly211Gln + Gly215Ser + Ala216Ser + Tyr217Thr
Pro201Asn + Leu209Ile + Gly211Ser + Lys213Glu + Tyr214Pro + Tyr217Ser + Thr220Pro
Ala200Asn + Pro201Ser + Gly202Gln + Val203His + Tyr217Leu + Asn218Ser + Thr220Glu
Pro201Asn + Ile205Asn + Thr208Gln + Leu209Ser + Gly211Glu + Tyr217Leu + Gly219Asn
Pro201Gln + Gln206Asp + Thr208Gly + Gly211Ser + Gly215Gln + Tyr217Leu + Asn218Gln
Val203Cys + Asn212Gln + Gly215Glu + Ala216His + Tyr217Leu + Asn218Gln + Thr220Pro
Ala200Gln + Pro201Gln + Val203Asp + Ile205His + Gly215Pro + Ala216Gln + Tyr217Leu
Ala200Gln + Gln206Ser + Leu209Gly + Gly211Ser + Tyr217Leu + Asn218Glu + Gly219Pro
Ile205Gln + Thr208Ser + Gly211Asn + Lys213Glu + Tyr214Pro + Tyr217Leu + Thr220Ser
Pro201Asn + Gly202Ser + Ser204Glu + Tyr214Gln + Ala216Thr + Tyr217Leu + Gly219Asn
Pro201Gly + Gly202Ser + Gly211Pro + Asn212Glu + Tyr214Cys + Tyr217Leu + Thr220Asn
Gly202Gln + Thr208Asn + Lys213Glu + Tyr214Ala + Gly215Pro + Tyr217Leu + Thr220Gly
Ala200Pro + Gly202Pro + Ile205Ala + Thr208Ser + Leu209His + Tyr214Glu + Tyr217Leu
Pro201Gly + Gly202Ser + Ile205Gln + Thr208Ser + Leu209His + Lys213Asp + Tyr217Leu
Pro201Gly + Gly202Ser + Ile205Cys + Thr208Ser + Asn212Ser + Ala216Pro + Tyr217Ser
Ala200Ser + Gly202Ser + Val203Cys + Leu209Gly + Pro210Asp + Tyr214Met + Tyr217Leu
Ala200Thr + Pro201Ser + Ile205Ser + Asn212Gln + Tyr214Glu + Gly215Asn + Tyr217Leu
Pro201Gly + Ile205Ala + Lys213Glu + Ala216Asn + Tyr217His + Asn218Gln + Thr220Asn
Ala200Ser + Gly202Gln + Val203Asn + Thr208Ser + Ala216Glu + Tyr217Leu + Thr220Gln
Ile205His + Thr208Asn + Leu209Asn + Tyr214Cys + Gly215Glu + Tyr217Leu + Thr220Ser
Pro201Ser + Gly202Asn + Thr208Asn + Gly211Gln + Tyr214Asp + Tyr217Leu + Gly219Pro
Ala200Pro + Val203Gly + Gln206Asn + Leu209Gly + Tyr214Asn + Tyr217Leu + Gly219Asn
Ala200Ser + Pro201Gly + Ile205His + Gln206Asp + Leu209Ser + Pro210Ser + Tyr217Pro
Ala200Ser + Pro201Asn + Gln206Glu + Gly211Ser + Tyr217Leu + Gly219Gln + Thr220Asn
Gly202Asn + Val203Gly + Thr208Gly + Leu209Gln + Tyr214Val + Tyr217Leu + Gly219Asp
Pro201Asn + Gly202Ser + Leu209His + Tyr214His + Ala216Gly + Tyr217Leu + Thr220Asp
Ala200Gly + Val203Glu + Ile205Val + Gly211Pro + Gly215Gln + Ala216Gly + Tyr217Leu
Ala200Gln + Val203His + Ile205Pro + Tyr214His + Ala216Asp + Tyr217Leu + Asn218Gln
Ala200Pro + Pro201Ser + Gly202Ser + Gln206Asn + Pro210Glu + Tyr217Leu + Gly219Ser
Pro201Ser + Gly202Gln + Thr208Gly + Asn212Gln + Tyr214Ile + Ala216Glu + Tyr217Leu
Ala200Thr + Ile205Val + Asn212Ser + Tyr214Cys + Ala216His + Tyr217Leu + Asn218Asp
Ser204Glu + Thr208Asn + Leu209Cys + Pro210Gln + Gly215Gln + Tyr217Thr + Asn218Gln
Pro201Ser + Gly202Ser + Leu209Pro + Pro210Glu + Tyr214Cys + Tyr217Leu + Thr220Asn
Gly202Asn + Thr208Gly + Leu209Ile + Pro210Gly + Lys213Asp + Gly215Asn + Tyr217Asn
Ala200Ser + Gln206Asn + Leu209Val + Tyr214Pro + Ala216Ser + Tyr217Leu + Asn218Asp
Gly202Asn + Ser204Glu + Gly211Pro + Tyr214Ile + Tyr217Gln + Asn218Gln + Gly219Ser
Pro201Gln + Val203His + Ile205Ala + Gly211Ser + Gly215Asp + Ala216Pro + Tyr217Leu
Pro201Gly + Val203His + Gln206Glu + Asn212Gln + Tyr217Gly + Gly219Ser + Thr220Gln
Gly202Asn + Val203Gln + Gly211Gln + Ala216Glu + Tyr217Leu + Asn218Ser + Gly219Gln
Ile205Gly + Thr208Gly + Gly215Glu + Tyr217Leu + Asn218Ser + Gly219Asn + Thr220Pro
Pro201Gly + Gly202Gln + Ile205Ala + Leu209His + Tyr214Asn + Gly215Gln + Tyr217Leu
Pro201Asn + Val203Met + Gln206Asn + Thr208Pro + Pro210Glu + Gly211Glu + Tyr217Leu
Ala200Pro + Pro201Gly + Ile205His + Thr208Ser + Tyr217Leu + Asn218Glu + Gly219Glu
Ala200Gln + Pro201Gly + Ile205Met + Gly215Ser + Tyr217Leu + Asn218Asp + Gly219Glu
Gly202Gln + Thr208Asn + Leu209Pro + Asn212Glu + Lys213Glu + Gly215Gln + Tyr217Leu
Val203Met + Gln206Ser + Thr208Gln + Asn212Asp + Lys213Asp + Gly215Pro + Tyr217Leu
Ala200Thr + Pro201Gln + Ile205Gly + Asn212Glu + Lys213Glu + Tyr214Asn + Tyr217Leu
Pro201Gln + Asn212Asp + Lys213Asp + Ala216Pro + Tyr217Leu + Asn218Ser + Gly219Asn
Gly202Pro + Val203Glu + Ser204Glu + Ile205Thr + Gln206Ser + Tyr217Leu + Thr220Pro
Ala200Pro + Ile205Pro + Thr208Gln + Lys213Glu + Tyr214Glu + Gly215Ser + Tyr217Leu
Pro201Asn + Val203Met + Leu209Gly + Gly211Asp + Asn212Asp + Tyr217Leu + Thr220Asn
Ile205Asn + Pro210Gly + Gly211Glu + Asn212Asp + Tyr214Ser + Tyr217Leu + Gly219Pro
Pro210Gln + Gly211Glu + Asn212Asp + Lys213Glu + Tyr214Cys + Gly215Ser + Tyr217Leu
Ile205Glu + Pro210Glu + Gly211Glu + Asn212Glu + Ala216Ser + Tyr217Leu + Asn218Ser
Ala200His + Ser204Glu + Ile205Ser + Gln206Asn + Tyr214Pro + Tyr217Leu + Asn218Glu
Gly202Gln + Ser204Asp + Gly211Pro + Gly215Ser + Tyr217Leu + Asn218Asp + Gly219Asn
Ala200Gly + Gly202Asn + Val203Gly + Ser204Glu + Thr208Gln + Tyr217Leu + Asn218Asp
Pro201Ser + Gln206Glu + Thr208Gly + Pro210Asn + Gly215Asp + Ala216Pro + Tyr217Leu
Ala200Ser + Pro201Asn + Ile205Pro + Gln206Asp + Pro210Gly + Gly215Asp + Tyr217Ser
Ala200Gly + Pro201Ser + Gly202Ser + Thr208Gln + Gly211Glu + Lys213Glu + Tyr217Leu
Ala200Asn + Ile205Thr + Gly211Asp + Lys213Asp + Gly215Gln + Tyr217Leu + Thr220Ser
Leu209Met + Pro210Asp + Asn212Glu + Tyr214Cys + Gly215Ser + Tyr217Leu + Gly219Pro
Ala200His + Pro201Ser + Thr208Gly + Leu209Thr + Pro210Asp + Asn212Glu + Tyr217Leu
Ala200Gly + Ile205Ala + Pro210Glu + Lys213Glu + Tyr214Pro + Ala216Ser + Tyr217Leu
Ala200Gln + Ile205His + Gln206Ser + Pro210Glu + Lys213Glu + Tyr217Leu + Gly219Asn
Ala200Thr + Pro201Asn + Val203Gly + Leu209His + Pro210Glu + Lys213Glu + Tyr217Leu

TABLE 8-continued

Heptuple Mutation BPN' Variants

Gly202Gln + Pro210Asp + Gly211Ser + Lys213Asp + Tyr214Ile + Gly215Ser + Tyr217Pro
Gly202Pro + Val203Thr + Thr208Gln + Leu209Gly + Pro210Glu + Lys213Glu + Tyr217Leu
Gly202Asn + Val203Glu + Ser204Asp + Thr208Asn + Ala216Asp + Tyr217Leu + Gly219Gln
Gly202Pro + Val203Glu + Ser204Glu + Leu209Asn + Ala216Asp + Tyr217Thr + Thr220Asn
Gly202Asn + Ser204Asp + Pro210Gln + Gly215Ser + Tyr217Leu + Asn218Asp + Gly219Asp
Ser204Asp + Ile205Asn + Leu209Val + Tyr217Leu + Asn218Glu + Gly219Asp + Thr220Gln
Ser204Asp + Ile205Ala + Gln206Glu + Thr208Ser + Leu209Cys + Tyr217Thr + Gly219Ser
Val203Gln + Ser204Asp + Gln206Glu + Leu209Gly + Ala216Thr + Tyr217Leu + Asn218Ser
Ala200Thr + Ser204Asp + Gln206Glu + Thr208Pro + Leu209Ile + Tyr214Ala + Tyr217Leu
Pro201Gly + Ser204Glu + Ile205Val + Gln206Asp + Pro210Gln + Gly215Pro + Tyr217Leu
Gly202Asn + Ser204Asp + Ile205Met + Gln206Asp + Thr208Ser + Leu209Met + Tyr217Ser
Ala200Gln + Gly202Gln + Thr208Pro + Gly211Glu + Lys213Asp + Tyr214Asp + Tyr217Leu
Pro201Ser + Val203Asp + Ser204Glu + Leu209Ala + Tyr214Asn + Tyr217Leu + Gly219Asp
Gln206Glu + Pro210Ser + Lys213Asp + Tyr214Glu + Gly215Glu + Tyr217Gly + Gly219Pro
Val203Asp + Ser204Asp + Gln206Asp + Thr208Ser + Tyr214Pro + Tyr217Asp + Asn218Glu
Pro201Ser + Ser204Glu + Gln206Asp + Pro210Ser + Tyr214Asn + Gly215Glu + Tyr217Leu
Val203Ser + Gln206Asn + Gly211Asn + Lys213Glu + Gly215Asp + Tyr217Gly + Thr220Asn
Ala200Ser + Ile205Pro + Thr208Gln + Pro210Gln + Lys213Asp + Gly215Asp + Tyr217Leu
Thr208Gln + Pro210Asn + Gly211Ser + Tyr214Thr + Ala216Glu + Tyr217Leu + Asn218Glu
Ala200Ser + Pro201Asn + Gly202Ser + Gly211Asp + Asn212Glu + Tyr214Glu + Tyr217Leu
Pro201Gly + Gly202Asn + Ser204Asp + Gln206Glu + Asn212Gln + Tyr217Leu + Asn218Asp
Gly202Pro + Val203Met + Ser204Glu + Ile205Asn + Gln206Asp + Tyr217Leu + Asn218Glu
Gly202Asn + Val203Cys + Ser204Asp + Gln206Glu + Thr208Ser + Tyr217Leu + Asn218Glu
Val203Met + Ile205Asn + Thr208Pro + Pro210Gly + Tyr217Leu + Asn218Glu + Thr220Glu
Val203Thr + Pro210Asn + Lys213Asp + Tyr214Glu + Ala216Glu + Tyr217Leu + Thr220Asn
Ser204Asp + Gln206Glu + Gly211Ser + Gly215Asp + Ala216Ser + Tyr217Leu + Asn218Glu
Val203Glu + Gln206Glu + Thr208Asn + Gly211Pro + Ala216Gln + Tyr217Leu + Asn218Glu
Pro201Asn + Gly202Gln + Ser204Glu + Gly211Ser + Ala216Asp + Tyr217Leu + Gly219Glu
Gln206Asp + Pro210Gln + Gly211Ser + Ala216Asp + Tyr217Leu + Asn218Asp + Gly219Asp
Pro201Gln + Gly211Glu + Lys213Asp + Gly215Glu + Ala216Gln + Tyr217Leu + Thr220Pro
Ser204Asp + Gly211Pro + Asn212Gln + Tyr214His + Tyr217Leu + Asn218Gln + Gly219Glu
Gly202Pro + Val203Gly + Ser204Glu + Tyr217Leu + Asn218Ser + Gly219Asp + Thr220Asn
Val203Gly + Ser204Asp + Ile205Cys + Thr208Gln + Pro210Gly + Tyr217Val + Gly219Asp
Ala200His + Gly202Gln + Val203Asp + Leu209Gly + Tyr217Leu + Gly219Gln + Thr220Asp
Pro201Gly + Ser204Asp + Leu209Asn + Tyr214Thr + Gly215Asp + Tyr217Ser + Thr220Pro
Ala200Ser + Ser204Asp + Ile205Leu + Leu209Ser + Gly215Asp + Tyr217Leu + Thr220Gln
Pro201Gln + Gly202Asn + Ser204Asp + Ile205His + Thr208Pro + Gly215Asp + Tyr217Leu
Pro201Gly + Gly202Asn + Gln206Asp + Thr208Gly + Lys213Asp + Ala216Asp + Tyr217Leu
Gln206Glu + Thr208Gly + Pro210Gly + Asn212Asp + Lys213Asp + Gly215Asp + Tyr217Leu
Pro210Glu + Gly211Asp + Tyr214Pro + Gly215Asp + Tyr217Leu + Gly219Pro + Thr220Gly
Ala200Ser + Val203Thr + Ile205Ala + Gln206Asp + Ala216Thr + Tyr217Leu + Asn218Glu
Ala200Ser + Gly202Asn + Gln206Asn + Gly211Glu + Asn212Asp + Gly215Glu + Tyr217Ala
Pro201Ser + Gln206Asp + Leu209His + Pro210Glu + Gly211Glu + Lys213Glu + Tyr217Val
Ala200Thr + Leu209Thr + Pro210Asp + Gly215Glu + Ala216Gln + Tyr217Leu + Asn218Gln
Thr208Asn + Leu209Gln + Pro210Glu + Gly211Asn + Gly215Asp + Tyr217Leu + Asn218Ser
Ser204Asp + Thr208Gln + Pro210Glu + Gly211Ser + Ala216Glu + Tyr217Glu + Gly219Pro
Ser204Asp + Thr208Asn + Pro210Glu + Gly211Ser + Asn212Gln + Gly215Asp + Tyr217Glu
Ser204Glu + Pro210Ser + Asn212Gln + Lys213Glu + Tyr214Ser + Gly215Glu + Tyr217Leu
Thr208Asn + Asn212Asp + Lys213Asp + Tyr214Val + Ala216Glu + Tyr217Leu + Thr220Ser
Ser204Glu + Leu209Ser + Pro210Glu + Gly211Asp + Asn212Glu + Tyr214Asn + Tyr217Leu
Ala200Ser + Val203Asn + Leu209Gly + Pro210Gly + Gly215Glu + Tyr217Leu + Asn218Asp
Gly202Asn + Val203Gln + Tyr214Pro + Gly215Glu + Tyr217Leu + Asn218Asp + Gly219Asn
Pro201Gly + Ser204Asp + Gln206Asn + Gly211Glu + Lys213Asp + Tyr214Asp + Tyr217Leu
Gln206Asp + Thr208Asn + Asn212Ser + Lys213Glu + Tyr214His + Ala216Asn + Tyr217Leu
Gly202Gln + Ile205Met + Gln206Glu + Leu209Gln + Lys213Glu + Ala216Asn + Tyr217His
Val203Gly + Gln206Asp + Lys213Asp + Tyr214Ala + Ala216Gly + Tyr217Leu + Gly219Ser
Pro201Gly + Gly202Pro + Gln206Asp + Gly211Glu + Asn212Asp + Gly215Asp + Tyr217Leu
Gly202Pro + Ser204Asp + Gln206Ser + Leu209Val + Lys213Asp + Ala216Glu + Tyr217Leu
Gly202Pro + Val203Cys + Ser204Asp + Gln206Glu + Gly211Asp + Gly215Asp + Tyr217Leu
Pro201Gln + Ser204Glu + Leu209Ser + Pro210Glu + Gly211Asp + Lys213Glu + Tyr217Leu
Ile205Ala + Thr208Ser + Leu209Cys + Asn212Gln + Lys213Glu + Ala216Asp + Tyr217Leu
Pro201Gly + Ile205His + Asn212Glu + Lys213Asp + Tyr214Glu + Tyr217Leu + Gly219Glu
Ala200Pro + Gly202Ser + Ile205Gly + Asn212Glu + Gly215Asp + Tyr217Glu + Asn218Asp
Gly202Pro + Val203Pro + Gln206Glu + Gly211Glu + Lys213Glu + Tyr217Leu + Thr220Gln
Ile205Val + Gly211Asp + Asn212Gln + Lys213Glu + Tyr214Gly + Ala216Glu + Tyr217Leu
Ala200Pro + Pro201Asn + Gly211Asp + Gly215Glu + Ala216Glu + Tyr217Leu + Asn218Asp
Ile205Pro + Gln206Glu + Leu209His + Pro210Asn + Gly215Asp + Tyr217Leu + Gly219Glu
Ser204Glu + Leu209Pro + Lys213Asp + Tyr214Thr + Tyr217Met + Asn218Asp + Gly219Glu
Gly202Pro + Ser204Glu + Gln206Asp + Thr208Asn + Ala216Gln + Tyr217Leu + Thr220Glu
Pro201Asn + Gln206Asn + Lys213Glu + Ala216Glu + Tyr217Leu + Asn218Asp + Gly219Gln
Val203His + Leu209Met + Gly211Asp + Lys213Glu + Gly215Asp + Tyr217Leu + Asn218Glu
Gln206Asp + Leu209Cys + Pro210Asn + Gly211Asp + Gly215Asp + Ala216Pro + Tyr217Leu
Ala200His + Gly202Asn + Val203Asp + Ser204Glu + Gln206Glu + Gly211Asp + Tyr217His
Pro201Ser + Ser204Asp + Ile205Asn + Thr208Asn + Leu209Gly + Tyr217Cys + Thr220Asp
Ala200Asn + Gly202Pro + Ser204Glu + Gly211Ser + Ala216Pro + Tyr217Leu + Thr220Glu
Gly202Ser + Val203Cys + Ser204Asp + Ile205Pro + Gly215Ser + Tyr217Leu + Thr220Asp

TABLE 8-continued

Heptuple Mutation BPN' Variants

Gly202Ser + Val203His + Ser204Asp + Ile205Cys + Tyr217Leu + Asn218Ser + Thr220Glu
Pro201Asn + Gly202Pro + Gln206Asp + Gly211Glu + Gly215Asp + Tyr217Ile + Asn218Asp
Ala200Thr + Ile205Gly + Gln206Glu + Lys213Glu + Tyr214Asp + Tyr217Leu + Thr220Glu
Ala200Ser + Val203Cys + Ser204Asp + Pro210Asp + Gly211Pro + Ala216Glu + Tyr217Leu
Val203Met + Gln206Asp + Thr208Ser + Leu209Gln + Pro210Asp + Gly211Glu + Tyr217Leu
Pro201Ser + Gln206Glu + Leu209Asn + Pro210Glu + Asn212Glu + Tyr214Ser + Tyr217Ala
Thr208Ser + Leu209Asn + Pro210Ser + Tyr214Glu + Gly215Asp + Tyr217Leu + Gly219Glu
Pro201Ser + Gln206Asn + Gly211Asp + Lys213Glu + Gly215Asp + Tyr217Leu + Gly219Glu
Pro201Gln + Ile205Leu + Gln206Asp + Tyr214Asp + Tyr217Leu + Gly219Asp + Thr220Glu
Ala200Gly + Gly202Gln + Ser204Glu + Asn212Glu + Ala216Asp + Tyr217Leu + Gly219Asp
Ile205Cys + Gln206Glu + Pro210Asp + Lys213Asp + Gly215Asn + Tyr217Leu + Asn218Glu
Ala200Asn + Val203Asp + Ser204Glu + Thr208Ser + Pro210Asp + Tyr217Leu + Thr220Glu
Gly202Ser + Thr208Gln + Gly211Glu + Lys213Glu + Gly215Asp + Tyr217Leu + Thr220Asp
Val203Asn + Ser204Glu + Pro210Asn + Gly211Asp + Gly215Glu + Ala216His + Tyr217Leu
Ala200His + Pro201Ser + Thr208Asn + Pro210Glu + Gly211Glu + Tyr217Leu + Asn218Asp
Pro201Gly + Ile205Gly + Leu209Gln + Pro210Asp + Gly211Asp + Tyr217Ser + Gly219Glu
Ala200His + Ile205Ser + Thr208Gln + Pro210Asp + Gly211Asp + Tyr217Leu + Thr220Asp
Pro201Gly + Ile205Pro + Pro210Asp + Gly211Glu + Tyr217Leu + Gly219Gln + Thr220Asp
Pro201Asn + Leu209His + Pro210Ser + Asn212Asp + Tyr217Leu + Asn218Glu + Gly219Glu
Val203Ala + Ser204Asp + Asn212Glu + Lys213Asp + Tyr214Cys + Ala216Gln + Tyr217His
Gly202Asn + Ser204Asp + Asn212Asp + Lys213Glu + Tyr217Leu + Gly219Gln + Thr220Gly
Pro201Asn + Gly202Gln + Ser204Glu + Asn212Glu + Lys213Asp + Tyr214Ala + Tyr217Leu
Pro201Gly + Thr208Asn + Asn212Asp + Lys213Asp + Gly215Ser + Tyr217Leu + Thr220Glu
Ala200His + Gly202Pro + Pro210Gly + Lys213Asp + Tyr214Glu + Tyr217Leu + Thr220Asp
Gly202Gln + Val203Met + Ile205Gly + Gly211Asp + Asn212Glu + Tyr217Leu + Thr220Glu
Ala200Thr + Ile205Met + Leu209His + Gly211Asp + Asn212Asp + Tyr217Leu + Thr220Glu

TABLE 9

Octuple Mutation BPN' Variants

Pro201Gly + Gly202Ser + Ser204Glu + Thr208Ser + Gly211Gln + Tyr214Ser + Gly215Gln + Tyr217Leu
Ala200Gln + Val203Ala + Thr208Gly + Leu209Ser + Asn212Gln + Tyr214Gly + Tyr217Ser + Asn218Glu
Gly202Gln + Ser204Glu + Ile205Ala + Leu209Gln + Tyr214Pro + Ala216Ser + Tyr217Val + Thr220Gln
Ser204Asp + Ile205Met + Thr208Asn + Pro210Ser + Asn212Ser + Tyr214Pro + Gly215Pro + Tyr217Leu
Val203Thr + Ser204Asp + Ile205Asn + Thr208Asn + Leu209Gln + Gly215Gln + Tyr217Leu + Thr220Asn
Pro201Gln + Gly202Asn + Ile205Asn + Gly211Pro + Asn212Glu + Tyr214Val + Tyr217Leu + Gly219Gly
Ala200Asn + Pro201Gln + Ile205Met + Thr208Ser + Gly211Pro + Asn212Glu + Tyr217Leu + Thr220Gln
Gly202Ser + Val203Ser + Thr208Asn + Leu209Ala + Gly215Glu + Tyr217Leu + Asn218Ser + Gly219Ser

TABLE 9-continued

Octuple Mutation BPN' Variants

Gly202Ser + Val203Pro + Ile205Ala + Leu209Asn + Asn212Gln + Gly215Asn + Tyr217Thr + Gly219Asp
Pro201Asn + Leu209Ala + Gly211Pro + Gly215Asn + Ala216Asn + Tyr217Ser + Gly219Asn + Thr220Asp
Pro201Gly + Gly202Ser + Ile205Val + Gly211Ser + Asn212Asp + Gly215Gln + Tyr217Leu + Gly219Pro
Val203Ala + Thr208Pro + Leu209Ser + Pro210Asp + Tyr214Leu + Ala216His + Tyr217Leu + Asn218Ser
Ala200Pro + Pro201Ser + Thr208Asn + Lys213Asp + Ala216Asn + Tyr217Leu + Gly219Pro + Thr220Gln
Pro201Gly + Gly202Ser + Ile205His + Gly211Pro + Asn212Glu + Tyr214Cys + Tyr217Leu + Thr220Asn
Pro201Asn + Gly202Ser + Val203Cys + Leu209Cys + Tyr214Leu + Tyr217Leu + Asn218Ser + Thr220Pro
Ala200Gln + Pro201Gln + Ile205His + Gln206Ser + Lys213Glu + Gly215Asn + Tyr217Leu + Gly219Asn
Ala200Thr + Pro201Gly + Ile205Pro + Gly211Asn + Gly215Asn + Tyr217Leu + Asn218Asp + Gly219Gln
Pro201Ser + Gly202Gln + Val203Thr + Thr208Gln + Gly211Gln + Gly215Ser + Tyr217His + Thr220Gln
Ser204Glu + Ile205Pro + Thr208Gly + Pro210Ser + Ala216Ser + Tyr217Ile + Gly219Pro + Thr220Asn
Pro201Gly + Val203Ala + Gln206Asn + Thr208Gly + Gly211Gln + Asn212Glu + Tyr217Leu + Gly219Asn
Pro201Asn + Gly202Gln + Gln206Asp + Pro210Ser + Tyr214Ser + Gly215Gln + Tyr217Leu + Thr220Gly
Pro201Ser + Thr208Ser + Lys213Glu + Tyr214Asn + Ala216Pro + Tyr217Thr + Gly219Pro + Thr220Gly
Ala200Thr + Pro201Ser + Gly202Asn + Val203Thr + Ser204Asp + Leu209His + Gly215Gln + Tyr217Leu
Ala200His + Gly211Asp + Gly215Gln + Ala216Thr + Tyr217Leu + Asn218Ser + Gly219Asn + Thr220Ser
Pro201Asn + Gly202Asn + Val203Cys + Ile205Leu + Gln206Asn + Thr208Pro + Gly215Pro + Tyr217Leu
Ala200Asn + Pro201Ser + Val203Ala + Thr208Gly + Gly211Pro + Lys213Glu + Tyr217Ile + Thr220Gln
Gln206Asn + Leu209Cys + Gly211Gln + Asn212Gln + Lys213Asp + Ala216Gln + Tyr217Leu + Thr220Gly
Val203Gln + Ser204Asp + Ile205Ala + Gln206Asn + Gly211Gln + Tyr214His + Tyr217Leu + Thr220Pro
Pro201Gln + Gly202Ser + Ser204Asp + Thr208Ser + Leu209His + Pro210Asn + Tyr217Leu + Gly219Pro
Ala200Asn + Gly202Asn + Gln206Asn + Leu209His + Gly211Asn + Tyr214Leu + Tyr217Leu + Thr220Ser
Pro201Gly + Gly202Asn + Ile205Met + Gly211Ser + Asn212Asp + Gly215Asn + Ala216His + Tyr217Ser
Pro201Gly + Gly202Ser + Ile205Val + Thr208Pro + Gly211Asn + Asn212Asp + Tyr217Leu + Asn218Gln
Gly202Pro + Thr208Gly + Leu209Cys + Pro210Ser + Gly211Asn + Tyr217Ala + Asn218Gln + Gly219Asn
Pro201Ser + Val203Pro + Ile205Gly + Gln206Asp + Asn212Ser + Ala216Pro + Tyr217Asn + Gly219Gln
Pro201Asn + Gly202Gln + Val203Ala + Thr208Pro + Tyr214Val + Gly215Asp + Tyr217Leu + Thr220Ser
Ala200Thr + Gly202Gln + Ile205Gln + Leu209Ile + Lys213Asp + Ala216Gly + Tyr217Gln + Gly219Pro
Ala200Ser + Pro201Gln + Gly202Gln + Val203Asn + Ser204Glu + Ala216His + Tyr217Leu + Gly219Pro
Ala200Gly + Ile205Asn + Leu209Gly + Lys213Asp + Gly215Pro + Ala216Pro + Tyr217Leu + Asn218Gln
Pro201Asn + Ser204Asp + Ile205Pro + Pro210Ser + Gly211Pro + Tyr217Leu + Gly219Gln + Thr220Ser
Pro201Asn + Ile205Leu + Gln206Asp + Gly211Ser + Asn212Ser + Ala216Pro + Tyr217Ile + Thr220Ser
Ala200His + Pro201Gln + Gln206Asn + Thr208Gly + Pro210Asp + Gly211Asp + Tyr217Cys + Thr220Asn
Ala200Asn + Ile205Met + Thr208Ser + Pro210Asp + Gly211Glu + Ala216Thr + Tyr217Ser + Gly219Pro
Gly202Pro + Ile205Gln + Thr208Gln + Pro210Asn + Ala216Thr + Tyr217Cys + Asn218Asp + Gly219Asp
Val203Gly + Thr208Asn + Tyr214Pro + Gly215Gln + Tyr217Leu + Asn218Glu + Gly219Glu + Thr220Gln
Pro201Asn + Leu209Met + Asn212Glu + Lys213Asp + Ala216His + Tyr217Leu + Asn218Gln + Thr220Gln
Ala200Gly + Gly202Asn + Ile205His + Leu209Cys + Asn212Asp + Lys213Asp + Tyr217Leu + Thr220Pro

TABLE 9-continued

Octuple Mutation BPN' Variants

Ala200His + Gly202Ser + Thr208Gly + Asn212Asp + Lys213Asp + Ala216Ser + Tyr217Leu + Thr220Ser
Ala200Asn + Pro201Asn + Ile205Gln + Asn212Asp + Lys213Glu + Tyr214Cys + Gly215Ser + Tyr217Leu
Ala200Ser + Pro201Gly + Gly202Gln + Val203Met + Asn212Asp + Lys213Asp + Tyr214Gln + Tyr217Leu
Ala200Gln + Gln206Asn + Thr208Ser + Pro210Gly + Asn212Glu + Lys213Asp + Gly215Gln + Tyr217Leu
Ala200Ser + Gly202Asn + Val203Thr + Gly211Asn + Tyr214Glu + Gly215Glu + Tyr217Leu + Gly219Gln
Pro201Gln + Gly202Gln + Leu209Cys + Gly211Asp + Asn212Glu + Gly215Gln + Tyr217Leu + Gly219Ser
Ala200His + Ile205Ser + Leu209Ile + Pro210Gln + Gly211Asp + Asn212Asp + Tyr214Ser + Tyr217Leu
Pro201Gly + Gly202Asn + Val203Glu + Ile205Leu + Leu209Ala + Pro210Gly + Tyr217Leu + Asn218Glu
Ala200Gly + Val203Asp + Ile205Met + Gly211Asn + Ala216His + Tyr217His + Asn218Glu + Thr220Gln
Leu209Met + Pro210Asp + Gly211Glu + Asn212Glu + Tyr214Cys + Gly215Ser + Tyr217Leu + Gly219Pro
Ser204Glu + Leu209Asn + Pro210Gly + Tyr214Asn + Tyr217Leu + Asn218Asp + Gly219Ser + Thr220Gly
Pro201Gln + Val203His + Ser204Asp + Ile205Val + Leu209Val + Asn212Gln + Tyr217Leu + Asn218Asp
Pro201Gly + Ser204Asp + Thr208Asn + Pro210Ser + Tyr214Cys + Tyr217Leu + Asn218Glu + Thr220Asn
Pro201Asn + Gly202Pro + Ile205Ala + Thr208Pro + Gly211Asp + Lys213Glu + Gly215Gln + Tyr217Leu
Ile205Thr + Gly211Glu + Asn212Gln + Lys213Glu + Gly215Ser + Ala216Ser + Tyr217Val + Thr220Asn
Ala200His + Ser204Asp + Thr208Pro + Gly211Asn + Ala216Glu + Tyr217Leu + Asn218Glu + Thr220Gly
Pro201Ser + Val203Asp + Ser204Asp + Gly211Pro + Gly215Ser + Ala216Glu + Tyr217His + Asn218Asp
Ala200Asn + Pro201Asn + Gln206Asn + Leu209Ala + Pro210Asp + Lys213Asp + Ala216Gly + Tyr217Leu
Ala200Asn + Pro201Gly + Gly202Gln + Ser204Asp + Gln206Asp + Thr208Asn + Asn212Ser + Tyr217Leu
Gly202Asn + Val203Ser + Ser204Glu + Gln206Glu + Leu209Met + Asn212Gln + Tyr217Leu + Gly219Ser
Val203His + Ser204Asp + Gln206Asp + Leu209Thr + Gly215Asn + Tyr217His + Asn218Gln + Thr220Ser
Gly202Ser + Val203Asp + Ile205Cys + Leu209Cys + Tyr214Pro + Tyr217Thr + Gly219Glu + Thr220Gln
Val203Glu + Ser204Asp + Gln206Asp + Thr208Asn + Leu209Gln + Asn212Ser + Tyr217Leu + Asn218Gln
Pro201Ser + Ser204Glu + Gln206Glu + Leu209Ile + Pro210Gln + Tyr214Ser + Gly215Glu + Tyr217Leu
Ser204Asp + Gln206Asp + Thr208Gly + Leu209Met + Pro210Gln + Gly215Asp + Tyr217Leu + Asn218Gln
Gly202Ser + Val203Asn + Ser204Glu + Gln206Glu + Gly211Asn + Gly215Asp + Tyr217Val + Thr220Gln
Gly202Gln + Ile205Met + Pro210Gly + Gly211Asn + Lys213Asp + Gly215Glu + Tyr217Leu + Thr220Pro
Pro201Gly + Gly202Pro + Thr208Gly + Pro210Ser + Tyr214Glu + Ala216Asp + Tyr217Leu + Thr220Ser
Gly202Asn + Val203Ser + Leu209His + Tyr214Glu + Gly215Asn + Ala216Glu + Tyr217Leu + Gly219Ser
Leu209His + Asn212Ser + Lys213Asp + Tyr214Val + Gly215Asp + Ala216Asp + Tyr217Leu + Thr220Asn
Pro201Gly + Val203Gln + Leu209Cys + Pro210Ser + Asn212Glu + Lys213Asp + Gly215Glu + Tyr217Leu
Pro201Asn + Thr208Gly + Leu209Asn + Pro210Glu + Gly211Asn + Lys213Asp + Gly215Glu + Tyr217Leu
Ala200His + Pro201Ser + Gln206Asp + Asn212Ser + Ala216Asp + Tyr217Cys + Asn218Glu + Gly219Glu
Ala200Ser + Pro201Gly + Ser204Glu + Tyr214Ser + Gly215Glu + Ala216Asn + Tyr217Leu + Asn218Asp
Ser204Asp + Thr208Asn + Leu209Cys + Tyr214Cys + Gly215Asp + Ala216Gln + Tyr217Leu + Asn218Asp
Gly202Asn + Val203Asp + Gln206Ser + Leu209Pro + Pro210Gly + Asn212Gln + Tyr217Leu + Thr220Glu
Gly202Gln + Ile205Leu + Asn212Asp + Lys213Glu + Tyr214Asp + Ala216Glu + Tyr217Leu + Thr220Pro
Ala200His + Pro201Gly + Gln206Asp + Thr208Pro + Lys213Asp + Tyr214Val + Ala216Asp + Tyr217Asp

TABLE 9-continued

Octuple Mutation BPN' Variants

Ala200Thr + Val203His + Ile205Met + Leu209Thr + Pro210Asp + Asn212Glu + Gly215Asp + Tyr217Leu
Gly202Asn + Ile205Cys + Asn212Asp + Lys213Glu + Gly215Glu + Ala216Glu + Tyr217Leu + Thr220Gly
Pro201Ser + Val203Asp + Ile205Gln + Gln206Asp + Leu209Met + Pro210Gln + Ala216Ser + Tyr217Leu
Ala200Ser + Gly202Pro + Ser204Asp + Gln206Glu + Leu209Met + Tyr217Leu + Asn218Gln + Gly219Glu
Ala200Gln + Gly202Asn + Ser204Asp + Gln206Glu + Leu209Cys + Tyr214Val + Tyr217Ala + Gly219Glu
Ala200Gly + Gly202Pro + Val203Met + Gln206Asp + Thr208Asn + Leu209Cys + Tyr217Leu + Asn218Glu
Ala200Thr + Pro201Gln + Gln206Asp + Pro210Ser + Gly211Ser + Asn212Gln + Tyr217Leu + Asn218Asp
Ala200Asn + Gly202Ser + Lys213Asp + Tyr214Ile + Gly215Asp + Tyr217Glu + Gly219Asn + Thr220Gly
Ala200His + Val203Asp + Gln206Ser + Leu209Asn + Gly215Glu + Ala216Ser + Tyr217Leu + Asn218Asp
Gln206Asp + Leu209His + Pro210Asp + Gly211Glu + Lys213Asp + Gly215Pro + Tyr217Leu + Gly219Asn
Ala200Asn + Pro201Gly + Thr208Pro + Leu209His + Pro210Asp + Lys213Asp + Tyr214Glu + Tyr217Glu
Gly202Asn + Gln206Asp + Pro210Asn + Tyr214Glu + Gly215Glu + Tyr217Leu + Gly219Asp + Thr220Pro
Pro201Gln + Val203Cys + Ser204Asp + Gln206Glu + Leu209Thr + Pro210Asp + Gly215Asp + Tyr217Leu
Val203Gly + Gln206Glu + Asn212Glu + Lys213Glu + Tyr214His + Ala216Gln + Tyr217Leu + Thr220Gln
Gly202Pro + Val203Gly + Gln206Ser + Pro210Glu + Gly211Gln + Asn212Gln + Lys213Asp + Tyr217Glu
Pro201Gly + Val203Glu + Ile205Asn + Lys213Asp + Gly215Ser + Ala216Asp + Tyr217Leu + Asn218Glu
Thr208Ser + Gly211Ser + Asn212Asp + Tyr214Thr + Gly215Asp + Ala216Glu + Tyr217Leu + Thr220Pro
Ala200Ser + Pro201Ser + Thr208Gly + Asn212Glu + Lys213Asp + Tyr214Ala + Ala216Glu + Tyr217Leu
Pro201Gln + Thr208Gly + Gly211Glu + Asn212Glu + Lys213Asp + Tyr214His + Tyr217Leu + Asn218Asp
Pro201Gly + Val203Glu + Ser204Asp + Gly211Pro + Asn212Gln + Lys213Asp + Tyr217Leu + Asn218Glu
Ser204Asp + Leu209Gln + Pro210Asp + Lys213Glu + Gly215Glu + Tyr217Leu + Asn218Ser + Gly219Asp
Pro201Asn + Ser204Asp + Gln206Asp + Gly211Gln + Gly215Asp + Ala216Gly + Tyr217Thr + Thr220Asp
Ser204Glu + Thr208Asn + Asn212Gln + Lys213Glu + Gly215Glu + Ala216Asn + Tyr217Val + Asn218Glu
Pro201Ser + Ser204Glu + Thr208Ser + Gly211Asn + Gly215Asp + Tyr217Leu + Asn218Gln + Gly219Asp
Ala200Ser + Ile205Ser + Pro210Ser + Gly215Glu + Ala216Asn + Tyr217Leu + Asn218Asp + Gly219Asn
Ser204Asp + Ile205Thr + Gln206Glu + Thr208Gly + Lys213Asp + Tyr214Gly + Tyr217Leu + Asn218Glu
Ala200Asn + Thr208Gln + Asn212Asp + Lys213Glu + Tyr214Asp + Gly215Gln + Tyr217Leu + Asn218Glu
Pro201Gly + Leu209Pro + Pro210Asn + Gly211Gln + Asn212Glu + Tyr217Glu + Asn218Glu + Gly219Glu
Pro201Gln + Ile205Ala + Gln206Glu + Lys213Asp + Tyr214Leu + Tyr217His + Gly219Asn + Thr220Asn
Ala200Gly + Pro201Gly + Gly202Asn + Ile205Ala + Gln206Asp + Pro210Ser + Lys213Glu + Tyr217Ile
Pro201Asn + Gly202Gln + Gln206Asp + Leu209Gln + Lys213Asp + Tyr214Gly + Gly215Pro + Tyr217Ala
Ala200Thr + Gln206Glu + Leu209Cys + Lys213Glu + Tyr217Leu + Asn218Ser + Gly219Gln + Thr220Pro
Gly202Pro + Ser204Asp + Gln206Ser + Gly211Asn + Lys213Glu + Ala216Glu + Tyr217Leu + Gly219Gln
Ala200Asn + Ser204Glu + Ile205Thr + Gln206Asp + Thr208Gln + Gly211Asp + Gly215Asp + Tyr217Leu
Ala200Pro + Val203Asp + Gln206Ser + Gly215Glu + Ala216Asp + Tyr217Thr + Gly219Asn + Thr220Glu
Ala200Pro + Pro201Ser + Thr208Asn + Pro210Gln + Asn212Asp + Gly215Asp + Tyr217Leu + Thr220Asn
Pro201Gln + Pro210Ser + Asn212Gln + Lys213Glu + Gly215Pro + Ala216Asp + Tyr217Leu + Gly219Asn
Pro201Gly + Gly202Asn + Val203Ser + Leu209Met + Lys213Asp + Ala216Asp + Tyr217Leu + Gly219Pro

TABLE 9-continued

Octuple Mutation BPN' Variants

Gly202Gln + Val203Asp + Pro210Asp + Asn212Glu + Lys213Asp + Tyr214Ser + Gly215Ser + Tyr217Gly
Ala200Ser + Pro201Asn + Ser204Glu + Thr208Ser + Pro210Asp + Asn212Glu + Lys213Asp + Tyr217Leu
Pro201Gly + Gly202Pro + Ser204Asp + Pro210Glu + Gly211Pro + Asn212Asp + Lys213Asp + Tyr217Leu
Ala200Asn + Pro210Asn + Gly211Asp + Asn212Gln + Lys213Glu + Ala216Asp + Tyr217Leu + Gly219Ser
Gly202Pro + Thr208Gln + Leu209His + Pro210Gly + Gly211Glu + Gly215Asp + Ala216Glu + Tyr217Leu
Pro201Asn + Ser204Glu + Ile205Met + Gln206Asp + Pro210Gly + Lys213Glu + Tyr214Met + Tyr217Leu
Pro201Ser + Val203Ser + Ile205Pro + Gly211Asn + Lys213Asp + Ala216Glu + Tyr217Leu + Asn218Asp
Gly202Gln + Ser204Asp + Leu209Ser + Asn212Glu + Tyr214Leu + Gly215Asp + Tyr217Gln + Asn218Asp
Gly202Pro + Val203Cys + Ser204Glu + Gln206Glu + Pro210Asp + Ala216Asn + Tyr217Leu + Asn218Glu
Pro201Ser + Val203Asp + Pro210Asn + Lys213Asp + Gly215Ser + Tyr217Leu + Gly219Glu + Thr220Glu
Val203Glu + Ser204Asp + Ile205Cys + Gly211Asp + Gly215Gln + Tyr217Leu + Gly219Glu + Thr220Ser
Pro201Ser + Val203Asp + Ser204Glu + Leu209Ala + Lys213Asp + Tyr214Asn + Tyr217Leu + Gly219Asp
Pro201Gln + Ile205Pro + Gly211Glu + Asn212Glu + Tyr214Asp + Ala216Arg + Tyr217Leu + Asn218Asp
Pro210Ser + Gly211Gln + Lys213Asp + Gly215Glu + Ala216Glu + Tyr217Leu + Asn218Ser + Thr220Glu
Ala200Gln + Ser204Glu + Gln206Asn + Asn212Gln + Tyr214Pro + Ala216His + Tyr217Leu + Thr220Glu
Ala200Thr + Pro201Ser + Ser204Asp + Ile205His + Leu209Asn + Tyr214Pro + Tyr217Leu + Thr220Glu
Pro201Asn + Val203Ser + Ser204Asp + Gln206Glu + Asn212Glu + Lys213Asp + Tyr217Leu + Asn218Ser
Pro201Asn + Gly202Pro + Gln206Asp + Gly211Glu + Asn212Gln + Gly215Asp + Tyr217Ile + Asn218Asp
Val203Glu + Leu209Cys + Pro210Ser + Gly211Glu + Lys213Glu + Tyr214Cys + Gly215Glu + Tyr217Thr
Ser204Asp + Thr208Asn + Asn212Ser + Lys213Glu + Tyr214Glu + Tyr217Leu + Asn218Glu + Gly219Ser
Pro201Gly + Gly202Ser + Ser204Asp + Thr208Ser + Leu209Gln + Asn212Glu + Gly215Asp + Tyr217Leu
Gly202Ser + Gly211Glu + Lys213Glu + Tyr214Leu + Ala216Asp + Tyr217Leu + Asn218Glu + Gly219Gln
Gly202Pro + Leu209Met + Pro210Gly + Tyr214Glu + Gly215Glu + Tyr217Leu + Gly219Asp + Thr220Ser
Val203Glu + Gln206Asp + Thr208Asn + Asn212Asp + Lys213Glu + Gly215Gln + Tyr217Leu + Asn218Ser
Pro201Asn + Val203Glu + Gln206Glu + Leu209Ile + Asn212Glu + Lys213Asp + Tyr214Ala + Tyr217Leu
Gly202Ser + Gln206Asp + Asn212Gln + Lys213Asp + Ala216Gln + Tyr217Asn + Asn218Glu + Gly219Pro
Pro201Asn + Gln206Asp + Pro210Ser + Lys213Glu + Gly215Pro + Tyr217Cys + Asn218Asp + Gly219Asn
Val203Met + Gln206Asp + Gly211Pro + Asn212Asp + Tyr214Gly + Ala216Glu + Tyr217Leu + Gly219Gln
Ala200Asn + Gly202Gln + Gln206Asp + Leu209Met + Asn212Glu + Gly215Ser + Ala216Asp + Tyr217Leu
Ser204Glu + Ile205Gly + Leu209Met + Pro210Gln + Gly215Glu + Tyr217Leu + Gly219Gln + Thr220Glu
Thr208Gly + Leu209Gln + Gly211Asn + Asn212Gln + Lys213Asp + Tyr214Asp + Tyr217Leu + Asn218Asp
Ala200His + Val203Asn + Gln206Asn + Lys213Glu + Tyr214Asp + Gly215Ser + Tyr217Leu + Asn218Asp
Gln206Glu + Gly211Glu + Asn212Glu + Tyr214Ser + Gly215Ser + Ala216Glu + Tyr217Leu + Gly219Gln
Ala200Gln + Gly202Asn + Val203Pro + Gly211Asp + Gly215Asp + Ala216Ser + Tyr217Leu + Thr220Gly
Pro201Gln + Thr208Gln + Pro210Glu + Lys213Glu + Gly215Gln + Ala216Glu + Tyr217Leu + Gly219Glu
Ala200Thr + Gly202Ser + Ser204Glu + Ile205Leu + Pro210Asp + Tyr214Asp + Tyr217Met + Gly219Ser
Ala200Gln + Leu209Pro + Pro210Glu + Tyr214His + Gly215Pro + Tyr217Leu + Asn218Glu + Gly219Glu
Gln206Ser + Pro210Ser + Gly211Gln + Lys213Glu + Gly215Asn + Tyr217Leu + Gly219Asp + Thr220Glu

TABLE 9-continued

Octuple Mutation BPN' Variants

Pro201Gly + Gly202Pro + Thr208Asn + Pro210Asp + Tyr214His + Tyr217Leu + Gly219Asp + Thr220Asp
Ala200Pro + Gly202Ser + Val203Gln + Leu209Asn + Lys213Asp + Tyr217Leu + Gly219Asp + Thr220Asp
Pro201Asn + Leu209His + Pro210Ser + Asn212Asp + Lys213Asp + Tyr217Leu + Asn218Glu + Gly219Glu
Gly202Pro + Val203Glu + Thr208Pro + Asn212Asp + Lys213Glu + Gly215Pro + Tyr217Gly + Gly219Ser
Ile205Pro + Gln206Ser + Gly211Pro + Asn212Glu + Lys213Asp + Tyr214Leu + Tyr217Cys + Thr220Glu
Ile205Ala + Thr208Pro + Leu209Cys + Asn212Asp + Lys213Asp + Tyr217Leu + Asn218Ser + Thr220Asp
Gly202Gln + Gln206Ser + Asn212Asp + Lys213Glu + Tyr217Leu + Asn218Gln + Gly219Gln + Thr220Glu
Pro201Gln + Val203Asp + Ser204Glu + Ile205Ser + Lys213Asp + Ala216Ser + Tyr217Leu + Thr220Ser
Gly202Asn + Val203Glu + Ser204Glu + Ile205Thr + Asn212Glu + Ala216Pro + Tyr217Thr + Gly219Gln
Gly202Pro + Val203Gly + Ile205Gly + Pro210Gln + Gly211Asp + Asn212Asp + Ala216Asp + Tyr217Leu
Gly202Pro + Val203Met + Gln206Asp + Leu209Thr + Asn212Asp + Tyr217Leu + Asn218Asp + Gly219Asp
Val203Met + Ser204Glu + Leu209Gly + Gly211Asp + Asn212Asp + Gly215Gln + Tyr217Ile + Thr220Pro
Ile205Val + Thr208Pro + Gly211Glu + Asn212Asp + Ala216Ser + Tyr217Leu + Asn218Ser + Gly219Glu
Ala200Thr + Ser204Asp + Gln206Glu + Thr208Pro + Leu209Ile + Pro210Asp + Tyr214Ala + Tyr217Leu
Gly202Pro + Val203Ser + Ser204Glu + Gln206Asp + Pro210Asp + Gly215Pro + Tyr217Leu + Thr220Pro
Gly202Ser + Gly211Gln + Asn212Asp + Lys213Asp + Ala216Asp + Tyr217Leu + Gly219Asp + Thr220Gln
Ala200Pro + Val203Ser + Ser204Glu + Pro210Asp + Gly215Glu + Ala216Ser + Tyr217Leu + Gly219Asp
Ala200Gln + Pro201Asn + Ile205Thr + Pro210Asp + Gly211Asp + Gly215Asp + Tyr217Leu + Gly219Glu
Ala200Ser + Val203Glu + Leu209Asn + Pro210Glu + Asn212Gln + Tyr217Leu + Asn218Glu + Gly219Glu
Pro201Asn + Ser204Asp + Gln206Asp + Thr208Ser + Asn212Asp + Tyr217Leu + Gly219Glu + Thr220Gln

TABLE 10

Nonuple Mutation BPN' Variants

Ala200His + Ile205Val + Thr208Gly + Asn212Ser + Tyr214Thr + Gly215Gln + Ala216Gly + Tyr217Leu + Asn218Ser
Ala200Ser + Pro201Ser + Gly202Pro + Leu209Cys + Pro210Gln + Asn212Ser + Tyr214Pro + Ala216Thr + Tyr217Leu
Ala200Gln + Pro201Asn + Ser204Asp + Ile205Leu + Leu209Ile + Pro210Gln + Gly211Pro + Tyr214Thr + Tyr217Leu
Ala200Ser + Pro201Gly + Gly202Gln + Ile205His + Thr208Gln + Leu209Gly + Pro210Ser + Lys213Glu + Tyr217Thr
Ala200Pro + Gly202Asn + Val203Gln + Ile205Val + Leu209Cys + Gly211Asn + Tyr217Leu + Asn218Gln + Gly219Asn
Pro201Asn + Gly202Asn + Val203Cys + Ile205Leu + Gln206Asn + Thr208Pro + Gly215Pro + Tyr217Leu + Gly219Glu
Gly202Gln + Val203Asn + Gln206Ser + Thr208Asn + Leu209Met + Gly215Asn + Tyr217Leu + Gly219Asn + Thr220Gln
Ala200Asn + Pro201Gln + Gly202Pro + Ile205His + Pro210Asn + Asn212Ser + Lys213Asp + Gly215Ser + Tyr217Leu
Ala200Thr + Val203Gly + Ile205Thr + Thr208Gly + Leu209Val + Pro210Gln + Tyr214Glu + Ala216Gly + Tyr217Val
Ala200Pro + Pro201Gly + Gly202Gln + Thr208Pro + Pro210Glu + Asn212Gln + Gly215Pro + Ala216His + Tyr217Leu
Val203His + Ile205Cys + Pro210Gln + Gly211Gln + Asn212Glu + Gly215Pro + Tyr217Ile + Asn218Gln + Gly219Ser
Ala200Gly + Pro201Ser + Val203Met + Ile205Met + Gln206Ser + Leu209Ile + Pro210Asn + Tyr217Leu + Gly219Asn
Ala200Pro + Gly202Ser + Ile205Val + Gln206Glu + Pro210Ser + Tyr214Gln + Glyg215Gln + Tyr217Leu + Asn218Ser
Ala200Gln + Pro201Ser + Gly202Gln + Ile205Met + Asn212Gln + Lys213Glu + Ala216Gly + Tyr217Leu + Gly219Asn
Ala200Asn + Pro201Ser + Val203Pro + Ile205Leu + Leu209Gln + Pro210Gln + Tyr217Leu + Asn218Gln + Gly219Glu

TABLE 10-continued

Nonuple Mutation BPN' Variants

Ala200Gln + Gly202Ser + Ile205Ser + Pro210Asn + Tyr214Ser + Ala216Ser + Tyr217Leu + Gly219Glu + Thr220Ser
Pro201Gly + Ser204Asp + Gln206Ser + Gly211Ser + Asn212Gln + Gly215Asn + Ala216Thr + Tyr217Leu + Thr220Pro
Ala200Gly + Ser204Glu + Ile205Gly + Leu209Gln + Gly211Asn + Tyr214Ala + Gly215Pro + Tyr217Leu + Asn218Ser
Pro201Gly + Gly202Ser + Ile205Thr + Leu209Thr + Lys213Asp + Tyr214Pro + Gly215Gln + Gly219Ser
Gly202Pro + Val203Cys + Ser204Asp + Leu209Pro + Tyr214Thr + Gly215Pro + Tyr217Leu + Asn218Gln + Gly219Pro
Pro201Gly + Gly202Asn + Gln206Ser + Leu209Thr + Lys213Asp + Tyr214Ala + Ala216Gln + Tyr217Leu + Gly219Pro
Ala200His + Pro201Asn + Val203Asn + Ile205Met + Thr208Pro + Gly211Pro + Asn212Gln + Tyr217Leu + Asn218Asp
Pro201Gly + Gly202Asn + Thr208Ser + Leu209Ala + Pro210Asp + Gly211Asp + Tyr214Ser + Tyr217Leu + Asn218Gln
Pro201Ser + Val203Gly + Thr208Asn +Pro210Gln + Tyr214Pro + Tyr217Ile + Asn218Glu + Gly219Glu + Thr220Gln
Val203Asn + Ile205Ala + Gln206Ser + Thr208Asn + Leu209Gly + Asn212Glu + Lys213Glu + Tyr217Leu + Asn218Gln
Gly202Pro + Ile205Met + Thr208Ser + Pro210Asn + Asn212Asp + Lys213Glu + Tyr217Leu + Asn218Gln + Thr220Gly
Gly202Ser + Val203Asp + Ser204Asp + Pro210Asn + Gly211Gln + Gly215Ser + Ala216Thr + Tyr217Leu + Thr220Asn
Ala200Gly + Gly202Ser + Val203Asn + Leu209Val + Gly211Asp + Asn212Asp + Lys213Asp + Tyr214Thr + Tyr217Leu
Pro201Asn + Val203Ala + Ser204Glu + Leu209Gln + Tyr214Pro + Ala216Glu + Tyr217Asp + Asn218Gln + Thr220Asn
Ala200Gly + Gly202Asn + Ser204Asp + Thr208Ser + Leu209Met + Tyr214His + Ala216Asp + Tyr217Leu + Gly219Ser
Ala200Asn + Ser204Glu + Ile205Pro + Tyr214Met + Gly215Pro + Ala216Asp + Tyr217Leu + Gly219Gln + Thr220Asn
Pro201Gln + Ser204Glu + Pro210Ser + Asn212Gln + Tyr214Ala + Ala216Pro + Tyr217Leu + Asn218Glu + Thr220Gly
Gly202Gln + Ser204Glu + Ile205Ser + Leu209Gly + Pro210Gln + Ala216Gln + Tyr217Leu + Asn218Asp + Gly219Asn
Ala200Gly + Gly202Ser + Val203Cys + Gln206Ser + Asn212Asp + Lys213Glu + Tyr214Asp + Ala216Gly + Tyr217Leu
Pro201Ser + Gly202Pro + Val203Thr + Ile205Pro + Gln206Asp + Pro210Gly + Tyr214Thr + Gly215Glu + Tyr217Leu
Gly202Asn + Ser204Glu + Ile205Gly + Gln206Asp + Tyr214Gln + Ala216Asp + Tyr217Leu + Gly219Pro + Thr220Pro
Ala200Gln + Val203His + Ser204Glu + Gln206Ser + Leu209Pro + Gly215Ser + Tyr217Asp + Asn218Ser + Thr220Gly
Val203Gln + Ile205Thr + Gln206Ser + Thr208Asn + Pro210Gln + Gly211Asp + Lys213Asp + Tyr217Ala + Thr220Asn
Ala200Ser + Pro201Asn + Ile205Gly + Gly211Glu + Lys213Glu + Ala216Gly + Tyr217Ala + Gly219Gln + Thr220Gln
Pro201Asn + Gln206Asn + Pro210Gly + Gly211Glu + Asn212Ser + Lys213Glu + Tyr214His + Tyr217Leu + Gly219Ser
Pro201Gly + Val203Ser + Ile205Cys + Thr208Gly +Leu209Ser + Pro210Glu + Asn212Glu + Ala216Thr + Tyr217Leu
Pro201Asn + Gly202Gln + Ser204Asp + Gln206Glu + Asn212Gln + Gly215Asp + Ala216Asp + Tyr217Leu + Asn218Ser
Pro201Gly + Ser204Asp + Gln206Ser + Leu209Asn + Tyr214Val + Ala216Asp + Tyr217Leu + Asn218Asp + Thr220Gly
Pro201Ser + Thr208Gln + Leu209Ser + Pro210Glu + Lys213Glu + Tyr214Ala + Gly215Asn + Tyr217Leu + Asn218Gln
Ala200His + Pro201Ser + Val203Glu + Ser204Glu + Gln206Ser + Leu209Pro + Gly215Gln + Ala216Glu + Tyr217Thr
Ser204Asp + Gln206Ser + Thr208Asn + Leu209Thr + Pro210Ser + Asn212Gln + Tyr217Gln + Asn218Asp + Gly219Glu
Gly202Ser + Val203Pro + Ser204Asp + Thr208Pro + Leu209Ala + Ala216Thr + Tyr217Leu + Asn218Asp + Gly219Glu
Ser204Glu + Thr208Gln + Leu209Val + Pro210Asn + Tyr214Met + Gly215Glu + Ala216Glu + Tyr217Leu + Gly219Gln
Pro201Asn + Gly202Ser + Ser204Glu + Gln206Glu + Tyr214Gln + Ala216His + Tyr217Leu + Gly219Gln + Thr220Gln
Ala200Ser + Val203His + Ser204Asp + Gln206Asp + Thr208Gln + Gly211Asn + Ala216Asn + Tyr217Leu + Asn218Gln
Ala200Gln + Pro201Ser + Gly202Pro + Gln206Asp + Pro210Asn + Asn212Gln + Gly215Glu + Tyr217Glu + Gly219Asn
Val203Gln + Ile205Asn + Thr208Pro + Gly211Glu + Lys213Glu + Tyr214Asp + Ala216Ser + Tyr217Leu + Gly219Asn
Ala200Gln + Gly202Asn + Val203Glu + Ser204Glu + Gln206Asp + Thr208Gln + Gly211Asn + Tyr217Pro + Asn218Gln
Pro201Gly + Val203Glu + Ser204Asp + Gln206Asp + Thr208Asn + Leu209Gln + Asn212Ser + Tyr217Leu + Asn218Gln
Ala200Gln + Pro201Asn + Val203Glu + Thr208Ser + Gly215Asn + Ala216Asp + Tyr217Leu + Asn218Glu + Thr220Pro
Ala200Gln + Ser204Glu + Ile205Cys + Gln206Glu + Pro210Gln + Gly215Glu + Ala216Asn + Tyr217Leu + Thr220Gly
Ala200Gln + Ser204Asp + Ile205Leu + Gln206Asp + Asn212Ser + Gly215Asp + Ala216Ser + Tyr217Leu + Gly219Pro
Ala200Gly + Thr208Gly + Leu209His + Lys213Asp + Tyr214Val + Gly215Asp + Ala216His + Tyr217Leu + Thr220Asn
Pro201Ser + Gln206Asn + Thr208Gln + Leu209Gly + Asn212Ser + Lys213Asp + Gly215Glu + Ala216His + Tyr217Leu
Ala200Thr + Gly202Ser + Val203Cys + Ser204Glu + Ile205Thr + Tyr217Leu + Asn218Asp + Gly219Asp + Thr220Glu
Ala200His + Pro201Gln + Gly202Asn + Val203Asp + Gln206Glu + Pro210Ser + Ala216Glu + Tyr217Leu + Thr220Asn
Pro201Asn + Gly202Glu + Gln206Glu + Leu209Thr + Pro210Ser + Asn212Gln + Lys213Glu + Tyr214Gln + Tyr217Leu
Ala200Pro + Pro201Gln + Thr208Asn + Pro210Asn + Tyr214His + Gly215Glu + Ala216Glu + Tyr217Leu + Asn218Asp
Gly202Gln + Val203Met + Ile205Leu + Gln206Asp + Lys213Glu + Tyr214Cys + Gly215Asp + Ala216Gln + Tyr217Leu
Gln206Glu + Thr208Gln + Leu209Thr + Pro210Asn + Lys213Asp + Tyr214Asn + Gly215Asp + Tyr217Leu + Asn218Gln
Ala200Asn + Pro201Ser + Ile205Gln + Gln206Asn + Pro210Asp + Gly211Pro + Tyr214Gly + Tyr217Ser + Thr220Asn
Ala200Gly + Ser204Asp + Ile205His + Gln206Glu + Leu209Gln + Gly211Gln + Tyr214Asp + Gly215Asn + Tyr217Glu
Ala200Ser + Gly202Pro + Val203Ala + Ser204Glu + Thr208Ser + Gly211Ser + Tyr217Leu + Asn218Glu + Thr220Glu
Pro201Gln + Gly202Ser + Val203Gly + Ser204Asp + Ile205Cys + Tyr214Met + Ala216Glu + Tyr217Leu + Gly219Asp
Pro201Asn + Ile205His + Pro210Gln + Gly211Ser + Tyr214Asp + Gly215Asp + Ala216Glu + Tyr217Leu + Asn218Glu
Ala200Pro + Pro201Ser + Val203Gly + Ser204Asp + Ile205Ala + Gly211Asn + Tyr217Leu + Asn218Gln + Gly219Glu
Ala200His + Gly202Ser + Ser204Glu + Gln206Asp + Asn212Ser + Tyr214Glu + Tyr217Gly + Asn218Gln + Thr220Gly
Pro201Ser + Val203Ser + Ser204Glu + Leu209Ala + Asn212Gln + Gly215Asp + Tyr217Leu + Asn218Glu + Gly219Asp
Ala200Gln + Pro201Gln + Gly202Pro + Ser204Glu + Ile205Met + Gln206Asp + Leu209Ser + Tyr217Leu + Gly219Asp
Pro201Asn + Gln206Asp + Gly211Ser + Asn212Ser + Gly215Pro + Ala216Pro + Tyr217Leu + Asn218Asp + Thr220Ser
Ala200His + Pro201Gln + Gly202Pro + Gln206Asp + Thr208Asn + Leu209Met + Tyr214Ser + Tyr217Leu + Asn218Glu
Ala200Gly + Gly202Pro + Val203Asp + Gln206Glu + Gly211Gln + Tyr214Asp + Gly215Asp + Tyr217Leu + Thr220Gly
Gly202Gln + Val203Cys + Thr208Asn + Gly211Glu + Lys213Asp + Gly215Asp + Ala216Asp + Tyr217Leu + Thr220Gln
Ala200Ser + Gln206Asp + Gly211Asp + Asn212Asp + Lys213Glu + Tyr214Pro + Tyr217Gly + Gly219Pro + Thr220Gln
Ala200Pro + Leu209His + Pro210Glu + Asn212Glu + Lys213Asp + Ala216Asp + Tyr217Leu + Gly219Gln + Thr220Asn
Leu209Ser + Pro210Ser + Gly211Asp + Asn212Glu + Lys213Asp + Tyr214Val + Gly215Gln + Ala216Asp + Tyr217Leu
Val203Ser + Ile205Met + Leu209Thr + Gly215Asp + Ala216Thr + Tyr217Leu + Asn218Asp + Gly219Asp + Thr220Asp
Val203Ala + Gln206Glu + Leu209Thr + Pro210Glu + Gly211Glu + Asn212Gln + Tyr214Glu + Tyr217Pro + Thr220Ser
Ala200Thr + Gly202Pro + Ser204Glu + Leu209Gln + Asn212Glu + Tyr214Glu + Gly215Asp + Tyr217Leu + Asn218Ser
Pro201Gln + Gly202Ser + Ser204Asp + Ile205Ala + Gln206Asp + Thr208Gln + Pro210Asn + Lys213Glu + Tyr217Asp
Ala200Thr + Val203Met + Thr208Gln + Tyr214Ile + Gly215Asp + Ala216Glu + Tyr217Leu + Asn218Ser + Gly219Asp
Ala200Thr + Pro201Asn + Gly202Gln + Ile205Met + Pro210Asn + Asn212Glu + Tyr214Glu + Ala216Glu + Tyr217Leu
Gly202Pro + Ser204Glu + Ile205Ser + Pro210Glu + Asn212Ser + Ala216Asp + Tyr217Asp + Gly219Ser + Thr220Pro
Pro201Gln + Ile205Met + Gln206Asp + Thr208Pro + Gly211Asn + Asn212Asp + Lys213Asp + Tyr217Leu + Asn218Gln
Pro201Gly + Gly202Ser + Ile205His + Gln206Asp + Thr208Ser + Pro210Gln + Asn212Asp + Lys213Asp + Tyr217Leu
Pro201Gln + Val203Gln + Ile205Gly + Gln206Glu + Leu209Ala + Asn212Asp + Lys213Glu + Tyr214Leu + Tyr217Leu

TABLE 10-continued

Nonuple Mutation BPN' Variants

Ala200Thr + Gln206Asn + Leu209Asn + Pro210Glu + Gly215Glu + Ala216Asp + Tyr217Leu + Asn218Asp + Gly219Asn
Ala200Gly + Gly202Asn + Val203Asn + Ser204Asp + Pro210Gly + Lys213Glu + Tyr217Asp + Asn218Glu + Gly219Asn
Ala200His + Ser204Asp + Ile205Asn + Gln206Ser + Thr208Gln + Lys213Glu + Gly215Glu + Tyr217Leu + Asn218Ser
Pro201Ser + Ser204Asp + Ile205Asn + Thr208Asn + Leu209Gln + Gly211Pro + Lys213Asp + Gly215Glu + Tyr217Leu
Val203Gly + Gln206Asp + Thr208Gln + Pro210Asn + Asn212Gln + Lys213Glu + Tyr214Glu + Tyr217Leu + Asn218Asp
Ser204Asp + Gln206Asn + Leu209Val + Asn212Glu + Lys213Asp + Tyr214Met + Gly215Asp + Tyr217Leu + Thr220Gly
Pro201Asn + Gly202Asn + Val203Gly + Ile205His + Thr208Gly + Asn212Asp + Gly215Glu + Ala216Asp + Tyr217Leu
Ser204Asp + Ile205Val + Pro210Gln + Asn212Gln + Lys213Glu + Gly215Glu + Ala216Gly + Tyr217Leu + Asn218Glu
Pro201Asn + Val203Gln + Ser204Glu + Asn212Gln + Lys213Glu + Gly215Asp + Tyr217Leu + Asn218Glu + Thr220Gln
Ala200Gly + Pro201Gln + Gly202Pro + Val203Gly + Ile205Asn + Gln206Glu + Thr208Gly + Lys213Asp + Tyr217Asp
Ala200Gly + Gly202Asn + Val203Asn + Thr208Pro + Leu209Ile + Tyr214Pro + Gly215Asp + Tyr217Leu + Asn218Glu
Val203Cys + Ser204Asp + Ile205Ser + Gln206Asp + Gly211Asn + Lys213Glu + Tyr217Leu + Asn218Asp + Thr220Asn
Thr208Gly + Leu209Met + Gly211Pro + Lys213Glu + Tyr214Val + Gly215Asp + Ala216Glu + Tyr217Leu + Gly219Glu
Ser204Glu + Ile205Ser + Gln206Asp + Leu209Cys + Gly211Gln + Asn212Asp + Ala216Asp + Tyr217Thr + Asn218Gln
Pro201Asn + Gly202Gln + Val203Asn + Ile205His + Gln206Glu + Tyr214Gly + Tyr217Leu + Asn218Glu + Thr220Asp
Ser204Asp + Ile205Gln + Leu209Thr + Pro210Gly + Tyr214Met + Gly215Glu + Tyr217Asn + Gly219Glu + Thr220Asp
Ala200Thr + Gln206Glu + Pro210Asn + Gly211Asp + Lys213Asp + Ala216Asp + Tyr217Leu + Asn218Ser + Thr220Ser
Ala200Thr + Pro201Gln + Gly202Pro + Gln206Asp + Asn212Ser + Lys213Asp + Tyr214Ile + Tyr217Leu + Thr220Asn
Ala200His + Pro201Asn + Gln206Asp + Thr208Pro + Asn212Ser + Lys213Glu + Tyr214Leu + Ala216His + Tyr217Leu
Ala200His + Ser204Asp + Ile205Thr + Thr208Ser + Pro210Asn + Lys213Glu + Gly215Ser + Ala216Glu + Tyr217Leu
Ala200Pro + Gly202Asn + Thr208Asn + Pro210Asn + Asn212Gln + Lys213Glu + Tyr214Leu + Ala216Asp + Tyr217Leu
Gly202Gln + Thr208Gln + Leu209His + Pro210Asp + Asn212Asp + Lys213Asp + Tyr214Gly + Tyr217Leu + Asn218Asp
Ala200Ser + Pro201Gly + Gln206Ser + Pro210Glu + Asn212Glu + Lys213Asp + Gly215Gln + Tyr217Leu + Gly219Glu
Pro201Ser + Thr208Pro + Pro210Asp + Asn212Asp + Lys213Glu + Tyr214Gln + Gly215Asn + Tyr217Leu + Asn218Glu
Ser204Glu + Pro210Glu + Gly211Gln + Asn212Asp + Lys213Glu + Tyr214Gln + Tyr217Leu + Asn218Ser + Thr220Pro
Val203Pro + Ser204Asp + Gln206Ser + Leu209Pro + Pro210Asp + Gly211Asn + Asn212Glu + Lys213Asp + Tyr217Pro
Val203Asn + Ser204Glu + Ile205Asn + Leu209Gly + Pro210Asp + Asn212Asp + Lys213Glu + Tyr214Val + Tyr217Leu
Gly202Ser + Ile205Leu + Gln206Glu + Pro210Gln + Gly211Asp + Lys213Glu + Ala216Asn + Tyr217Leu + Thr220Pro
Ala200Thr + Gly202Ser + Gly211Pro + Asn212Asp + Lys213Glu + Tyr214Cys + Gly215Asp + Tyr217Met + Asn218Asp
Pro201Gln + Ser204Glu + Leu209Met + Gly211Asp + Lys213Asp + Gly215Glu + Tyr217Leu + Asn218Ser + Thr220Gln
Gly202Pro + Val203Ala + Ile205Thr + Gln206Asp + Leu209Gln + Pro210Asp + Ala216Asp + Tyr217Leu + Asn218Asp
Ala200Gly + Pro201Gln + Ser204Glu + Ile205Thr + Leu209Val + Gly211Glu + Ala216Glu + Tyr217Leu + Asn218Asp
Ser204Glu + Ile205Val + Gln206Glu + Leu209His + Pro210Ser + Lys213Glu + Tyr214Pro + Tyr217Leu + Gly219Asn
Pro201Gln + Gly202Pro + Ile205Leu + Gln206Asp + Thr208Pro + Ala216Asn + Tyr217Leu + Gly219Glu + Thr220Glu
Pro201Gln + Gly202Gln + Ser204Gln + Glu + Gly211Pro + Asn212Ser + Lys213Asp + Tyr217Leu + Asn218Glu + Gly219Glu
Pro201Gln + Val203Asn + Ser204Asp + Gln206Asn + Leu209Ser + Asn212Glu + Tyr217Leu + Asn218Glu + Gly219Glu
Val203Cys + Ser204Asp + Leu209Val + Gly211Ser+ Lys213Asp + Ala216Asn + Tyr217Leu + Asn218Asp + Gly219Glu
Ala200Gly + Pro201Ser + Ser204Glu + Ile205Gln + Lys213Glu + Tyr217Leu + Asn218Asp + Gly219Glu + Thr220Ser

Pro201Asn + Gly202Ser + Val203Glu + Ile205Asn + Pro210Asp + Asn212Gln + Lys213Glu + Tyr214Glu + Tyr217Leu
Ile205Gly + Gln206Glu + Thr208Pro + Pro210Ser + Gly211Gln + Lys213Asp + Gly215Asp + Tyr217Leu + Gly219Asp
Val203Ala + Gln206Asp + Leu209Thr + Pro210Asp+ Asn212Gln + Tyr214Ala + Ala216Glu + Tyr217Leu + Gly219Asn
Ala200Ser + Pro201Ser + Gly202Asn + Ser204Asp + Gln206Asp + Leu209Cys + Ala216Gln + Tyr217Leu + Thr220Asp
Pro201Ser + Gly202Asn + Val203Ser + Ile205Ser + Asn212Asp + Tyr214Ala + Gly215Asp + Ala216Ser + Tyr217Glu
Val203Gln + Ile205Gln + Leu209His + Gly211Ser + Lys213Asp + Ala216Asp + Tyr217Leu + Asn218Glu + Gly219Pro
Pro201Gly + Ile205Thr + Gln206Glu + Thr208Gly + Leu209Ser + Gly211Asp + Gly215Glu + Tyr217Leu + Gly219Gln
Gly202Ser + Val203Gly + Ile205Ser + Gln206Glu + Thr208Ser + Pro210Ser + Gly211Asp + Gly215Glu + Tyr217Leu
Pro201Ser + Val203Asp + Ile205His + Pro210Gly + Gly211Pro + Lys213Glu + Gly215Glu + Tyr217Leu + Asn218Glu
Gly202Pro + Val203Thr + Ile205Ala + Gln206Glu + Thr208Ser + Pro210Glu + Asn212Gln + Lys213Glu + Tyr217Glu
Gly202Pro + Val203Asp + Gln206Asn + Leu209Gly + Lys213Glu + Gly215Asn + Ala216Glu + Tyr217Leu + Gly219Asp
Val203Cys + Ser204Asp + Gln206Glu + Thr208Ser + Asn212Asp + Tyr214Cys + Gly215Pro + Tyr217Leu + Asn218Asp
Pro201Gln + Gly202Pro + Ser204Glu + Gln206Asp + Leu209Cys + Asn212Asp + Tyr217Leu + Asn218Glu + Gly219Gln
Ala200Thr + Val203Glu + Ile205Pro + Thr208Ser + Pro210Ser + Asn212Glu + Tyr217Asp + Gly219Asp + Thr220Ser
Gly202Ser + Ser204Asp + Ile205Gln + Leu209Ile + Gly211Gln + Ala216Ser + Tyr217Leu + Gly219Ser + Thr220Asp
Ala200Ser + Gly202Gln + Val203Met + Ser204Glu + Leu209Pro + Pro210Ser + Gly215Ser + Tyr217His + Thr220Glu
Gly202Ser + Ser204Asp + Ile205Gly + Asn212Glu + Lys213Asp + Ala216Asp + Tyr217Ser + Asn218Ser + Gly219Pro
Val203Cys + Ser204Asp + Ile205Leu + Asn212Glu + Lys213Asp + Gly215Ser + Ala216Asp + Tyr217Leu + Thr220Gln
Pro201Gly + Gly202Pro + Ile205Asn + Thr208Gly + Asn212Asp + Lys213Asp + Gly215Asp + Tyr217Asn + Gly219Glu
Ala200Pro + Ser204Glu + Gln206Glu + Pro210Asn + Asn212Ser + Lys213Asp + Gly215Pro + Tyr217Leu + Thr220Pro
Gly202Asn + Val203Cys + Ser204Glu + Ile205Leu + Gln206Glu + Asn212Ser + Lys213Glu + Tyr217Leu + Gly219Glu
Ser204Glu + Gln206Glu + Thr208Asn + Lys213Glu + Tyr214Ser + Ala216Gln + Tyr217Leu + Asn218Gln + Gly219Asp
Pro201Asn + Ser204Glu + Ile205Met + Gln206Asp + Pro210Gly + Lys213Glu + Tyr214Met + Tyr217Leu + Gly219Glu
Ser204Glu + Thr208Asn + Pro210Gly + Gly211Glu + Asn212Gln + Lys213Asp + Ala216Glu + Tyr217Leu + Asn218Ser
Pro201Asn + Gln206Asn + Thr208Pro + Asn212Glu + Lys213Asp + Gly215Glu + Tyr217Leu + Asn218Ser + Thr220Glu
Pro201Asn + Gly202Asn + Ser204Asp + Ile205Met + Gln206Asn + Pro210Asn + Asn212Asp + Gly215Glu + Tyr217Leu
Ala200Ser + Pro201Gly + Gly202Ser + Ser204Asp + Thr208Ser + Leu209Ser + Asn212Glu + Gly215Asp + Tyr217Leu
Ser204Glu + Ile205Ala + Thr208Gly + Pro210Gly + Gly211Gln + Asn212Asp + Gly215Asp + Ala216His + Tyr217Leu
Ala200Pro + Pro201Asn + Gly202Asn + Asn212Glu + Tyr214Asp + Gly215Glu + Ala216Pro + Tyr217Leu + Thr220Glu
Ala200Ser + Gly202Asn + Val203Gln + Ser204Asp + Pro210Asp + Gly211Pro + Tyr214Pro + Ala216Glu + Tyr217Leu
Gly202Asn + Ile205Cys + Gln206Asn + Gly211Ser + Lys213Asp + Ala216Glu + Tyr217Leu + Asn218Glu + Thr220Asp
Pro201Ser + Val203Ala + Thr208Gln + Pro210Asp + Asn212Glu + Gly215Pro + Ala216Glu + Tyr217Leu + Gly219Pro
Gly202Gln + Ile205Cys + Gln206Asp + Leu209Ala + Asn212Ser + Lys213Asp + Ala216His + Tyr217Leu + Asn218Glu
Ala200Gln + Pro201Gly + Ile205Pro + Gln206Asp + Thr208Gln + Asn212Ser + Lys213Asp + Tyr217Asn + Asn218Asp
Pro201Asn + Thr208Ser + Pro210Gly + Gly211Asp + Lys213Glu + Gly215Asp + Tyr217Leu + Gly219Asp + Thr220Asn
Ser204Asp + Ile205Met + Gln206Asn + Leu209Ile + Asn212Ser + Gly215Glu + Tyr217Leu + Gly219Gln + Thr220Glu
Ala200His + Pro201Asn + Ser204Glu + Leu209His + Gly211Gln + Lys213Glu + Tyr217Leu + Asn218Glu + Thr220Asp
Ala200Thr + Pro201Gly + ILe205Pro + Pro210Glu + Gly211Asn + Gly215Asn + Tyr217Asp + Asn218Asp + Gly219Gln

TABLE 10-continued

Nonuple Mutation BPN' Variants

Ala200Pro + Ser204Glu + Ile205Gln + Thr208Gly + Lys213Asp + Tyr214Cys + Tyr217Leu + Gly219Asp + Thr220Asp

Pro201Gln + Val203Glu + Ser204Glu + Leu209Pro + Asn212Asp + Gly215Pro + Ala216Gly + Tyr217Leu + Thr220Glu

Gly202Ser + Ser204Asp + Pro210Asp + Asn212Asp + Tyr214Ser + Ala216Gly + Tyr217His + Asn218Gln + Thr220Gln

Ala200Asn + Pro201Ser + Leu209Ile + Pro210Asp + Gly211Asp + Asn212Ser + Gly215Gln + Tyr217Gln + Gly219Asp

Gly202Pro + Ile205Gln + Thr208Gln + Pro210Asn + Lys213Asp + Ala216Thr + Tyr217Leu + Asn218Asp + Gly219Asp

Ala200Pro + Ser204Asp + Thr208Gln + Asn212Asp + Lys213Glu + Tyr214Ser + Gly215Pro + Tyr217Leu + Thr220Gly

Ala200Asn + Val203Glu + Ser204Asp + Ile205Ala + Gln206Ser + Leu209Gln + Pro210Gln + Lys213Glu + Tyr217Met

Pro201Gln + Val203Glu + Ser204Glu + Ile205Val + Asn212Asp + Tyr214Gln + Gly215Ser + Ala216Gly + Tyr217Leu

Ala200Ser + Val203Asp + Ser204Glu + Thr208Asn + Gly211Pro + Asn212Gln + Lys213Asp + Tyr214Gly + Tyr217Leu

Pro201Gln + Val203Ala + Ile205His + Leu209Met + Gly211Glu + Asn212Glu + Tyr217Leu + Gly219Glu + Thr220Gly

Ala200Gly + Val203Cys + Ser204Asp + Leu209Val + Pro210Gln + Gly211Glu + Asn212Asp + Gly215Pro + Tyr217Gln

Ala200Gln + Leu209Ser + Pro210Ser + Gly211Glu + Asn212Asp + Ala216Gly + Tyr217Leu + Asn218Asp + Gly219Ser

Val203Ser + Ser204Glu + Ile205Ala + Thr208Pro + Pro210Asn + Lys213Glu + Tyr214Asp + Tyr217Leu + Gly219Asp

TABLE 11

Decuple Mutation BPN' Variants

Ala200His + Val203Asn + Gln206Ser + Leu209Ala + Pro210Ser + Lys213Glu + Tyr214Cys + Ala216Ser + Tyr217Leu + Asn218Gln

Ala200Thr + Val203Asn + Gln206Asp + Thr208Asn + Leu209Gln + Tyr214Val + Ala216Gly + Tyr217Leu + Gly219Pro + Thr220Gly

Ala200Thr + Pro201Gly + Gly202Gln + Ile205His + Leu209Ser + Asn212Glu + Tyr214Gln + Ala216Thr + Tyr217Leu + Thr220Asn

Ala200Thr + Gly202Ser + Val203Pro + Ile205Met + Leu209Gln + Gly211Pro + Lys213Asp + Tyr217Leu + Asn218Ser + Thr220Gln

Ala200Thr + Pro201Gln + Ile205Ala + Thr208Pro + Leu209Met + Lys213Asp + Tyr214Pro + Tyr217Leu + Asn218Gln + Gly219Asn

Ala200Gln + Pro201Asn + Gly202Gln + Ile205Gly + Thr208Asn + Leu209Gln + Pro210Gly + Gly215Glu + Ala216Ser + Tyr217Leu

Ala200His + Pro201Ser + Val203Cys + Thr208Pro + Leu209Ile + Pro210Asn + Gly215Asn + Ala216Glu + Tyr217Leu + Asn218Ser

Ala200Pro + Pro201Ser + Val203Asn + Ser204Glu + Ile205His + Leu209Val + Pro210Gly + Gly211Ser + Ala216Gln + Tyr217Leu

Ala200His + Pro201Gln + Ile205Ser + Gln206Asn + Thr208Ser + Pro210Glu + Gly215Pro + Ala216Thr + Tyr217Leu + Gly219Asn

Ala200Pro + Pro201Gln + Gly202Asn + Val203Pro + Ile205Val + Leu209Met + Gly211Gln + Asn212Gln + Tyr217Leu + Asn218Ser

Ala200Gly + Gly202Ser + Ile205Gln + Leu209Thr + Gly211Asn + Asn212Ser + Tyr217Leu + Asn218Asp + Gly219Pro + Thr220Ser

Ala200Thr + Pro201Ser + Gly202Pro + Val203Met + Ile205Met + Asn212Ser + Tyr214Ser + Tyr217Leu + Asn218Asp + Gly219Glu

Ala200His + Gly202Ser + Thr208Gly + Leu209Ser + Gly211Asn + Asn212Asp + Lys213Asp + Ala216Ser + Tyr217Leu + Thr220Ser

Ala200Asn + Val203His + Thr208Pro + Leu209Ile + Gly211Asn + Asn212Asp + Lys213Asp + Tyr214Asn + Ala216Gly + Tyr217Thr

TABLE 11-continued

Decuple Mutation BPN' Variants

Ala200Pro + Gly202Gln + Val203Glu + Ser204Asp + Thr208Asn + Leu209Met + Asn212Gln + Gly215Asn + Ala216Asn + Tyr217Leu

Pro201Gly + Gly202Asn + Gln206Asn + Gly211Pro + Asn212Gln + Lys213Asp + Tyr214Glu + Ala216Pro + Tyr217Leu + Gly219Gln

Pro201Gly + Leu209Pro + Pro210Asn + Asn212Ser + Lys213Asp + Tyr214Asp + Gly215Pro + Ala216Gly + Tyr217Ser + Thr220Ser

Ala200Gly + Val203Asp + Ile205Gly + Thr208Ser + Pro210Gln + Gly215Asn + Tyr217Leu + Asn218Asp + Gly219Asp + Thr220Gln

Gly202Asn + Ser204Glu + Ile205Met + Gln206Ser + Leu209Ser + Tyr214Cys + Gly215Ser + Ala216Thr + Tyr217Pro + Asn218Glu

Ala200Thr + Gly202Gln + Ile205Val + Pro210Asp + Gly211Glu + Lys213Glu + Tyr214Gln + Gly215Ser + Tyr217Leu + Thr220Pro

Ala200Asn + Pro201Gln + Gly202Pro + Leu209Ile + Pro210Gly + Asn212Glu + Lys213Asp + Tyr214Asp + Gly215Pro + Tyr217Leu

Ala200His + Val203Asn + Gln206Asn + Gly211Pro + Asn212Gln + Tyr214Asn + Tyr217Leu + Asn218Glu + Gly219Asp + Thr220Asp

Pro201Asn + Gly202Pro + Val203Glu + Ser204Glu + Gln206Asn + Gly211Asn + Tyr214Thr + Tyr217Glu + Asn218Ser + Gly219Gln

Gly202Ser + Val203Pro + Ile205Ala + Gln206Ser + Thr208Ser + Leu209Gln + Gly211Glu + Lys213Glu + Gly215Ser + Tyr217Leu

Ala200Gly + Gly202Ser + Val203Asn + Ile205Val + Gln206Ser + Gly211Asp + Lys213Asp + Tyr214Thr + Ala216Pro + Tyr217Leu

Ile205Met + Gln206Ser + Leu209Gly + Pro210Gln + Gly211Asp + Asn212Gln + Lys213Asp + Tyr214Asn + Tyr217Leu + Gly219Asn

Pro201Ser + Val203Asp + Ser204Asp + Leu209Thr + Pro210Ser + Asn212Gln + Ala216Gln + Tyr217Val + Asn218Asp + Gly219Glu

Ala200Pro + Gly202Ser + Val203His + Ser204Asp + Ile205Ala + Gly211Pro + Ala216Glu + Tyr217Leu + Asn218Asp + Gly219Gln

Val203Met + Ser204Asp + Ile205Pro + Gln206Ser + Leu209Ser + Pro210Asn + Asn212Ser + Ala216Asp + Tyr217Leu + Asn218Glu

Pro201Gly + Gly202Ser + Val203Gly + Gln206Asn + Thr208Pro + Pro210Asp + Gly211Pro + Lys213Glu + Tyr214Met + Tyr217Ala

Ala200His + Pro201Asn + Thr208Gly + Leu209Ala + Pro210Asp + Gly211Ser + Lys213Asp + Ala216Gly + Tyr217Leu + Thr220Asn

Ala200Asn + Pro201Asn + Gly202Pro + Thr208Ser + Pro210Asp + Asn212Glu + Lys213Glu + Tyr214Glu + Tyr217Leu + Thr220Asn

Ala200Gly + Val203His + Ser204Glu + Ile205Thr + Gln206Ser + Leu209Asn + Gly211Asn + Tyr217Leu + Asn218Glu + Gly219Asp

Ser204Glu + Thr208Gln + Leu209Val + Pro210Asn + Tyr214Met + Gly215Glu + Ala216Glu + Tyr217Leu + Gly219Gln + Thr220Gln

Ala200Gly + Pro201Asn + Val203Asn + Ser204Asp + Gln206Glu + Leu209Ile + Pro210Ser + Gly215Asn + Tyr217Leu + Thr220Gly

Pro201Ser + Val203Asn + Ser294Glu + Ile205Met + Gln206Glu + Thr208Pro + Leu209Ala + Tyr214Leu + Tyr217Ser + Gly219Ser

Ala200Asn + Ser204Glu + Gln206Glu + Leu209Ser + Gly211Pro + Ala216Glu + Tyr217Leu + Asn218Glu + Gly219Ser + Thr220Ser

Val203Glu + Ile205His + Leu209Gln + Pro210Asn + Gly211Asn + Asn212Gln + Tyr214His + Gly215Pro + Tyr217Leu + Gly219Glu

Pro201Gly + Gly202Ser + Ser204Asp + Gln206Asp + Leu209Val + Tyr214Ser + Gly215Glu + Ala216Asn + Tyr217Asp + Gly219Ser

TABLE 11-continued

Decuple Mutation BPN' Variants

Val203Glu + Thr208Asn + Leu209Val + Gly211Gln + Tyr214Cys + Gly215Asn + Tyr217Asp + Asn218Ser + Gly219Asp + Thr220Gly

Val203Asp + Ser204Asp + Gln206Asp + Thr208Asn + Leu209Met + Pro210Ser + Gly211Gln + Ala216Ser + Tyr217Leu + Thr220Pro

Ala200Gly + Val203Gln + Ser204Glu + Gln206Glu + Thr208Gln + Leu209Met + Tyr214Ser + Gly215Glu + Tyr217Leu + Gly219Ser

Gly202Asn + Ser204Asp + Gln206Asp + Thr208Gly + Leu209Pro + Pro210Asn + Gly215Asp + Ala216Pro + Tyr217Leu + Gly219Gln

Ile205Thr + Gln206Ser + Pro210Gly + Asn212Gln + Lys213Asp + Gly215Asp + Tyr217Thr + Asn218Gln + Gly219Ser + Thr220Pro

Pro201Ser + Gly202Gln + Val203Gln + Thr208Asn + Asn212Gln + Lys213Glu + Tyr214Ser + Gly215Glu + Tyr217Pro + Gly219Asn

Pro201Gln + Gly202Gln + Ser204Asp + Ile205His + Gln206Glu + Thr208Asn + Tyr214His + Ala216Thr + Tyr217Leu + Asn218Glu

Ala200His + Gly202Pro + Ser204Glu + Ile205Val + Gln206Glu + Gly211Pro + Ala216Gln + Tyr217Leu + Asn218Glu + Thr220Pro

Ala200His + Val203Ala + Ser204Glu + Ile205Met + Gln206Glu + Thr208Gln + Pro210Ser + Tyr214Ile + Tyr217Leu + Asn218Glu

Gly202Pro + Ile205His + Gln206Ser + Leu209Asn + Gly211Ser + Asn212Asp + Tyr214Asp + Tyr217Leu + Gly219Asn + Thr220Gly

Ala200Gly + Ile205Cys + Gly211Gln + Asn212Ser + Gly215Gln + Ala216His + Tyr217Leu + Asn218Asp + Gly219Gln + Thr220Asp

Pro201Gly + Gly202Asn + Ile205Gly + Gln206Asn + Leu209Cys + Pro210Glu + Gly211Glu + Tyr214Asp + Ala216Gln + Tyr217Leu

Pro201Gly + Val203Asp + Ser204Asp + Ile205Cys + Leu209Ile + Asn212Ser + Ala216Pro + Tyr217Leu +Gly219Glu + Thr220Glu

Gly202Ser + Ile205Ala + Thr208Asn + Leu209Met + Lys213Glu + Tyr214Met + Gly215Glu + Ala216Glu + Tyr217Leu + Thr220Gly

Ala200Asn + Pro201Ser + Gln206Asn + Pro210Gly + Lys213Glu + Tyr214Glu + Gly215Gln + Ala216Glu + Tyr217Leu + Gly219Gln

Pro201Gly + Gly202Gln + Val203His + Thr208Ser + Pro210Glu + Lys213Asp + Gly215Glu + Ala216His + Tyr217Ala + Asn218Gln

Pro201Ser + Gln206Asp + Leu209Ala + Pro210Asn + Gly211Pro + Lys213Glu + Tyr214Ala + Gly215Asp + Tyr217Cys + Asn218Ser

Gly202Gln + Ile205Met + Gln206Asn + Leu209His + Pro210Glu + Gly211Asp + Asn212Ser + Tyr214Asp + Gly215Asp + Tyr217Leu

Ala200His + Gly202Gln + Ser204Glu + Gly211Ser + Tyr214Val + Gly215Glu + Ala216Gln + Tyr217Leu + Asn218Asp + Thr220Asn

Gly202Ser + Ser204Asp + Ile205Cys + Thr208Ser + Pro210Gly + Gly211Ser + Asn212Ser + Tyr214Leu + Tyr217Leu + Gly219Asp

Ala200Pro + Ser204Glu + Gln206Asn + Leu209His + Pro210Gln + Asn212Ser + Tyr214Met + Tyr217Leu + Gly219Glu + Thr220Asn

Pro201Gln + Ser204Asp + Ile205Asn + Gln206Asn + Thr208Asn + Pro210Asn + Ala216Glu + Tyr217Ser + Asn218Asp + Thr220Asp

Ala200Gln + Gly202Gln + Val203Ser + Gln206Glu + Leu209Thr + Gly211Glu + Lys213Glu + Tyr214Asp + Ala216Gln + Tyr217Met

Pro201Gly + Gly202Asn + Ile205Gln + Pro210Asp + Asn212Glu + Tyr214Val + Gly215Asp + Ala216Thr + Tyr217Leu + Asn218Ser

Pro201Ser + Gly202Gln + Ile205Pro + Gln206Ser + Leu209Asn + Gly211Asp + Asn212Gln + Tyr214Glu + Tyr217Leu + Asn218Gln

Gly202Ser + Val203Ser + Gln206Asp + Leu209Ile + Pro210Gly + Gly211Asp + Tyr214Asp + Gly215Asp + Ala216Thr + Tyr217Ala

Ala200Gln + Pro201Ser + Val203Met + Gln206Glu + Thr208Pro + Leu209Gly + Pro210Gly + Ala216Gly + Tyr217Leu + Asn218Asp

Ala200Thr + Pro201Gly + Ser204Glu + Gln206Asp + Leu209Cys + Gly215Asn + Ala216Gly + Tyr217Gly + Asn218Glu + Thr220Asp

Ala200Thr + Gly202Asn + Ile205Gln + Gln206Ser + Asn212Gln + Lys213Glu + Gly215Asp +Ala216Asp + Tyr217Leu + Asn218Glu

Ala200Asn + Ser204Asp + Ile205Leu + Gln206Glu + Pro210Asn + Asn212Ser + Gly215Asp + Tyr217Leu + Gly219Glu + Thr220Gln

Ala200Thr + Val203His + Ile205Met + Gln206Asp + Thr208Pro + Leu209Thr + Asn212Glu + Gly215Asp + Ala216Asp + Tyr217Leu

Ala200Thr + Val203Ser + Ser204Asp + Ile205Gly + Gln206Asp + Thr208Pro + Leu209His + Lys213Asp + Tyr214Asp + Tyr217Leu

Gly202Pro + Gln206Asp + Pro210Ser + Gly211Glu + Asn212Asp + Lys213Asp + Tyr214Ala + Gly215Asn + Tyr217Leu + Thr220Gly

Gln206Glu + Thr208Ser + Leu209Asn + Tyr214Gln + Gly215Asn + Ala216Glu + Tyr217Leu + Asn218Asp + Gly219Gln + Thr220Glu

Ala200Pro + Pro201Asn + Gly202Pro + Gln206Asp + Thr208Ser + Gly211Glu + Asn212Asp + Tyr214Asp + Tyr217Leu + Gly219Pro

Pro201Gly + Ile205His + Gln206Asn + Lys213Glu + Tyr214Glu + Gly215Asp + Ala216Gly + Tyr217Leu + Asn218Asp + Gly219Ser

Ala200Asn + Gly202Pro + Val203Ser + Gln206Asp + Leu209Gln + Pro210Glu + Gly215Asp + Tyr217Glu + Gly219Asn + Thr220Gly

Pro201Gln + Ser204Glu + Leu209Gln + Lys213Asp + Tyr214Pro + Gly215Pro + Ala216Glu + Tyr217Leu + Asn218Glu + Thr220Gln

Val203Asn + Ser204Asp + Ile205Val + Thr208Pro + Pro210Gln + Lys213Asp + Tyr214Ser + Ala216Glu + Tyr217Leu + Asn218Glu

Gly202Asn + Val203Ala + Ser204Glu + Gln206Glu + Leu209Gly + Pro210Asp + Gly215Glu + Tyr217His + Gly219Ser + Thr220Pro

Pro201Gly + Gly202Ser + Ile205His + Gln206Asp + Thr208Ser + Pro210Gln + Asn212Asp + Lys213Asp + Tyr217Leu + Thr220Gln

Ala200Gly + Pro201Gly + Gly202Pro + Gln206Asp + Thr208Gly + Pro210Gln + Asn212Glu + Lys213Glu + Tyr217Val + Thr220Gln

Ala200His + Gln206Asp + Thr208Pro + Pro210Gln + Asn212Asp + Lys213Glu + Tyr214Leu + Gly215Gln + Ala216Gln + Tyr217Leu

Pro201Gly + Val203Pro + Ser204Asp + Ile205Leu + Gln206Asp + Pro210Glu + Asn212Ser + Gly215Gln + Ala216Glu + Tyr217Leu

Ala200Gly + Val203Asp + Ser204Asp + Thr208Asn + Leu209Ile + Gly211Asn + Lys213Glu + Tyr214Thr + Ala216Glu + Tyr217Leu

Pro201Asn + Gly202Pro + Thr208Gln + Leu209Ala + Pro210Glu + Gly211Glu + Asn212Asp + Gly215Gln + Ala216Glu + Tyr217Ala

Ala200Thr + Pro201Gly + Gly202Asn + Val203Thr + Gln206Glu + Leu209Cys + Pro210Asp + Gly211Asn + Lys213Glu + Tyr217Leu

Ala200His + Gly202Ser + Ser204Glu + Leu209Pro + Lys213Glu + Tyr214Ser + Gly215Asp + Ala216Thr + Tyr217Leu + Asn218Ser

Pro201Gly + Gly202Pro + Ser204Glu + Pro210Gly + Asn212Glu + Lys213Glu + Tyr214Thr + Gly215Asp + Tyr217Leu + Asn218Ser

Ala200Gly + Val203Ser + Gln206Asn + Leu209Ser + Gly211Pro + Asn212Glu + Lys213Glu + Gly215Gln + Ala216Glu + Tyr217Asn

TABLE 11-continued

Decuple Mutation BPN' Variants

Ala200Asn + Pro201Asn + Val203Cys + Ser204Asp + Ile205Met + Leu209Pro + Gly211Asp + Asn212Asp + Lys213Glu + Tyr217Leu
Gly202Ser + Val203Pro + Ser204Glu + Thr208Pro + Leu209His + Pro210Glu + Gly211Asp + Asn212Glu + Tyr217Leu + Asn218Gln
Pro201Ser + Ser204Asp + Thr208Pro + Leu209Met + Pro210Asp + Gly211Glu + Asn212Asp + Tyr214Gly + Tyr217Gly + Thr220Pro
Gly202Ser + Val203Gln + Ile205Asn + Gln206Asn + Pro210Glu + Gly211Asp + Asn212Glu + Ala216Asn + Tyr247Gly + Gly219Glu
Ala200Ser + Val203His + Ser204Asp + Pro210Glu + Lys213Asp + Tyr214Ala + Gly215Asp + Ala216His + Tyr217Leu + Thr220Pro
Gly202Pro + Ser204Glu + Ile205Pro + Thr208Asn + Pro210Glu + Asn212Ser + Lys213Glu + Gly215Asp + Ala216Gln + Tyr217Leu
Ser204Glu + Ile205Met + Thr208Asn + Pro210Gln + Lys213Asp + Tyr214Ala + Gly215Glu + Ala216Gln + Tyr217Leu + Asn218Glu
Gly202Gln + Ser204Glu + Ile205Ala + Asn212Ser + Lys213Asp + Tyr214Thr + Gly215Asp + Ala216Gln + Tyr217Leu + Asn218Asp
Pro201Gly + Val203Cys + Ser204Asp + Leu209Ala + Lys213Asp + Gly215Asp + Tyr217Leu + Asn218Asp + Gly219Ser + Thr220Gly
Ser204Glu + Gln206Glu + Thr208Asn + Leu209Met + Asn212Ser + Lys213Glu + Tyr214His + Tyr217Leu + Asn218Asp + Gly219Pro
Gly202Ser + Gln206Asp + Thr208Ser + Gly211Pro + Tyr214Met + Gly215Ser + Tyr217Leu + Asn218Glu + Gly219Gln + Thr220Glu
Ala200Thr + Gly202Gln + Ser204Glu + Ile205His + Leu209Met + Gly211Asp + Asn212Ser + Tyr217Glu + Asn218Asp + Gly219Gln
Val203Pro + Ser204Glu + Gln206Asn + Leu209Gly + Gly211Asp + Lys213Glu + Tyr214Asp + Gly215Gln + Tyr217Cys + Thr220Asn
Ala200Gln + Pro201Gly + Ser204Glu + Ile205Val + Pro210Asn + Asn212Ser + Gly215Glu + Tyr217Leu + Gly219Glu + Thr220Asp
Pro201Gln + Ile205Ala + Gln206Glu + Thr208Pro + Leu209Ile + Pro210Gly + Lys213Glu + Ala216Gln + Tyr217Leu + Gly219Asn
Pro201Gln + Ile205His + Gln206Asp + Thr208Asn + Leu209Ile + Pro210Gly + Asn212Gln + Lys213Glu + Tyr217Leu + Thr220Ser
Ala200Gln + Val203His + Ile205Gln + Gln206Asp + Thr208Asn + Gly211Pro + Lys213Glu + Ala216Pro + Tyr217Leu + Thr220Gln
Ala200Ser + Val203Thr + Ile205Ala + Gln206Glu + Leu209Asn + Gly211Pro + Lys213Glu + Ala216Thr + Tyr217Leu + Gly219Asn
Ala200Gly + Gly202Ser + Ser204Asp + Gln206Asn + Thr208Pro + Leu209Ala + Lys213Glu + Ala216Glu + Tyr217Leu + Thr220Gln
Gly202Ser + Val203Gly + Ser204Asp + Leu209Gln + Gly211Asn + Lys213Glu + Tyr214Gln + Ala216Glu + Tyr217Leu + Gly219Ser
Ala200Thr + Pro201Gln + Gly202Asn + Ile205Leu + Asn212Asp + Tyr214Ser + Gly215Glu + Tyr217Leu + Gly219Pro + Thr220Pro
Ala200Gly + Gly202Ser + Val203Ser + Leu209Thr + Gly211Ser + Asn212Glu + Tyr214Asn + Gly215Glu + Ala216His + Tyr217Leu
Pro201Asn + Val203Thr + Gln206Asn + Pro210Ser + Asn212Asp + Gly215Asp + Ala216Gly + Tyr217Leu + Gly219Asn + Thr220Pro
Ala200Gly + Pro201Asn + Pro210Glu + Gly211Glu + Asn212Gln + Lys213Glu + Tyr217Met + Asn218Ser + Gly219Ser + Thr220Asp
Ala200Gly + Gln206Glu + Pro210Gln + Gly211Glu + Lys213Asp + Tyr214Cys + Gly215Ser + Ala216Ser + Tyr217Leu + Thr220Pro
Pro201Ser + Gly202Ser + Val203Glu + Ser204Glu + Pro210Gln + Lys213Glu + Tyr214Val + Gly215Glu + Tyr217Ala + Asn218Gln
Pro201Ser + Gly202Asn + Ile205Thr + Gln206Ser + Asn212Asp + Lys213Glu + Tyr214Asn + Gly215Asp + Tyr217Leu + Asn218Asp
Gly202Ser + Ile205Ala + Thr208Gln + Leu209Ala + Gly211Glu + Lys213Glu + Tyr214Gln + Ala216Asp + Tyr217Leu + Gly219Gln
Ala200Pro + Pro201Gln + Val203Cys + Gln206Ser + Leu209Ser + Gly215Asp + Ala216Glu + Tyr217Leu + Gly219Glu + Thr220Asp
Ala200Pro + Gly202Gln + Ser204Glu + Ile205Thr + Gln206Glu + Thr208Pro + Leu209Pro + Asn212Asp + Tyr217Asp + Asn218Gln
Gly202Ser + Ser204Asp + Ile205Pro + Leu209Asn + Pro210Ser + Asn212Asp + Gly215Pro + Ala216Glu + Tyr217Leu + Asn218Glu
Gly202Pro + Ser204Glu + Ile205Val + Thr208Asn + Gly211Asn + Asn212Asp + Tyr214Val + Ala216Glu + Tyr217Leu + Asn218Asp
Pro201Gln + Gly202Ser + Ser204Glu + Gln206Glu + Thr208Gly + Leu209Thr + Lys213Asp + Ala216His + Tyr217Leu + Thr220Ser
Ser204Glu + Ile205Val + Gln206Glu + Leu209His + Pro210Ser + Lys213Glu + Tyr214Pro + Ala216Pro + Tyr217Leu + Gly219Asn
Ala200Gly + Gly202Gln + Ser204Glu + Ile205Cys + Gln206Glu + Leu209Ala + Lys213Glu + Tyr217Leu + Gly219Gln + Thr220Asn
Pro201Ser + Gly202Ser + Ser204Asp + Gln206Asp + Thr208Pro + Pro210Asn + Lys213Glu + Gly215Asn + Tyr217Leu + Thr220Gly
Ala200His + Gly202Asn + Val203Glu + Ile205Thr + Gln206Glu + Thr208Asn + Lys213Asp + Tyr214Gly + Tyr217Leu + Asn218Glu
Ala200Ser + Gly202Ser + Ser204Asp + Gln206Asp + Thr208Ser + Gly211Gln + Tyr214Asp + Ala216Pro + Tyr217Leu + Gly219Gln
Ser204Asp + Ile205Cys + Leu209Asn + Gly211Gln + Asn212Gln + Lys213Glu + Gly215Pro + Tyr217Leu + Asn218Asp + Gly219Glu
Pro201Ser + Ile205Gln + Gln206Glu + Pro210Asn + Gly211Ser + Asn212Gln + Lys213Asp + Gly215Asp + Tyr217Leu + Gly219Glu
Pro201Asn + Ile205His + Leu209Ser + Gly211Asp + Lys213Asp + Tyr214Glu + Gly215Gln + Ala216Thr + Tyr217Leu + Asn218Gln
Ala200Gln + Ile205Gln + Thr208Gln + Leu209Ser + Pro210Asn + Asn212Gln + Lys213Glu + Ala216Glu + Tyr217Leu + Asn218Asp
Gly202Ser + Val203Gly + Ile205Ser + Gln206Glu + Thr208Ser + Pro210Ser + Gly211Asp + Gly215Glu + Tyr217Leu + Gly219Ser
Val203Gly + Ser204Glu + Ile205His + Leu209Ile + Pro210Asn + Asn212Asp + Gly215Glu + Tyr217Leu + Asn218Glu + Thr220Gln
Pro201Gly + Gly202Gln + Val203Glu + Gln206Glu + Pro210Asn + Asn212Ser + Gly215Asp + Ala216Gln + Tyr217Leu + Thr220Asp
Ala200Thr + Ser204Glu + Thr208Asn + Leu209Asn + Pro210Glu + Gly211Asp + Tyr214Ser + Gly215Glu + Tyr217Gly + Gly219Gln
Pro201Gly + Val203Glu + Ile205Val + Gln206Asn + Thr208Ser + Pro210Asn + Asn212Asp +Tyr217Leu + Gly219Glu + Thr220Asp
Pro201Asn + Gly202Pro + Val203Asp + Ile205Met + Gly211Asn + Lys213Asp + Ala216Asp + Tyr217Leu + Gly219Asp + Thr220Gln
Pro201Gly + Val203Asp + Ile205Cys + Thr208Asn + Leu209Ser + Pro210Asp + Lys213Glu + Gly215Asp + Ala216Gly + Tyr217Leu
Gly202Gln + Ile205Gln + Gln206Asp + Leu209Thr + Asn212Glu + Gly215Gln + Ala216Glu + Tyr217Leu + Asn218Glu + Gly219Asn

TABLE 11-continued

Decuple Mutation BPN' Variants

Ala200His + Gly202Gln + Ser204Glu + Gln206Asp + Leu209Val + Asn212Glu + Tyr214His + Tyr217Leu + Asn218Asp + Thr220Pro

Ala200Ser + Val203Asp + Thr208Gly + Leu209Asn + Gly211Glu + Tyr214Thr + Ala216Asp + Tyr217Leu + Asn218Asp + Gly219Pro

Gly202Asn + Val203Asp + Ile205Pro + Leu209Gly + Lys213Asp + Tyr214Gln + Tyr217Met + Asn218Asp + Gly219Asn + Thr220Glu

Pro201Asn + Gly202Gln + Ser204Asp + Gln206Glu + Thr208Gln + Leu209Cys + Tyr214Asp + Ala216His + Tyr217Leu + Thr220Glu

Ala200Ser + Pro201Gly + Ser204Glu + Gln206Asp + Thr208Ser + Leu209Ile + Gly211Glu + Asn212Ser + Tyr217Leu + Asn218Glu

Pro201Gly + Val203Glu + Gln206Asp + Pro210Gly + Gly211Asn + Asn212Asp + Ala216Glu + Tyr217Leu + Gly219Gln + Thr220Ser

Val203Gly + Gln206Asn + Leu209Pro + Gly211Asn + Asn212Glu + Lys213Asp + Gly215Glu + Tyr217Leu + Gly219Glu + Thr220Ser

Pro201Gln + Gly202Gln + Ile205Gln + Thr208Gln + Pro210Gly + Asn212Glu + Ala216Asp + Tyr217Glu + Asn218Ser + Gly219Asp

Ala200Gly + Gly202Asn + Val203Glu + Leu209Asn + Pro210Ser + Gly211Asn + Asn212Ser + Lys213Asp + Ala216Glu + Tyr217Leu

Pro201Gly + Ser204Asp + Ile205Gln + Leu209Cys + Gly211Asp + Lys213Asp + Tyr214Gln + Ala216Glu + Tyr217Leu + Thr220Ser

Pro201Gln + Gly202Pro + Val203Cys + Ile205Thr + Leu209Asn + Pro210Gln + Gly215Glu + Ala216Glu + Tyr217Leu + Thr220Asp

Gly202Asn + Val203Thr + Ser204Glu + Thr208Ser + Leu209Thr + Lys213Glu + Gly215Glu + Ala216Pro + Tyr217Leu + Gly219Asp

Gly202Asn + Val203Gln + Ser204Glu + Gln206Glu + Thr208Ser + Gly211Glu + Lys213Asp + Ala216Thr + Tyr217Leu + Thr220Ser

Ala200Pro + Pro201Asn + Ser204Asp + Ile205Met + Gln206Asp + Thr208Asn + Pro210Ser + Gly211Glu + Lys213Glu + Tyr217Leu

Gly202Gln + Ile205Gly + Thr208Asn + Gly211Glu + Lys213Asp + Tyr214Gln + Ala216Glu + Tyr217Leu + Asn218Asp + Thr220Asn

Pro201Ser + Val203Asp + Gln206Ser + Asn212Gln + Lys213Glu + Gly215Glu + Ala216Gly + Tyr217Leu + Gly219Asn + Thr220Gly

Gly202Ser + Val203Glu + Gln206Glu + Thr208Ser + Leu209Gln + Gly211Pro + Lys213Glu + Tyr214Gln + Tyr217Asn + Gly219Asn

Ala200Gln + Pro201Gly + Ile205Pro + Gln206Asp + Lys213Glu + Gly215Pro + Tyr217Leu + Asn218Asp + Gly219Gln + Thr220Gln

Pro201Gln + Gly202Ser + Val203His + Gln206Asp + Gly211Glu + Asn212Glu + Tyr217Leu + Asn218Gln + Gly219Ser + Thr220Asn

Ala200Pro + Ser204Asp + Thr208Gln + Leu209Ile + Gly211Pro + Asn212Glu + Ala216Asp + Tyr217Leu + Gly219Asp + Thr220Gly

Val203Asn + Ser204Glu + Thr208Asn + Pro210Asp + Gly211Ser + Tyr214Asn + Ala216Pro + Tyr217Asn + Asn218Glu + Thr220Glu

Ala200Asn + Ser204Glu + Thr208Gly + Pro210Gly + Gly211Asp + Tyr214Val + Ala216Glu + Tyr217Leu + Gly219Asp + Thr220Ser

Pro201Asn + Gly202Asn + Ile205Cys + Gln206Glu + Thr208Gly + Pro210Asp + Gly211Asn + Lys213Asp + Tyr217Leu + Asn218Glu

Ala200Gly + Val203Met + Ser204Asp + Thr208Gln + Leu209His + Pro210Glu + Gly215Gln + Tyr217Leu + Gly219Asp + Thr220Asp

Pro201Ser + Ile205Cys + Thr208Gly + Lys213Glu + Gly215Glu + Ala216Gly + Tyr217Leu + Asn218Asp + Gly219Asn + Thr220Glu

Ala200Gln + Pro201Gln + Gly202Asn + Val203Met + Gln206Glu + Gly211Asp + Asn212Asp + Ala216Glu + Tyr217Leu + Asn218Ser

Ala200Gly + Pro201Gln + Gly202Gln + Ser204Glu + Leu209Met + Pro210Asp + Tyr214Asp + Gly215Pro + Ala216Gln + Tyr217Leu

Ala200Thr + Pro201Gln + Gly202Asn + Gln206Ser + Asn212Glu + Gly215Glu + Tyr217Leu + Asn218Asp + Gly219Glu + Thr220Gly

Ala200Pro + Pro201Asn + Val203Asp + Leu209Gln + Pro210Gly + Lys213Asp + Tyr214His + Gly215Asp + Tyr217Leu + Gly219Glu

Ala200Thr + Gly202Gln + Val203Asp + Gln206Ser + Leu209Ala + Lys213Asp + Gly215Glu + Tyr217Leu + Asn218Ser + Gly219Asp

Gly202Asn + Val203Glu + Ile205His + Leu209Gly + Lys213Glu + Gly215Pro + Tyr217Leu + Asn218Gln + Gly219Asp + Thr220Gln

Gly202Ser + Val203Gly + Ser204Glu + Gln206Ser + Thr208Ser + Gly211Asn + Lys213Asp + Gly215Gln + Tyr217Glu + Thr220Glu

Ala200Ser + Gly202Gln + Val203Glu + Ser204Asp + Pro210Asp + Tyr214Asp + Ala216Gln + Tyr217Leu + Gly219Ser + Thr220Asn

Pro201Ser + Gly202Asn + Val203Pro + Ile205Val + Thr208Pro + Pro210Asp + Ala216Asp + Tyr217Leu + Asn218Asp + Thr220Gln

Ala200Asn + Pro201Gly + Thr208Gln + Leu209Thr + Pro210Glu + Asn212Ser + Ala216Glu + Tyr217Leu + Asn218Glu + Thr220Pro

Val203Asp + Gln206Asn + Thr208Pro + Leu209Met + Asn212Ser + Lys213Glu + Tyr214Glu + Gly215Pro + Tyr217Leu + Asn218Glu

Ala200Gly + Gly202Ser + Leu209Ala + Gly211Asn + Asn212Gln + Lys213Asp + Tyr217Asn + Asn218Glu + Gly219Glu + Thr220Ser

Ala200Gln + Thr208Gly + Leu209Val + Pro210Gly + Asn212Asp + Ala216Asn + Tyr217Val + Asn218Glu + Gly219Glu + Thr220Gly

Gly202Pro + Ile205Val + Thr208Pro + Leu209Gly + Pro210Ser + Asn212Glu + Gly215Pro +Tyr217Leu + Gly219Asp + Thr220Glu

Gly202Ser + Val203Cys + Leu209Thr + Pro210Ser + Asn212Glu + Tyr214Ile + Ala216Pro + Tyr217Leu + Gly219Asp + Thr220Asp

Ala200Ser + Gly202Ser + Ile205Asn + Thr208Pro + Asn212Glu + Lys213Asp + Ala216Pro + Tyr217Leu + Asn218Asp + Gly219Asp

TABLE 12

Preferred BPN' Variants

Single Mutation

Lys213Glu
Ala216Glu
Ala216Asp
Ala216Gly
Ser204Glu
Val203Glu

Double Mutation

Lys213Glu + Tyr217Leu
Ile205Leu + Ala216Glu
Ile205Leu + Ala216Asp
Pro210Ala + Gly215Thr
Lys213Glu + Ala216Glu
Tyr214Phe + Tyr217Asn
Gln206Glu + Ala216Glu
Ala216Glu + Tyr217Leu
Gln206Glu + Tyr217Leu
Gln206Glu + Lys213Glu

TABLE 12-continued

Preferred BPN' Variants

Triple Mutation

Gln206Pro + Gly211Ala + Ala216Glu
Lys213Glu + Ala216Glu + Tyr217Leu
Ile205Val + Pro210Ala + Lys213Glu
Gln206Glu + Ala216Glu + Tyr217Leu
Gln206Glu + Lys213Glu + Tyr217Leu

Quadruple Mutation

Pro210Ala + Lys213Glu + Ala216Glu + Tyr217Leu
Gln206Glu + Lys213Glu + Ala216Glu + Tyr217Leu
Ser204Glu + Gln206Glu + Ala216Glu + Tyr217Leu

Quintuple Mutation

Ile205Leu + Pro210Ala + Lys213Glu + Ala216Glu + Tyr217Leu
Ser204Glu + Gln206Glu + Lys213Glu + Ala216Glu + Tyr217Leu

II. Cleaning Compositions

In another embodiment of the present invention, an effective amount of one or more of the enzyme variants are included in compositions useful for cleaning a variety of surfaces in need of proteinaceous stain removal. Such such cleaning compositions include detergent compositions for cleaning hard surfaces, unlimited in form (e.g., liquid and granular); detergent compositions for cleaning fabrics, unlimited in form (e.g., granular, liquid and bar formulations); dishwashing compositions (unlimited in form); oral cleaning compositions, unlimited in form (e.g., dentifrice, toothpaste and mouthwash formulations); denture cleaning compositions, unlimited in form (e.g., liquid, tablet); and contact lens cleaning compositions, unlimited in form (e.g., liquid, tablet).

The cleaning compositions also comprise, in additin to the BPN' variants described hereinbefore, one or more cleaning composition materials compatible with the protease enzyme. the term "cleaning composition material", as used herein, means any liquid, solid or gaseous material selected for the particular type of cleaning composition desired and the form of the product (e.g., liquid, granule, bar, spray, stick, paste, gel), which materials are also compatible with the BPN' variant used in the composition. the specific selection of cleaning composition materials are readily made by considering the surface material to be cleaned, the desired form of the composition for the cleaning condition during use (e.g., through the wash detergent use). The term "compatible", as used herein, means the cleaning composition materials do not reduce the proteolytic activity of the BPN' variant to such an extent that the protease is not effective as desired during normal use situations. Specific cleaning composition materials are exemplified in detail hereinafter.

As used herein, "effective amount of enzyme variant" refers to the quantity of enzyme variant necessary to achieve the enzymatic activity necessary in the specific cleaning composition. Such effective amounts are readily ascertained by one of ordinary skill in the art and is based on many factors, such as the particular enzyme variant used, the cleaning application, the, specific composition of the cleaning composition, and whether a liquid or dry (e.g., granular, bar) composition is required, and the like. Preferably the cleaning compositions comprise from about 0.0001% to about 10% of one or more enzyme variants of the present invention, more preferably from about 0.001% to about 1%, more preferably still from about 0.01% to about 0.1%.

Several examples of various cleaning compositions wherein the enzyme variants may be employed are discussed in further detail below. All parts, percentages and ratios used herein are by weight unless otherwise specified.

As used herein, "non-fabric cleaning compositions" include hard surface cleaning compositions, dishwashing compositions, oral cleaning compositions, denture cleaning compositions and contact lens cleaning compositions.

A. Cleaning Compositions for Hard Surfaces, Dishes and Fabrics

The enzyme variants of the present invention can be used in a variety of detergent compositions where high sudsing and good insoluble substrate removal are desired. Thus the enzyme variants can be used with various conventional ingredients to provide fully-formulated hard-surface cleaners, dishwashing compositions, fabric laundering compositions and the like. Such compositions can be in the form of liquids, granules, bars and the like. Such compositions can be formulated as modem "concentrated" detergents which contain as much as 30%–60% by weight of surfactants.

The cleaning compositions herein can optionally, and preferably, contain various anionic, nonionic, zwitterionic, etc., surfactants. Such surfactants are typically present at levels of from about 5% to about 35% of the compositions.

Nonlimiting examples of surfactants useful herein include the conventional $C_{11}$–$C_{18}$ alkyl benzene sulfonates and primary and random alkyl sulfates, the $C_{10}$–$C_{18}$ secondary (2,3) alkyl sulfates of the formulas $CH_3(CH_2)x(CHOSO_3)^-M^+)CH_3$ and $CH_3(CH_2)y(CHOSO_3-M^+) CH_2CH_3$ wherein x and (y+1) are integers of at least about 7, preferably at least about 9, and M is a water-solubilizing cation, especially sodium, the $C_{10}$–$C_{18}$ alkyl alkoxy sulfates (especially EO 1–5 ethoxy sulfates), $C_{10}$–$C_{18}$ alkyl alkoxy carboxylates (especially the EO 1–5 ethoxycarboxylates), the $C_{10}$–$C_{18}$ alkyl polyglycosides, and their corresponding sulfated polyglycosides, $C_{12}$–$C_{18}$ alpha-sulfonated fatty acid esters, $C_{12}$–$C_{18}$ alkyl and alkyl phenol alkoxylates (especially ethoxylates and mixed ethoxy/propoxy), $C_{12}$–$C_{18}$ betaines and sulfobetaines ("sultaines"), $C_{10}$–$C_{18}$ amine oxides, and the like. The alkyl alkoxy sulfates (AES) and alkyl alkoxy carboxylates (AEC) are preferred herein. (Use of such surfactants in combination with the aforesaid amine oxide and/or betaine or sultaine surfactants is also preferred, depending on the desires of the formulator.) Other conventional useful surfactants are listed in standard texts. Particularly useful surfactants include. the $C_{10}$–$C_{18}$ N-methyl glucamides disclosed in U.S. Pat. No. 5, 194,639, Connor et al., issued Mar. 16, 1993, incorporated herein by reference.

A wide variety of other ingredients useful in detergent cleaning compositions can be included in the compositions herein, including other active ingredients, carriers, hydrotropes, processing aids, dyes or pigments, solvents for liquid formulations, etc. If an additional increment of sudsing is desired, suds boosters such as the $C_{10}$–$C_{16}$, alkolamides can be incorporated into the compositions, typically at about 1% to about 10% levels. The $C_{10}$–$C_{14}$ monoethanol and diethanol amides illustrate a typical class of such suds boosters. Use of such suds boosters with high sudsing adjunct surfactants such as the amine oxides, betaines and sultaines noted above is also advantageous. If desired, soluble magnesium salts such as $MgCl_2$, $MgSO_4$, and the like, can be added at levels of, typically, from about 0.1% to about 2%, to provide additionally sudsing.

The liquid detergent compositions herein can contain water and other solvents as carriers. Low molecular weight primary or secondary alcohols exemplified by methanol, ethanol, propanol, and isopropanol are suitable. Monohydric alcohols are preferred for solubilizing surfactants, but polyols such as those containing from about 2 to about 6 carbon atoms and from about 2 to about 6 hydroxy groups (e.g., 1,3-propanediol, ethylene glycol, glycerine, and 1,2-propanediol) can also be used. The compositions may contain from about 5% to about 90%, typically from about 10% to about 50% of such carriers.

The detergent compositions herein will preferably be formulated such that during use in aqueous cleaning operations, the wash water will have a pH between about 6.8 and about 11.0. Finished products thus are typically formulated at this range. Techniques for controlling pH at recommended usage levels include the use of buffers, alkalis, acids, etc., and are well known to those skilled in the art.

When formulating the hard surface cleaning compositions and fabric cleaning compositions of the present invention, the formulator may wish to employ various builders at levels from about 5% to about 50% by weight. Typical builders include the 1–10 micron zeolites, polycarboxylates such as citrate and oxydisuccinates, layered silicates, phosphates, and the like. Other conventional builders are listed in standard formularies.

Likewise, the formulator may wish to employ various additional enzymes, such as cellulases, lipases, amylases and proteases in such compositions, typically at levels of from about 0.001% to about 1% by weight. Various detersive and fabric care enzymes are well-known in the laundry detergent art.

Various bleaching compounds, such as the percarbonates, perborates and the like, can be used in such compositions, typically at levels from about 1% to about 15% by weight. If desired, such compositions can also contain bleach activators-such as tetraacetyl ethylenediamine, nonanoyloxybenzene sulfonate, and the like, which are also known in the art. Usage levels typically range from about 1% to about 10% by weight.

Various soil release agents, especially of the anionic oligoester type, various chelating agents, especially the aminophosphonates and ethylenediaminedisuccinates, various clay soil removal agents, especially ethoxylated tetraethylene pentamine, various dispersing agents, especially polyacrylates and polyasparatates, various brighteners, especially anionic brighteners, various suds suppressors, especially silicones and secondary alcohols, various fabric softeners, especially smectite clays, and the like can all be used in such compositions at levels ranging from about 1% to about 35% by weight. Standard. formularies and published patents contain multiple, detailed descriptions of such conventional materials.

Enzyme stabilizers may also be used in the cleaning compositions. Such enzyme stabilizers include propylene glycol (preferably from about 1% to about 10%), sodium formate (preferably from about 0.1% to about. 1%) and calcium formate (preferably from about 0.1% to about 1%).

1. Hard Surface Cleaning Compositions

As used herein "hard surface cleaning composition" refers to liquid and granular detergent compositions for cleaning hard surfaces such as floors, walls, bathroom tile, and the like. Hard surface cleaning compositions of the present invention comprise an effective amount of one or more enzyme variants of the present invention, preferably from about 0.001% to about 10%, more preferably from about 0.01% to about 5%, more preferably still from about 0.05% to about 1% by weight of active enzyme of the composition. In addition to comprising one or more of the enzyme variants, such hard surface cleaning compositions typically comprise a surfactant and a water-soluble sequestering builder. In certain specialized products such as spray window cleaners, however, the surfactants are sometimes not used since they may produce a filmy/streaky residue on the glass surface.

The surfactant component, when present, may comprise as little as 0.1% of the compositions herein, but typically the compositions will contain from about 0.25% to about 10%, more preferably from about 1% to about 5% of surfactant.

Typically the compositions will contain from about 0.5% to about 50% of a detergency builder, preferably from about 1% to about1.0%.

Preferably the pH should be in the range of about 8 to 12. Conventional pH adjustment agents such as sodium hydroxide, sodium carbonate or hydrochloric acid can be used if adjustment is necessary.

Solvents may be included in the compositions. Useful solvents include, but are not limited to, glycol ethers such as diethyleneglycol monohexyl ether, diethyleneglycol monobutyl ether, ethyleneglycol monobutyl ether, ethyleneglycol monohexyl ether, propyleneglycol monobutyl ether, dipropyleneglycol monobutyl ether, and diols such as 2,2,4-trimethyl-1,3-pentanediol and 2-ethyl-1,3-hexanediol. When used, such solvents are typically present at levels of from about. 0.5% to about 15%, preferably from bout 3% to about 11%.

Additionally, highly volatile solvents such as isopropanol or ethanol can be used in the present compositions to facilitate faster evaporation of the composition from surfaces when the surface is not rinsed after "full strength" application of the composition to the surface. When used, volatile solvents are typically present at levels of from about 2% to about 12% in the compositions.

The hard surface cleaning composition embodiment of the present invention is illustrated by the following examples.

EXAMPLES 7–12

Liquid Hard Surface Cleaning Compositions

| Component | Example No. | | | | | |
|---|---|---|---|---|---|---|
| | 7 | 8 | 9 | 10 | 11 | 12 |
| Lys213Glu | 0.05 | 0.50 | 0.02 | 0.03 | 0.10 | 0.03 |
| Ile205Leu + Ala216Asp | — | — | — | — | 0.20 | 0.02 |
| Na$_2$DIDA* | | | | | | |
| EDTA** | — | — | 2.90 | 2.90 | — | — |
| Na Citrate | — | — | — | — | 2.90 | 2.90 |
| NaC$_{12}$ Alkyl-benzene sulfonate | 1.95 | — | 1.95 | — | 1.95 | — |
| NaC$_{12}$ Alkylsulfate | — | 2.20 | — | 2.20 | — | 2.20 |
| NaC$_{12}$(ethoxy)*** sulfate | — | 2.20 | — | 2.20 | — | 2.20 |
| C$_{12}$ Dimethylamine oxide | — | 0.50 | — | 0.50 | — | 0.50 |
| Na Cumene sulfonate | 1.30 | — | 1.30 | — | 1.30 | — |
| Hexyl Carbitol*** | 6.30 | 6.30 | 6.30 | 6.30 | 6.30 | 6.30 |
| Water**** | balance to 100% | | | | | |

*Disodium N-diethyleneglycol-N,N-iminodiacetate
**Na$_4$ ethylenediamine diacetic acid
***Diethyleneglycol monohexyl ether
****All formulas adjusted to pH 7

In Examples 7–10, the BPN' variants recited in Table 2, among others, are substituted for Lys213Glu, with substantially similar results.

In Examples 11–12, any combination of the BPN' variants recited in Table 2, among others, are substituted for Lys2l3Glu and Ile2O5Leu+Ala216Asp, with substantially similar results.

EXAMPLES 13–18

Spray Compositions for Cleaning Hard Surfaces and Removing Household Mildew

| Component | Example No. | | | | | |
|---|---|---|---|---|---|---|
| | 13 | 14 | 15 | 16 | 17 | 18 |
| Lys213Glu + Tyr217Leu | 0.50 | 0.05 | 0.60 | 0.30 | 0.20 | 0.30 |
| Ala216Glu | — | — | — | — | 0.30 | 0.10 |
| Sodium octyl sulfate | 2.00 | 2.00 | 2.00 | 2.00 | 2.00 | 2.00 |
| Sodium dodecyl sulfate | 4.00 | 4.00 | 4.00 | 4.00 | 4.00 | 4.00 |
| Sodium hydroxide | 0.80 | 0.80 | 0.80 | 0.80 | 0.80 | 0.80 |
| Silicate (Na) | 0.04 | 0.04 | 0.04 | 0.04 | 0.04 | 0.04 |
| Perfume | 0.35 | 0.35 | 0.35 | 0.35 | 0.35 | 0.35 |
| Water | balance to 100% | | | | | |

Product pH is about 7.

In Examples 13–16, the BPN' variants recited in Tables 2–12, among others, are substituted for Lys213Glu+Tyr217Leu, with substantially similar results.

In Examples 17–18, any combination of the BPN' variants recited in Tables 2–12, among others, are substituted for Lys213Glu +Tyr217Leu and Ala216Glu, with substantially similar results.

2. Dishwashing Compositions

In another embodiment of the present invention, dishwashing compositions comprise one or more enzyme variants of the present invention. As used herein, "dishwashing composition" refers to all forms for compositions for cleaning dishes, including but not limited to, granular and liquid forms. The dishwashing composition embodiment of the present invention is illustrated by the following examples.

EXAMPLES 19–24

Dishwashing Composition

| Component | Example No. | | | | | |
|---|---|---|---|---|---|---|
| | 19 | 20 | 21 | 22 | 23 | 24 |
| Glu206Pro + Gly211Ala + Ala216Glu | 0.05 | 0.50 | 0.02 | 0.40 | 0.10 | 0.03 |
| Ile205Leu + Ala216Asp | — | — | — | — | 0.40 | 0.02 |
| $C_{12}$–$C_{14}$ N-methylglucamide | 0.90 | 0.90 | 0.90 | 0.90 | 0.90 | 0.90 |
| $C_{12}$ ethoxy (1) sulfate | 12.00 | 12.00 | 12.00 | 12.00 | 12.00 | 12.00 |
| 2-methyl undecanoic acid | 4.50 | 4.50 | 4.50 | 4.50 | 4.50 | 4.50 |
| $C_{12}$ ethoxy (2) carboxylate | 4.50 | 4.50 | 4.50 | 4.50 | 4.50 | 4.50 |
| $C_{12}$ alcohol ethoxylate (4) | 3.00 | 3.00 | 3.00 | 3.00 | 3.00 | 3.00 |
| $C_{12}$ amine oxide | 3.00 | 3.00 | 3.00 | 3.00 | 3.00 | 3.00 |
| Sodium cumene sulfonate | 2.00 | 2.00 | 2.00 | 2.00 | 2.00 | 2.00 |
| Ethanol | 4.00 | 4.00 | 4.00 | 4.00 | 4.00 | 4.00 |
| $Mg^{++}$ (as $MgCl_2$) | 0.20 | 0.20 | 0.20 | 0.20 | 0.20 | 0.20 |
| $Ca^{++}$ (as $CaCl_2$) | 0.40 | 0.40 | 0.40 | 0.40 | 0.40 | 0.40 |
| Water | balance to 100% | | | | | |

Product pH is adjusted to 7.

In Examples 19–22, the BPN' variants recited in Tables 2–12, among others, are substituted for Gln206Pro+Gly211Ala+Ala216Glu, with substantially similar results.

In Examples 23–24, any combination of the BPN' variants recited in Tables 2–12, among others, are substituted for Gln2O6Pro+Gly211Ala+Ala216Glu and Ile205Leu+Ala216Asp, with substantially similar results.

3. Fabric Cleaning Compositions

In another embodiment of the present invention, fabric cleaning compositions comprise one or more enzyme variants of the present invention. As used herein, "fabric cleaning composition" refers to all forms for detergent compositions for cleaning fabrics, including but not limited to, granular, liquid and bar forms. Preferred fabric cleaning compositions are those in the liquid form.

a. Granular Fabric Cleaning Compositions

The granular fabric cleaning compositions of the present invention contain an effective amount of one or more enzyme variants of the present invention, preferably from about 0.001% to about 10%, more preferably from about 0.005% to about 5%, more preferably from about 0.01% to about 1% by weight of active enzyme of the composition. In addition to one or more enzyme variants, the granular fabric cleaning compositions typically comprise at least one surfactant, one or more builders, and, in some cases, a bleaching agent.

The granular fabric cleaning composition embodiment of the present invention is illustrated by the following examples.

EXAMPLES 25–28

Granular Fabric Cleaning Composition

| Component | Example No. | | | |
|---|---|---|---|---|
| | 25 | 26 | 27 | 28 |
| Ala216Asp | 0.10 | 0.20 | 0.03 | 0.05 |
| Ala216Gly | — | — | 0.02 | 0.05 |
| $C_{13}$ linear alkyl benzene sulfonate | 22.00 | 22.00 | 22.00 | 22.00 |
| Phosphate (as sodium tripolyphosphates) | 23.00 | 23.00 | 23.00 | 23.00 |
| Sodium carbonate | 23.00 | 23.00 | 23.00 | 23.00 |
| Sodium silicate | 14.00 | 14.00 | 14.00 | 14.00 |
| Zeolite | 8.20 | 8.20 | 8.20 | 8.20 |
| Chelant (diethylaenetriaminepentaacetic acid) | 0.40 | 0.40 | 0.40 | 0.40 |
| Sodium sulfate | 5.50 | 5.50 | 5.50 | 5.50 |
| Water | balance to 100% | | | |

In Examples 25–26, the BPN' variants recited in Tables 2–12, among others, are substituted for Ala216Asp, with substantially similar results.

In Examples 27–28, any combination of the BPN' variants recited in Tables 2–12, among others, are substituted for Ala216Asp and Ala216Gly, with substantially similar results.

EXAMPLES 29–32

Granular Fabric Cleaning Composition

| Component | Example No. | | | |
|---|---|---|---|---|
| | 29 | 30 | 31 | 32 |
| Lys213Glu + Ala216Glu + Tyr217Leu | 0.10 | 0.20 | 0.03 | 0.05 |
| Ile205Val + Pro210Ala + Lys213Glu | — | — | 0.02 | 0.05 |
| $C_{12}$ alkyl benzene sulfonate | 12.00 | 12.00 | 12.00 | 12.00 |
| Zeolite A (1–10 micrometer) | 26.00 | 26.00 | 26.00 | 26.00 |
| 2-butyl octanoic acid | 4.00 | 4.00 | 4.00 | 4.00 |
| $C_{12}$–$C_{14}$ secondary (2,3) alkyl sulfate, Na salt | 5.00 | 5.00 | 5.00 | 5.00 |
| Sodium citrate | 5.00 | 5.00 | 5.00 | 5.00 |
| Optical brightener | 0.10 | 0.10 | 0.10 | 0.10 |
| Sodium sulfate | 17.00 | 17.00 | 17.00 | 17.00 |
| Water and minors | balance to 100% | | | |

In Examples 29–30, the BPN' variants recited in Tables 2–12, among others, are substituted for Lys213Glu + Ala216Glu + Tyr217Leu, with substantially similar results.

In Examples 31–32, any combination of the BPN' variants recited in Tables 2–12, among others, are substituted for Lys213Glu + Ala216Glu + Tyr217Leu and lle205Val + Pro210Ala + Lys213Glu, with substantially similar results.

EXAMPLES 33–36

Granular Fabric Cleaning Composition

| Component | \# 33 | \# 34 | \# 35 | \# 36 |
|---|---|---|---|---|
| Ala216Glu | 0.10 | 0.20 | 0.03 | 0.05 |
| Gln206Glu + Tyr217Leu | — | — | 0.02 | 0.05 |
| $C_{13}$ linear alkyl benzene sulfonate | 22.00 | 22.00 | 22.00 | 22.00 |
| Phosphate (as sodium tripolyphospates) | 23.00 | 23.00 | 23.00 | 23.00 |
| Sodium carbonate | 23.00 | 23.00 | 23.00 | 23.00 |
| Sodium silicate | 14.00 | 14.00 | 14.00 | 14.00 |
| Zeolite | 8.20 | 8.20 | 8.20 | 8.20 |
| Chelant (diethylaenetriamine-pentaacetic acid) | 0.40 | 0.40 | 0.40 | 0.40 |
| Sodium sulfate | 5.50 | 5.50 | 5.50 | 5.50 |
| Water | balance to 100% | | | |

In Examples 33–34, the BPN' variants recited in Tables 2–12, among others, are substituted for Ala216Glu, with substantially similar results.

In Examples 35–36, any combination of the BPN' variants recited in Tables 2–12, among others, are substituted for Ala216Glu and Gln206Glu+Tyr217Leu, with substantially similar results.

EXAMPLES 37–40

Granular Fabric Cleaning Composition

| Component | \# 37 | \# 38 | \# 39 | \# 40 |
|---|---|---|---|---|
| Gln206Glu + Ala216Glu + Tyr217Leu | 0.10 | 0.20 | 0.03 | 0.05 |
| Pro210Ala + Gly215Thr | — | — | 0.02 | 0.05 |
| $C_{12}$ alkyl benzene sulfonate | 12.00 | 12.00 | 12.00 | 12.00 |
| Zeolite A (1–10 micrometer) | 26.00 | 26.00 | 26.00 | 26.00 |
| 2-butyl octanoic acid | 4.00 | 4.00 | 4.00 | 4.00 |
| $C_{12}$–$C_{14}$ secondary (2,3) alkyl sulfate, Na salt | 5.00 | 5.00 | 5.00 | 5.00 |
| Sodium citrate | 5.00 | 5.00 | 5.00 | 5.00 |
| Optical brightener | 0.10 | 0.10 | 0.10 | 0.10 |
| Sodium sulfate | 17.00 | 17.00 | 17.00 | 17.00 |
| Water and minors | balance to 100% | | | |

In Examples 37–38, the BPN' variants recited in Tables 2–12, among others, are, substituted for Gln216Glu+Ala216Glu+Tyr217Leu, with substantially similar results.

In Examples 39–40, any combination of the BPN' variants recited in Tables 2–12, among others, are substituted for Gln206Glu+Ala216Glu+Tyr217Leu and Pro210Ala+Gly215Thr, with substantially similar results.

Examples 41–42
Granular Fabric Cleaning Composition

| Component | 41 | 42 |
|---|---|---|
| Linear alkyl benzene sulphonate | 11.4 | 10.70 |
| Tallow alkyl sulphate | 1.80 | 2.40 |
| $C_{14-15}$ alkyl sulphate | 3.00 | 3.10 |
| $C_{14-15}$ alcohol 7 times ethoxylated | 4.00 | 4.00 |
| Tallow alcohol 11 times ethoxylated | 1.80 | 1.80 |
| Dispersant | 0.07 | 0.1 |
| Silicone fluid | 0.80 | 0.80 |
| Trisodium citrate | 14.00 | 15.00 |
| Citric acid | 3.00 | 2.50 |
| Zeolite | 32.50 | 32.10 |

Examples 41–42
Granular Fabric Cleaning Composition

| Component | 41 | 42 |
|---|---|---|
| Maleic acid acrylic acid copolymer | 5.00 | 5.00 |
| Diethylene triamine penta methylene phosphonic acid | 1.00 | 0.20 |
| Ala216Glu + Tyr217Leu | 0.30 | 0.30 |
| Lipase | 0.36 | 0.40 |
| Amylase | 0.30 | 0.30 |
| Sodium silicate | 2.00 | 2.50 |
| Sodium sulphate | 3.50 | 5.20 |
| Polyvinyl pyrrolidone | 0.30 | 0.50 |
| Perborate | 0.5 | 1 |
| Phenol sulphonate | 0.1 | 0.2 |
| Peroxidase | 0.1 | 0.1 |
| Minors | Up to 100 | Up to 100 |

Example 43–44
Granular Fabric Cleaning Composition

| Component | 43 | 44 |
|---|---|---|
| Sodium linear $C_{12}$ alkyl benzene-sulfonate | 6.5 | 8.0 |
| Sodium sulfate | 15.0 | 18.0 |
| Zeolite A | 26.0 | 22.0 |
| Sodium nitrilotriacetate | 5.0 | 5.0 |
| Polyvinyl pyrrolidone | 0.5 | 0.7 |
| Tetraacetylethylene diamine | 3.0 | 3.0 |
| Boric acid | 4.0 | — |
| Perborate | 0.5 | 1 |
| Phenol sulphonate | 0.1 | 0.2 |
| Ile205Leu + Ala216Glu | 0.4 | 0.4 |
| Fillers (e.g., silicates; carbonates; perfumes; water | Up to 100 | Up to 100 |

Example 45
Compact Granular Fabric Cleaning Composition

| Component | Weight % |
|---|---|
| Alkyl Sulphate | 8.0 |
| Alkyl Ethoxy Sulphate | 2.0 |
| Mixture of $C_{25}$ and $C_{45}$ alcohol 3 and 7 times ethoxylated | 6.0 |
| Polyhydroxy fatty acid amide | 2.5 |
| Zeolite | 17.0 |
| Layered silicate/citrate | 16.0 |
| Carbonate | 7.0 |
| Maleic acid acrylic acid copolymer | 5.0 |
| Soil release polymer | 0.4 |
| Carboxymethyl cellulose | 0.4 |
| Poly (4-vinylpyridine) -N-oxide | 0.1 |
| Copolymer of vinylimidazole and vinylpyrrolidone | 0.1 |
| PEG2000 | 0.2 |
| Val203Glu + Gln206Glu + Ala216Glu + Tyr217Leu | 0.5 |
| Lipase | 0.2 |
| Cellulase | 0.2 |
| Tetraacetylethylene diamine | 6.0 |
| Percarbonate | 22.0 |
| Ethylene diamine disuccinic acid | 0.3 |
| Suds suppressor | 3.5 |
| Disodium-4,4'-bis (2-morpholino -4-anilino-s-triazin-6-ylamino) stilbene-2,2'-disulphonate | 0.25 |

Example 45
Compact Granular Fabric Cleaning Composition

| Component | Weight % |
|---|---|
| Disodium-4,4'-bis (2-sulfostyril) biphenyl | 0.05 |
| Water, Perfume and Minors | Up to 100 |

Example 46
Granular Fabric Cleaning Composition

| Component | Weight % |
|---|---|
| Linear alkyl benzene sulphonate | 7.6 |
| $C_{16}$–$C_{18}$ alkyl sulfate | 1.3 |
| $C_{14-15}$ alcohol 7 times ethoxylated | 4.0 |
| Coco-alkyl-dimethyl hydroxyethyl ammonium chloride | 1.4 |
| Dispersant | 0.07 |
| Silicone fluid | 0.8 |
| Trisodium citrate | 5.0 |
| Zeolite 4A | 15.0 |
| Maleic acid acrylic acid copolymer | 4.0 |
| Diethylene triamine penta methylene phosphonic acid | 0.4 |
| Perborate | 15.0 |
| Tetraacetylethylene diamine | 5.0 |
| Smectite clay | 10.0 |
| Poly (oxy ethylene) (MW 300,000) | 0.3 |
| Tyr214Phe + Tyr217Asn | 0.4 |
| Lipase | 0.2 |
| Amylase | 0.3 |
| Cellulase | 0.2 |
| Sodium silicate | 3.0 |
| Sodium carbonate | 10.0 |
| Carboxymethyl cellulose | 0.2 |
| Brighteners | 0.2 |
| Water, perfume and minors | Up to 100 |

Example 47
Granular Fabric Cleaning Composition

| Component | Weight % |
|---|---|
| Linear alkyl benzene sulfonate | 6.92 |
| Tallow alkyl sulfate | 2.05 |
| $C_{14-15}$ alcohol 7 times ethoxylated | 4.4 |
| $C_{12-15}$ alkyl ethoxy sulfate - 3 times ethoxylated | 0.16 |
| Zeolite | 20.2 |
| Citrate | 5.5 |
| Carbonate | 15.4 |
| Silicate | 3.0 |
| Maleic acid acrylic acid copolymer | 4.0 |
| Carboxymethyl cellulose | 0.31 |
| Soil release polymer | 0.30 |
| Val203Glu + Pro210Ala + Gly215Thr + Ala216Glu + Tyr217Leu | 0.2 |
| Lipase | 0.36 |
| Cellulase | 0.13 |
| Perborate tetrahydrate | 11.64 |
| Perborate monohydrate | 8.7 |
| Tetraacetylethylene diamine | 5.0 |
| Diethylene tramine penta methyl phosphonic acid | 0.38 |
| Magnesium sulfate | 0.40 |
| Brightener | 0.19 |
| Perfume, silicone, suds suppressors | 0.85 |
| Minors | Up to 100 | b. Liquid Fabric Cleaning Compositions

Liquid fabric cleaning compositions of the present invention comprise an effective amount of one or more enzyme variants of the present invention, preferably from about 0.005% to about 5%, more preferably from about 0.01% to about 1%, by weight of active enzyme of the composition. Such liquid fabric cleaning compositions typically additionally comprise an anionic surfactant, a fatty acid, a water-soluble detergency builder and water.

The liquid fabric cleaning composition embodiment of the present invention is illustrated by the following examples.

Examples 48–52
Liquid Fabric Cleaning Compositions

| Component | 48 | 49 | 50 | 51 | 52 |
|---|---|---|---|---|---|
| Pro210Ala + Gly215Thr | 0.05 | 0.03 | 0.30 | 0.03 | 0.10 |
| Pro210Ala + Lys213Glu + Ala216Glu + Tyr217Leu | — | — | — | 0.01 | 0.20 |
| $C_{12}$–$C_{14}$ alkyl sulfate, Na | 20.00 | 20.00 | 20.00 | 20.00 | 20.00 |
| 2-butyl octanoic acid | 5.00 | 5.00 | 5.00 | 5.00 | 5.00 |
| Sodium citrate | 1.00 | 1.00 | 1.00 | 1.00 | 1.00 |
| $C_{10}$ alcohol ethoxylate (3) | 13.00 | 13.00 | 13.00 | 13.00 | 13.00 |
| Monethanolamine | 2.50 | 2.50 | 2.50 | 2.50 | 2.50 |
| Water/propylene glycol/ethanol (100:1:1) | balance to 100% | | | | |

In Examples 48–50 the BPN' variants recited in Tables 2–12, among others, are substituted for Pro210Ala+Gly215Thr, with substantially similar results.

In Examples 51–52, any combination of the BPN' variants recited in Tables 2–12, among others, are substituted for Pro210Ala+Gly215Thr and Pro210Ala+Lys213Glu+Ala216Glu+Tyr217Leu, with substantially similar results.

Examples 53–57
Liquid Fabric Cleaning Compositions

| Component | 53 | 54 | 55 | 56 | 57 |
|---|---|---|---|---|---|
| Gln206Glu + Ala216Glu + Tyr217Leu | 0.05 | 0.03 | 0.30 | 0.03 | 0.10 |
| Pro210Ala + Gly215Thr | — | — | — | 0.01 | 0.20 |
| $C_{12}$–$C_{14}$ alkyl sulfate, Na | 20.00 | 20.00 | 20.00 | 20.00 | 20.00 |
| 2-butyl octanoic acid | 5.00 | 5.00 | 5.00 | 5.00 | 5.00 |
| Sodium citrate | 1.00 | 1.00 | 1.00 | 1.00 | 1.00 |
| $C_{10}$ alcohol ethoxylate (3) | 13.00 | 13.00 | 13.00 | 13.00 | 13.00 |
| Monoethanolamine | 2.50 | 2.50 | 2.50 | 2.50 | 2.50 |
| Water/propylene glycol/ethanol (100:1:1) | balance to 100% | | | | |

In Examples 53–55 the BPN' variants recited in Tables 2–12, among others, are substituted for Gln206Glu+Ala216Glu+Tyr217Leu, with substantially similar results.

In Examples 56–57, any combination of the BPN' variants recited in Tables 212, among others, are substituted for Gln206Glu+Ala216Glu+Tyr217Leu and Pro210Ala+Gly215Thr, with substantially similar results.

Examples 58–59
Granular Fabric Cleaning Composition

| Component | 58 | 59 |
|---|---|---|
| $C_{12-14}$ alkenyl succinic acid | 3.0 | 8.0 |
| Citric acid monohydrate | 10.0 | 15.0 |

-continued

Examples 58–59
Granular Fabric Cleaning Composition

| Component | Example No. 58 | Example No. 59 |
|---|---|---|
| Sodium $C_{12-15}$ alkyl sulphate | 8.0 | 8.0 |
| Sodium sulfate of $C_{12-15}$ alcohol 2 times ethoxylated | — | 3.0 |
| $C_{12-15}$ alcohol 7 times ethoxylated | — | 8.0 |
| $C_{12-15}$ alcohol 5 times ethoxylated | 8.0 | — |
| Diethylene triamine penta (methylene phosphonic acid) | 0.2 | — |
| Oleic acid | 1.8 | — |
| Ethanol | 4.0 | 4.0 |
| Propanediol | 2.0 | 2.0 |
| Ala216Glu + Tyr217Leu | 0.2 | 0.2 |
| Polyvinyl pyrrolidone | 1.0 | 2.0 |
| Suds suppressor | 0.15 | 0.15 |
| NaOH | up to pH 7.5 | |
| Perborate | 0.5 | 1 |
| Phenol sulphonate | 0.1 | 0.2 |
| Peroxidase | 0.4 | 0.1 |
| Waters and minors | up to 100 parts | |

In each of Examples 58 and 59 herein, the BPN' variants recited in Tables 2–12, among others, are substituted for Ala216Glu+Tyr217Leu, with substantially similar results.

Examples 60–62
Liquid Fabric Cleaning Composition

| Component | Example No. 60 | Example No. 61 | Example No. 62 |
|---|---|---|---|
| Citric Acid | 7.10 | 3.00 | 3.00 |
| Fatty Acid | 2.00 | — | 2.00 |
| Ethanol | 1.93 | 3.20 | 3.20 |
| Boric Acid | 2.22 | 3.50 | 3.50 |
| Monoethanolamine | 0.71 | 1.09 | 1.09 |
| 1,2 Propanediol | 7.89 | 8.00 | 8.00 |
| NaCumene Sulfonate | 1.80 | 3.00 | 3.00 |
| NaFormate | 0.08 | 0.08 | 0.08 |
| NaOH | 6.70 | 3.80 | 3.80 |
| Silicon anti-foam agent | 1.16 | 1.18 | 1.18 |
| Ala216Glu | 0.0145 | — | — |
| Ala216Glu + Tyr217Leu | — | 0.0145 | — |
| Gln206Glu + Ala216Glu + Tyr217Leu | — | — | 0.0145 |
| Lipase | 0.200 | 0.200 | 0.200 |
| Cellulase | — | 7.50 | 7.50 |
| Soil release polymer | 0.29 | 0.15 | 0.15 |
| Anti-foaming agents | 0.06 | 0.085 | 0.085 |
| Brightener 36 | 0.095 | — | — |
| Brightener 3 | — | 0.05 | 0.05 |
| $C_{12}$ alkyl benzenesulfonic acid | 9.86 | — | — |
| $C_{12-15}$ alkyl polyethoxylate (2.5) sulfate | 13.80 | 18.00 | 18.00 |
| $C_{12}$ glucose amide | — | 5.00 | 5.00 |
| $C_{12-13}$ alkyl polyethoxylate (9) | 2.00 | 2.00 | 2.00 |
| Water, perfume and minors | balance to 100% | | |

C. Bar Fabric Cleaning Compositions

Bar fabric cleaning compositions of the present invention suitable for hand-washing soiled fabrics contain an effective, amount of one or more enzyme variants of the present invention, preferably from about 0.001% to about 10%, more preferably from about 0.01% to about 1% by weight of the composition.

The bar fabric cleaning composition embodiment of the present invention is illustrated by the following examples.

Examples 63–66
Bar Fabric Cleaning Compositions

| Component | 63 | 64 | 65 | 66 |
|---|---|---|---|---|
| Lys213Glu + Ala216Glu | 0.3 | — | 0.1 | 0.02 |
| Tyr214Phe + Tyr217Asn | — | — | 0.4 | 0.03 |
| $C_{12}$–$C_{16}$ alkyl sulfate, Na | 20.0 | 20.0 | 20.0 | 20.00 |
| $C_{12}$–$C_{14}$ methyl glucamide | 5.0 | 5.0 | 5.0 | 5.00 |
| $C_{11}$–$C_{13}$ alkyl benzene sulfonate, Na | 10.0 | 10.0 | 10.0 | 10.00 |
| Sodium carbonate | 25.0 | 25.0 | 25.0 | 25.00 |
| Sodium pyrophosphate | 7.0 | 7.0 | 7.0 | 7.00 |
| Sodium tripolyphosphate | 7.0 | 7.0 | 7.0 | 7.00 |
| Zeolite A (0.1–10 $\mu$) | 5.0 | 5.0 | 5.0 | 5.00 |
| Carboxymethylcellulose | 0.2 | 0.2 | 0.2 | 0.20 |
| Polyacrylate (MW 1400) | 0.2 | 0.2 | 0.2 | 0.20 |
| Coconut monethanolamide | 5.0 | 5.0 | 5.0 | 5.00 |
| Brightener, perfume | 0.2 | 0.2 | 0.2 | 0.20 |
| $CaSO_4$ | 1.0 | 1.0 | 1.0 | 1.00 |
| $MgSO_4$ | 1.0 | 1.0 | 1.0 | 1.00 |
| Water | 4.0 | 4.0 | 4.0 | 4.00 |
| Filler* | balance to 100% | | | |

*Can be selected from convenient materials such as $CaCO_3$, talc, clay, silicates, and the like.

In Examples 63–64 the BPN' variants recited in Tables 2–12, among others, are substituted for Lys213Glu+Ala216Glu, with substantially similar results.

In Examples 65–66, any combination of the BPN' variants recited in Tables 2–12, among others, are substituted for Lys213Glu+Ala216Glu and Tyr214Phe+Tyr217Asn, with substantially similar results.

Examples 67–70
Bar Fabric Cleaning Compositions

| Component | 67 | 68 | 69 | 70 |
|---|---|---|---|---|
| Val203Glu | 0.3 | — | 0.1 | 0.02 |
| Tyr214Phe + Tyr217Asn | — | 0.3 | 0.4 | 0.03 |
| $C_{12}$–$C_{16}$ alkyl sulfate, Na | 20.0 | 20.0 | 20.0 | 20.00 |
| $C_{12}$–$C_{14}$ N-methyl glucamide | 5.0 | 5.0 | 5.0 | 5.00 |
| $C_{11}$–$C_{13}$ alkyl benzene sulfonate, Na | 10.0 | 10.0 | 10.0 | 10.00 |
| Sodium carbonate | 25.0 | 25.0 | 25.0 | 25.00 |
| Sodium pyrophosphate | 7.0 | 7.0 | 7.0 | 7.00 |
| Sodium tripolyphosphate | 7.0 | 7.0 | 7.0 | 7.00 |
| Zeolite A (0.1–.10 $\mu$) | 5.0 | 5.0 | 5.0 | 5.00 |
| Carboxymethylcellulose | 0.2 | 0.2 | 0.2 | 0.20 |
| Polyacrylate (MW 1400) | 0.2 | 9.2 | 0.2 | 0.20 |
| Coconut monethanolamide | 5.0 | 5.0 | 5.0 | 5.00 |
| Brightener, perfume | 0.2 | 0.2 | 0.2 | 0.20 |
| $CaSO_4$ | 1.0 | 1.0 | 1.0 | 1.00 |
| $MgSO_4$ | 1.0 | 1.0 | 1.0 | 1.00 |
| Water | 4.0 | 4.0 | 4.0 | 4.00 |
| Filler* | balance to 100% | | | |

*Can be selected from convenient materials such as $CaCO_3$, talc, clay, silicates, and the like.

In Example 67, the BPN' variants recited in Tables 2–12, among others, are substituted for Val203Glu, with substantially similar results.

In Example 68, the BPN' variants recited in Tables 2–12, among others, are substituted for Tyr214Phe+Tyr217Asn, with substantially similar results.

In Examples 69–70, any combination of the BPN' variants recited in Tables 2–12, among others, are substituted for Val203Glu and Tyr214Phe+Tyr217Asn, with substantially similar results.

B. Additional Cleaning Compositions

In addition to the hard surface cleaning, dishwashing and fabric cleaning compositions discussed above, one or more enzyme variants of the present invention may be incorporated into a variety of other cleaning compositions where hydrolysis of an insoluble substrate is desired. Such additional cleaning compositions include but are not limited to, oral cleaning compositions, denture cleaning compositions, and contact lens cleaning compositions.

1. Oral Cleaning Compositions

In another embodiment of the present invention, a pharmaceutically-acceptable amount of one or more enzyme variants of the present invention are included in compositions useful for removing proteinaceous stains from teeth or dentures. As used herein, "oral cleaning compositions" refers to dentifrices, toothpastes, toothgels, toothpowders, mouthwashes, mouth sprays, mouth gels, chewing gums, lozenges, sachets, tablets, biogels, prophylaxis pastes, dental treatment solutions, and the like. Preferably, the oral, cleaning compositions comprise from about 0.0001% to about 20% of one or more enzyme variants of the present invention, more preferably from about 0.001% to about 10%, more preferably still from about 0.01% to about 5%, by weight of the composition, and, a pharmaceutically-acceptable carrier. As used herein, "pharmaceutically-acceptable" means that drugs, medicaments or inert ingredients which the term describes are suitable for use in contact with the tissues of humans and lower animals without undue toxicity, incompatibility, instability, irritation, allergic response, and the like, commensurate with a reasonable benefit/risk ratio.

Typically, the pharmaceutically-acceptable oral cleaning carrier components of the oral cleaning components of the oral cleaning compositions will generally comprise from about 50%. to about 99.99%, preferably from about 65% to about 99.99%, more preferably from about 65% to about 99%, by weight of the composition.

The pharmaceutically-acceptable carrier components and optional components which may be included in the oral cleaning compositions of the present invention are well known to those skilled in the art. A wide variety of composition types, carrier components and optional components useful in the oral cleaning compositions are disclosed in U.S. Pat. No. 5,096,700, Seibel, issued Mar. 17, 1992; U.S. Pat. No. 5,028,414, Sampathkumar, issued Jul. 2, 1991; and U.S. Pat. No. 5,028,415, Benedict, Bush and Sunberg, issued Jul. 2, 1991; all of which are incorporated herein by reference.

The oral cleaning composition embodiment of the present invention is illustrated by the following examples.

Examples 71–74
Dentifrice Composition

| Component | Example No. 71 | 72 | 73 | 74 |
|---|---|---|---|---|
| Ile205Leu + Pro210Ala + Lys213Glu + Ala216Glu + Tyr217Leu | 2.000 | 3.500 | 1.500 | 2.000 |
| Sorbitol (70% aqueous solution) | 35.000 | 35.000 | 35.000 | 35.000 |
| PEG-6* | 1.000 | 1.000 | 1.000 | 1.000 |
| Silica dental abrasive** | 20.000 | 20.000 | 20.000 | 20.000 |
| Sodium fluoride | 0.243 | 0.243 | 0.243 | 0.243 |
| Titanium dioxide | 0.500 | 0.500 | 0.500 | 0.500 |
| Sodium saccharin | 0.286 | 0.286 | 0.286 | 0.286 |
| Sodium alkyl sulfate (27.9% aqueous solution) | 4.000 | 4.000 | 4.000 | 4.000 |
| Flavor | 1.040 | 1.040 | 1.040 | 1.040 |
| Carboxyvinyl Polymer*** | 0.300 | 0.300 | 0.300 | 0.300 |
| Carrageenan**** | 0.800 | 0.800 | 0.800 | 0.800 |
| Water | balance to 100% | | | |

*PEG 6 = Polyethylene glycol having a molecular weight of 600.
**Precipitated silica identified as Zeodent 119 offered by J. M. Huber.
***Carbopol offered by B. F. Goodrich Chemical Company.
****Iota Carrageenan offered by Hercules Chemical Company.

In Examples 71–74 the BPN' variants recited in Tables 2–12, among others, are substituted for Ile205Leu+Pro210Ala+Lys213Glu+Ala216Glu+Tyr217Leu, with substantially similar results.

Examples 75–78
Mouthwash Composition

| Component | Example No. 75 | 76 | 77 | 78 |
|---|---|---|---|---|
| Ala216Gly | 3.00 | 7.50 | 1.00 | 5.00 |
| SDA 40 Alcohol | 8.00 | 8.00 | 8.00 | 8.00 |
| Flavor | 0.08 | 0.08 | 0.08 | 0.08 |
| Emulsifier | 0.08 | 0.08 | 0.08 | 0.08 |
| Sodium Fluoride | 0.05 | 0.05 | 0.05 | 0.05 |
| Glycerin | 10.00 | 10.00 | 10.00 | 10.00 |
| Sweetener | 0.02 | 0.02 | 0.02 | 0.02 |
| Benzoic acid | 0.05 | 0.05 | 0.05 | 0.05 |
| Sodium hydroxide | 0.20 | 0.20 | 0.20 | 0.20 |
| Dye | 0.04 | 0.04 | 0.04 | 0.04 |
| Water | balance to 100% | | | |

In Examples 75–78, the BPN' variants recited in Tables 2–12, among others, are substituted for Ala216Gly, with substantially similar results.

Examples 79–82
Lozenge Composition

| Component | Example No. 79 | 80 | 81 | 82 |
|---|---|---|---|---|
| Tyr214Phe + Tyr217Asn | 0.01 | 0.03 | 0.10 | 0.02 |
| Sorbitol | 17.50 | 17.50 | 17.50 | 17.50 |
| Mannitol | 17.50 | 17.50 | 17.50 | 17.50 |
| Starch | 13.60 | 13.60 | 13.60 | 13.60 |
| Sweetener | 1.20 | 1.20 | 1.20 | 1.20 |
| Flavor | 11.70 | 11.70 | 11.70 | 11.70 |
| Color | 0.10 | 0.10 | 0.10 | 0.10 |
| Corn Syrup | balance to 100% | | | |

In Examples 79–82, the BPN' variants recited in Tables 2–12, among others, are substituted for Tyr214Phe+Tyr217Asn, with substantially similar results.

| Examples 83–86 Chewing Gum Composition | | | | |
|---|---|---|---|---|
| | Example No. | | | |
| Component | 83 | 84 | 85 | 86 |
| Ile205Val + Pro210Ala + Lys213Glu | 0.03 | 0.02 | 0.10 | 0.05 |
| Sorbitol crystals | 38.44 | 38.40 | 38.40 | 38.40 |
| Paloja-T gum base* | 20.00 | 20.00 | 20.00 | 20.00 |
| Sorbitol (70% aqueous solution) | 22.00 | 22.00 | 22.00 | 22.00 |
| Mannitol | 10.00 | 10.00 | 10.00 | 10.00 |
| Glycerine | 7.56 | 7.56 | 7.56 | 7.56 |
| Flavor | 1.00 | 1.00 | 1.00 | 1.00 |

*Supplied by L. A. Dreyfus Company.

In Examples 83–86, the BPN' variants recited in Tables 2–12, among others, are substituted for Ile205Val+Pro210Ala+Lys213Glu, with substantially similar results.

2. Denture Cleaning Compositions

In another embodiment of the present invention, denture cleaning compositions for cleaning dentures outside of the oral cavity comprise one or more enzyme variants of the present invention. Such denture cleaning compositions comprise an effective amount of one or more of the enzyme variants, preferably from about 0.0001% to about 50% of one or more of the enzyme variants, more preferably from about 0.001% to about 35%, more preferably still from about 0.01% to about 20%, by weight of the composition, and a denture cleansing carrier. Various denture cleansing composition formats such as effervescent tablets and the like are well known in the art (see for example U.S. Pat. No. 5,055,305, Young, incorporated herein by reference), and are generally appropriate for incorporation of one or more of the enzyme variants for removing proteinaceous stains from dentures.

The denture cleaning composition embodiment of the present invention is illustrated by the following examples.

| Examples 87–90 Two-layer Effervescent Denture Cleansing Tablet | | | | |
|---|---|---|---|---|
| | Example No. | | | |
| Component | 87 | 88 | 89 | 90 |
| Acidic Layer | | | | |
| Ala216Glu | 1.0 | 1.5 | 0.01 | 0.05 |
| Tartaric acid | 24.0 | 24.0 | 24.00 | 24.00 |
| Sodium carbonate | 4.0 | 4.0 | 4.00 | 4.00 |
| Sulphamic acid | 10.0 | 10.0 | 10.00 | 10.00 |
| PEG 20,000 | 4.0 | 4.0 | 4.00 | 4.00 |
| Sodium bicarbonate | 24.5 | 24.5 | 24.50 | 24.50 |
| Potassium persulfate | 15.0 | 15.0 | 15.00 | 15.00 |
| Sodium acid pyrophosphate | 7.0 | 7.0 | 7.00 | 7.00 |
| Pyrogenic silica | 2.0 | 2.0 | 2.00 | 2.00 |
| TAED* | 7.0 | 7.0 | 7.00 | 7.00 |
| Ricinoleytsulfosuccinate | 0.5 | 0.5 | 0.50 | 0.50 |
| Flavor | 1.0 | 1.0 | 1.00 | 1.00 |
| Alkaline Layer | | | | |
| Sodium perborate monohydrate | 32.0 | 32.0 | 32.00 | 32.00 |
| Sodium bicarbonate | 19.0 | 19.0 | 19.00 | 19.00 |
| EDTA | 3.0 | 3.0 | 3.00 | 3.00 |
| Sodium tripolyphosphate | 12.0 | 12.0 | 12.00 | 12.00 |
| PEG 20,000 | 2.0 | 2.0 | 2.00 | 2.00 |
| Potassium persulfate | 26.0 | 26.0 | 26.00 | 26.00 |
| Sodium carbonate | 2.0 | 2.0 | 2.00 | 2.00 |
| Pyrogenic silica | 2.0 | 2.0 | 2.00 | 2.00 |
| Dye/flavor | 2.0 | 2.0 | 2.00 | 2.00 |

*Tetraacetylethylene diamine

In Examples 87–90, the BPN' variants recited in Tables 2–12, among others, are substituted for Ala216Glu, with substantially similar results.

3. Contact Lens Cleaning Compositions

In another embodiment of the present invention, contact lens cleaning compositions comprise one or more enzyme variants of the present invention. Such contact lens cleaning compositions comprise an effective amount of one or more of the enzyme variants, preferably from about 0.01% to about 50% of one or more of the enzyme variants, more preferably from about 0.01% to about 20%, more preferably still from about 1% to about 5%, by weight of the composition, and a contact lens cleaning carrier. Various contact lens cleaning composition formats such as tablets, liquids and the like are well known in the art (see for example U.S. Pat. No. 4,863,627, Davies, Meaken and Rees, issued Sep. 5, 1989; U.S. Pat. Re. No. 32,672, Huth, Lam and Kirai, reissued May 24, 1988; U.S. Pat. No. 4,609,493, Schafer, issued Sep. 2, 1986; U.S. Pat. No. 4,690,793, Ogunbiyi and Smith, issued Sep. 1, 1987; U.S. Pat. No. 4,614,549, Ogunbiyi, Riedhammer and Smith, issued Sep. 30, 1986; and U.S. Pat. No. 4,285,738, Ogata, issued Aug. 25, 1981; each of which are incorporated herein by reference), and are generally appropriate for incorporation of one or more enzyme variants of the present invention for removing proteinaceous stains from contact lens.

The contact lens cleaning composition embodiment of the present invention is illustrated by the following examples.

| Examples 91–94 Enzymatic Contact Lens Cleaning Solution | | | | |
|---|---|---|---|---|
| | Example No. | | | |
| Component | 91 | 92 | 93 | 94 |
| Ile205Leu + Ala216Asp | 0.01 | 0.5 | 0.1 | 2.0 |
| Glucose | 50.00 | 50.0 | 50.0 | 50.0 |
| Nonionic surfactant (polyoxyethlene-polyoxypropylene copolymer) | 2.00 | 2.0 | 2.0 | 2.0 |
| Anionic surfactant (polyoxyethylene-alkylphenylether sodium sulfricester) | 1.00 | 1.0 | 1.0 | 1.0 |
| Sodium chloride | 1.00 | 1.0 | 1.0 | 1.0 |
| Borax | 0.30 | 0.3 | 0.3 | 0.3 |
| Water | balance to 100% | | | |

In Examples 91–94, the BPN' variants recited in Tables 2–12, among others, are substituted for Ile205Leu+Ala216Asp, with substantially similar results.

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of the invention.

What is claimed is:

1. A BPN' variant having a modified amino acid sequence of the Subtilisin BPN' wild-type amino acid sequence set forth in SEO ID NO:1, wherein the modified amino acid sequence comprises a substitution at one or more of positions 200, 201, 202, 203, 205, 206, 207, 208, 209, 210, 211, 212, 216, 219 or 220, wherein
   a. when a substitution occurs at position 200, the substituting amino acid is His, Thr, Pro, Gly, Gln, Asn, Ser, Asp or Glu;
   b. when a substitution occurs at position 201, the substituting amino acid is Gly, Gln, Asn, Ser, Asp or Glu;
   c. when a substitution occurs at position 202, the substituting amino acid is Pro, Gln, Asn, Ser, Asp or Glu;
   d. when a substitution occurs at position 203, the substituting amino acid is Met, Cys, His, Pro, Gly, Gln, Asn, Ser, Asp or Glu;
   e. f. when a substitution occurs at position 205, the substituting amino acid is Leu, Met, Cys, Ala, His, Thr, Pro, Gly, Gln, Asn, Ser, Asp or Glu;
   f. when a substitution occurs at position 206, the substituting amino acid is Pro, Asn or Ser;
   g. when a substitution occurs at position 207, the substituting amino acid is Asp or Glu;
   h. when a substitution occurs at position 208, the substituting amino acid is Pro, Gly, Gln, Asn or Ser; wherein when position 208 is substituted, the variant is not a double mutation variant having a substitution at position 214, or a triple mutation variant having substitutions at positions 214 and 219;
   i. when a substitution occurs at position 209, the substituting amino acid is Ile, Val, Met, Cys, Ala, His, Thr, Pro, Gly, Gln, Asn, Ser, Asp or Glu;
   j. when a substitution occurs at position 210, the substituting amino acid is Gly, Gln, Asn, Ser, Asp or Glu;
   k. when a substitution occurs at position 211, the substituting amino acid is Ala, Pro, Gln, Asn, Ser, Asp or Glu;
   l. when a substitution occurs at position 212, the substituting amino acid is Gln, Ser, Asp or Glu;
   m. when a substitution occurs at position 216, the substituting amino acid is His, Thr, Pro, Gly, Gln, Asn, Ser, Asp or Glu;
   n. when a substitution occurs at position 219, the substituting amino acid is Pro, Gln, Asn, Ser, Asp or Glu; and
   o. when a substitution occurs at position 220, the substituting amino acid is Pro, Gly, Gln, Asn, Asp or Glu;
whereby the BPN' variant has decreased adsorption to, and increased hydrolysis of, an insoluble substrate as compared to wild-type subtilisin BPN'.

2. The BPN' variant of claim 1 wherein
   a. when a substitution occurs at position 206, the substituting amino acid is Asn or Ser; and
   b. when a substitution occurs at position 211, the substituting amino acid is Pro, Gln, Asn, Ser, Asp or Glu.

3. The BPN' variant of claim 1 wherein when the substitution occurs at position 216, the substituting amino acid is Gly.

4. The BPN' variant of claim 2 wherein when a substitution occurs at one or more of positions 200, 201, 202, 203, 205, 207, 209, 210, 211, 212, 216, 219 or 220, the substituting amino acid for any of positions 200, 201, 202, 203, 205, 207, 209, 210, 211, 212, 216, 219 or 220 is Asp or Glu.

5. The BPN' variant of claim 1 comprising a single amino acid substitution, wherein the substitution is:

a. Glu for Ala at position 216,
   b. Asp for Ala at position 216, or
   c. Glu for Val at position 203.

6. The BPN' variant of claim 4 comprising a substitution at one or more of positions of 200, 201, 202, 205, 207, 208, 209, 210, 211, or 212.

7. An isolated BPN' variant having a modified amino acid sequence of the Subtilisin BPN' wild-type amino acid sequence set forth in SEQ ID NO:1, wherein the modified amino acid sequence comprises a substitution at two or more of positions 199, 200, 201, 202, 203, 204, 205, 206, 207, 208, 209, 210, 211, 212, 213, 214, 215, 216, 217, 218, 219 or 220, wherein
   a. when a substitution occurs at position 199, the substituting amino acid is Cys, Ala, His, Thr, Pro, Gly, Gln, Asn, Ser, Asp or Glu;
   b. when a substitution occurs at position 200, the substituting amino acid is His, Thr, Pro, Gly, Gln, Asn, Ser, Asp or Glu;
   c. when a substitution occurs at position 201, the substituting amino acid is Gly, Gln, Asn, Ser, Asp or Glu;
   d. when a substitution occurs at position 202, the substituting amino acid is Pro, Gln, Asn, Ser, Asp or Glu;
   e. when a substitution occurs at position 203, the substituting amino acid is Met, Cys, Ala, His, Thr, Pro, Gly, Gln, Asn, Ser, Asp or Glu;
   f. when a substitution occurs at position 204, the substituting amino acid is Asp or Glu,
   g. when a substitution occurs at position 205, the substituting amino acid is Leu, Val, Met, Cys, Ala, His, Thr, Pro, Gly, Gln, Asn, Ser, Asp or Glu;
   h. when a substitution occurs at position 206, the substituting amino acid is Pro, Asn, Ser, Asp, or Glu;
   i. when a substitution occurs at position 207, the substituting amino acid is Asp or Glu;
   j. when a substitution occurs at position 208, the substituting amino acid is Pro, Gly, Gln, Asn, Ser, Asp or Glu;
   k. when a substitution occurs at position 209, the substituting amino acid is Ile, Val, Met, Cys, Ala, His, Thr, Pro, Gly, Gln, Asn, Ser, Asp or Glu;
   l. when a substitution occurs at position 210, the substituting amino acid is Ala, Gly, Gln, Asn, Ser, Asp or Glu;
   m. when a substitution occurs at position 21 1, the substituting amino acid is Ala, Pro, Gln, Asn, Ser, Asp or Glu;
   n. when a substitution occurs at position 212, the substituting amino acid is Gln, Ser, Asp or Glu;
   o. when a substitution occurs at position 213, the substituting amino acid is Trp, Phe, Tyr, Leu, Ile, Val, Met, Cys, Ala, His, Thr, Pro, Gly, Gln, Asn, Ser, Asp or Glu; wherein when position 213 is substituted, the variant is not a double, triple, quadruple, quintuple, sextuple, or septuple mutation variant having substitutions at positions selected from the group consisting of 206, 208, 213, 214, 218, and
   p. when a substitution occurs at position 214, the substituting amino acid is Phe, Leu, Ile, Val, Met, Cys, Ala, His, Thr, Pro, Gly, Gln, Asn, Ser, Asp or Glu, wherein when position 214 is substituted, the variant is not a double mutation variant having a substitution at position 217, or a double, triple, quadruple, quintuple, sextuple, or septuple mutation variant having substitutions at positions selected from the group consisting of 206, 208, 213, 214, 218, and 219;

q when a substitution occurs at position 215, the substituting amino acid is Thr, Pro, Gln, Asn, Ser, Asp or Glu; wherein when position 215 is substituted, the variant is not a double mutation variant having a substitution at position 217, or is not a double, triple, quadruple, quintuple, sextuple, or septuple mutation variant having substitutions at positions selected from the group consisting of 206, 208, 213, 214, 218, and 219;

r. when a substitution occurs at position 216, the substituting amino acid is His, Thr, Pro, Gly, Gln, Asn, Ser, Asp or Glu;

s. when a substitution occurs at position 217, the substituting amino acid is Leu, Ile, Val, Met, Cys, Ala, His, Thr, Pro, Gly, Gln, Asn, Ser, Asp or Glu; wherein when position 217 is substituted, the variant is not a double, triple, quadruple, quintuple, sextuple, or septuple mutation variant having substitutions at positions selected from the group consisting of 206, 208, 213, 214, 218, and 219;

t. when a substitution occurs at position 218, the substituting amino acid is Gln, Ser, Asp or Glu; wherein when the substituting amino acid at position 218 is Ser or Glu, the BPN' variant is not a double mutation variant having substitutions at positions 208 and 218 wherein the substituting amino acid at position 208 is Asp or Glu, or at positions 214 and 218 wherein the substituting amino acid at position 214 is Asp or Glu, or a triple mutation variant having substitutions at positions 208, 214, and 218 wherein the substituting amino acid at position 208 is Asp or Glu and the substituting amino acid at position 214 is Asp or Glu; and wherein when the substituting amino acid at position 218 is Ser, Asp, or Glu, the BPN' variant is not a double, triple, quadruple, quintuple, sextuple, or septuple mutation variant having substitutions at positions selected from the group consisting of 204, 213, 214, 215, and 217;

u. when a substitution occurs at position 219, the substituting amino acid is Pro, Gln, Asn, Ser, Asp or Glu; and v. when a substitution occurs at position 220, the substituting amino acid is Pro, Gly, Gln, Asn, Ser, Asp or Glu;

whereby the BPN' variant has decreased adsorption to, and increased hydrolysis of, an insoluble substrate as compared to wild-type subtilisin BPN'.

8. The BPN' variant of claim 7 wherein a. when a substitution occurs at position 206, the substituting amino acid is Asn or Ser;

b. when a substitution occurs at position 210, the substituting amino acid is Gly, Gln, Asn, Ser, Asp or Glu;

c. when a substitution occurs at position 211, the substituting amino acid is Pro, Gln, Asn, Ser, Asp or Glu;

d. when a substitution occurs at position 214, the substituting amino acid is Leu, Ile, Val, Met, Cys, Ala, His, Pro, Gly, Gln, Asn, Asp or Glu; and e. when a substitution occurs at position 215, the substituting amino acid is Pro, Gln, Asn, Ser, Asp or Glu.

9. The BPN' variant of claim 8 wherein the substituting amino acid for any of positions 199, 200, 201, 202, 203, 204, 205, 206, 207, 208, 209, 210, 211, 212, 214, 215, 216, 217, 218, 219 or 220 is Asp or Glu; and when a substitution occurs at position 213, the substituting amino acid for position 213 is Asp.

10. The BPN' variant of claim 8 comprising a substitution at two or more of positions 199, 200, 201, 202, 205, 207, 208, 209, 210, 211, 212, or 215.

11. The BPN' variant of claim 10 comprising a substitution at two or more of positions 200, 201, 202, 205 or 207.

12. The BPN' variant of claim 7 comprising two amino acid substitutions, wherein the substitutions are:

a. Ala for Pro at position 210 and Thr for Gly at position 215;

b. Glu for Gln at position 206 and Glu for Ala at position 216;

c. Glu for Ala at position 216 and Leu for Tyr at position 217;

d. Giu for Lys at position 213 and Leu for Tyr at position 217;

e. Glu for Lys at position 213 and Glu for Ala at position 216;

f. Leu for Ile at position 205 and Glu for Ala at position 216; or g. Leu for Ile at position 205 and Asp for Ala at position 216.

13. An isolated BPN' variant having a modified amino acid sequence of the Subtilisin BPN' wild-type amino acid sequence set forth in SEQ ID NO:1, wherein the modified amino acid sequence comprises a substitution at three or more of positions 199, 200, 201, 202, 203, 204, 205, 206, 207, 208, 209, 210, 211, 212, 213, 214, 215, 216, 217, 218, 219 or 220, wherein a. when a substitution occurs at position 199, the substituting amino acid is Cys, Ala, His, Thr, Pro, Gly, Gln, Asn, Ser, Asp or Glu;

b. when a substitution occurs at position 200, the substituting amino acid is His, Thr, Pro, Gly, Gln, Asn, Ser, Asp or Glu;

c. when a substitution occurs at position 201, the substituting amino acid is Gly, Gln, Asn, Ser, Asp or Glu;

d. when a substitution occurs at position 202, the substituting amino acid is Pro, Gln, Asn, Ser, Asp or Glu;

e. when a substitution occurs at position 203, the substituting amino acid is Met, Cys, Ala, His, Thr, Pro, Gly, Gln, Asn, Ser, Asp or Glu;

f. when a substitution occurs at position 204, the substituting amino acid is Asp, or Glu;

g. when a substitution occurs at position 205, the substituting amino acid is Leu, Val, Met, Cys, Ala, His, Thr, Pro, Gly, Gln, Asn, Ser, Asp or Glu;

h. when a substitution occurs at position 206, the substituting amino acid is Pro, Asn, Ser, Asp, or Glu;

i. when a substitution occurs at position 207, the substituting amino acid is Asp or Glu;

j. when a substitution occurs at position 208, the substituting amino acid is Pro, Gly, Gln, Asn, Ser, Asp or Glu;

k. when a substitution occurs at position 209, the substituting amino acid is Ile, Val, Met, Cys, Ala, His, Thr, Pro, Gly, Gln, Asn, Ser, Asp or Glu;

l. when a substitution occurs at position 210, the substituting amino acid is Ala, Gly, Gln, Asn, Ser, Asp or Glu;

m. when a substitution occurs at position 211, the substituting amino acid is Ala, Pro, Gln, Asn, Ser, Asp or Glu;

n. when a substitution occurs at position 212, the substituting amino acid is Gln, Ser, Asp or Glu;

o. when a substitution occurs at position 213, thesubstituting amino acid is Trp, Phe, Tyr, Leu, Ile, Val, Met, Cys, Ala, His, Thr, Pro, Gly, Gln, Asn, Ser, Asp or Glu; wherein when position 213 is substituted, the variant is not a triple, quadruple, quintuple, sextuple, or septuple mutation variant having substitutions at positions selected from the group consisting of 206, 208, 213, 214, 218, and 2199;

p. when a substitution occurs at position 214, the substituting amino acid is Phe, Leu, Ile, Val, Met, Cys, Ala, His, Thr, Pro, Gly, Gln, Asn, Ser, Asp or Glu; wherein when position 214 is substituted, the variant is not a triple, quadruple, quintuple, sextuple, or septuple mutation variant having substitutions at positions selected from the group consisting of 206, 208, 213, 214, 218, and 219;

q. when a substitution occurs at position 215, the substituting amino acid is Thr, Pro, Gln, Asn, Ser, Asp or Glu; wherein when position 215 is substituted, the variant is not a triple, quadruple, quintuple, sextuple, or septuple mutation variant having substitutions at positions selected from the group consisting of 206, 208, 213, 214, 218, and 219;

r. when a substitution occurs at position 216, the substituting amino acid is His, Thr, Pro, Gly, Gln, Asn, Ser, Asp or Glu;

s. when a substitution occurs at position 217, the substituting amino acid is Leu, Ile, Val, Met, Cys, Ala, His, Thr, Pro, Gly, Gln, Asn, Ser, Asp or Glu: wherein when position 217 is substituted, the variant is not a triple, quadruple, quintuple, sextuple, or septuple mutation variant having substitutions at positions selected from the group consisting of 206, 208, 213, 214, 218, and 219;

t. when a substitution occurs at position 218, the substituting amino acid is Gln, Ser, Asp or Glu; wherein when the substituting amino acid at position 218 is Ser or Glu, the BPN' variant is not a triple mutation variant having substitutions at positions 208, 214, and 218, wherein the substituting amino acid at position 208 is Asp or Glu and the substituting amino acid at position 214 is Asp or Glu;

wherein the variant is not a quadruple mutation variant having substitutions at positions 208, 214, and 219; and wherein when the substituting amino acid at position 218 is Ser, Asp, or Glu, the BPN' variant is not a triple, quadruple, quintuple, sextuple, or septuple mutation variant having substitutions at positions selected from the group consisting of 204, 213, 214, 215, and 217;

u. when a substitution occurs at position 219, the substituting amino acid is Pro, Gln, Asn, Ser, Asp or Glu; wherein the variant is not a triple mutation variant having substitutions at positions 208 and 214; and v. when a substitution occurs at position 220, the substituting amino acid is Pro, Gly, Gln, Asn, Ser Asp or Glu;

whereby the BPN' variant has decreased adsorption to, and increased hydrolysis of, an insoluble substrate as compared to wild-type subtilisin BPN'.

14. The BPN' variant of claim 13 wherein
a. when a substitution occurs at position 206, the substituting amino acid is Asn or Ser;
b. when a substitution occurs at position 210, the substituting amino acid is Gly, Gln, Asn, Ser, Asp or Glu;
c. when a substitution occurs at position 211, the substituting amino acid is Pro, Gln, Asn, Ser, Asp or Glu;
d. when a substitution occurs at position 214, the substituting amino is Leu, Ile, Val, Met, Cys, Ala, His, Pro, Gly, Gln, Asn, Asp or Glu; and
e. when a substitution occurs at position 215, the substituting amino is Pro, Gln, Asn, Ser. Asp or Glu.

15. The BPN' variant of claim 14 comprising a substitution at three or more of positions 199, 200, 201, 202, 205, 207, 208, 209, 210, 211, 212, or 215.

16. The BPN' variant of claim 15 comprising a substitution at three or more of positions 200, 201, 202, 205 or 207.

17. The BPN' variant of claim 13 comprising three amino acid substitutions, wherein the substitutions are:
a. Pro substituted for Gln at position 206, Ala substituted for Gly at postition 211, and Glu substituted for Ala at position 216;
b. Val substituted for Ile at position 205, Ala substituted for Pro at position 210, and Glu substituted for Lys at position 213;
c. Glu substituted for Gln at position 206, Glu substituted for Ala at position 216, and Leu substituted for Tyr at position 217;
d. Glu substituted for Gln at position 206, Glu substituted for Lys at position 213, and Leu substituted for Tyr at position 217; or
e. Glu substituted for Lys at position 213, Glu substituted for Ala at position 216, and Leu substituted for Tyr at position 217.

18. The BPN' variant of claim 13 comprising four amino acid substitutions, wherein the substitutions are:
a. Ala substituted for Pro at position 210, Glu substituted for Lys at position 213, Glu substituted for Ala at position 216, and Leu substituted for Tyr at position 217;
b. Glu substituted for Gln at position 206, Glu substituted for Lys at position 213, Glu substituted for Ala at position 216, and Leu substituted for Tyr at position 217; or
c. Glu substituted for Ser at position 204, Glu substituted for Gln at position 206, Glu substituted for Ala at position 216, and Leu substituted for Tyr at position 217.

19. The BPN' variant of claim 13 comprising five amino acid substitutions, wherein the substitutions are:
a. Leu for Ile at position 205, Ala for Pro at position 210, Glu for Lys at position 213, Glu for Ala at positions 216, and Leu for Tyr at position 217; or
b. Glu for Ser at position 204, Glu for Gln at position 206, Glu for Lys at position 213, Glu for Ala at position 216, and Leu for Tyr at position 217.

20. A cleaning composition selected from the group consisting of a hard surface cleaning composition, a dishwashing composition, an oral cleaning composition, a denture cleansing composition, a contact lens cleaning composition and a fabric cleaning composition, wherein the cleaning composition comprises the BPN' variant of claim 1 and a cleaning composition carrier.

21. A cleaning composition selected from the group consisting of a hard surface cleaning composition, a dishwashing composition, an oral cleaning composition, a denture cleansing composition, a contact lens cleaning composition and a fabric cleaning composition, wherein the cleaning composition comprises the BPN' variant of claim 7 and a cleaning composition carrier.

22. A cleaning composition selected from the group consisting of a hard surface cleaning composition, a dishwashing composition, an oral cleaning composition, a denture cleansing composition, a contact lens cleaning composition and a fabric cleaning composition, wherein the cleaning composition comprises the BPN' variant of claim 13 and a cleaning composition carrier.

23. A hard surface cleaning composition comprising the BPN' variant of claim 1 and a hard surface cleaning carrier.

24. A hard surface cleaning composition comprising the BPN' variant of claim 7 and a hard surface cleaning carrier.

25. A hard surface cleaning composition comprising the BPN' variant of claim 13 and a hard surface cleaning carrier.

26. A fabric cleaning composition comprising the BPN' variant of claim 1.

27. The fabric cleaning composition of claim 26, wherein said composition is in the form of a liquid.

28. The fabric cleaning composition of claim 26, wherein the composition comprises at least about 5% surfactant and at least about 5% builder, by weight of the composition.

29. The fabric cleaning composition of claim 28 further comprising cleaning composition materials selected from the group consisting of solvents, buffers, enzymes, soil release agents, clay soil removal agents, dispersing agents, brighteners, suds suppressors, fabric softeners, suds boosters, enzyme stabilizers, bleaching agents, dyes, perfumes, and mixtures thereof.

30. The fabric cleaning composition of claim 29 further comprising at least one bleaching agent.

31. A insolated mutant BPN' gene encoding the BPN' variant of claim 1.

32. A insolated mutant BPN' gene encoding the BPN' variant of claim 7.

33. An isolated mutant BPN' gene encoding the BPN' variant of claim 13.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
       (A) LENGTH: 275 amino acids
       (B) TYPE: amino acid
       (D) TOPOLOGY: linear (ii) MOLECULE TYPE: protein (xi) SEQUENCE DESCRIPTION: SEQ ID NO:1:

```
Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
    130                 135                 140

Ser Gly Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275
```